US00RE44681E

(19) United States
(12) Reissued Patent
Violette et al.

(10) Patent Number: US RE44,681 E
(45) Date of Reissued Patent: Dec. 31, 2013

(54) COMPOSITIONS AND METHODS FOR INHIBITING GROWTH OF SMAD4-DEFICIENT CANCERS

(71) Applicant: Biogen Idec MA Inc., Cambridge, MA (US)

(72) Inventors: Shelia M. Violette, Lexington, MA (US); Louise A. Koopman, Chestnut Hill, MA (US)

(73) Assignee: Biogen Idec MA Inc., Cambridge, MA (US)

(21) Appl. No.: 13/863,646

(22) Filed: Apr. 16, 2013

Related U.S. Patent Documents

Reissue of:
(64) Patent No.: 7,927,590
Issued: Apr. 19, 2011
Appl. No.: 11/822,859
Filed: Jul. 10, 2007

U.S. Applications:
(60) Provisional application No. 60/819,359, filed on Jul. 10, 2006.

(51) Int. Cl.
*A61K 39/395* (2006.01)
*C07K 16/00* (2006.01)

(52) U.S. Cl.
USPC ..... 424/130.1; 530/387.1

(58) Field of Classification Search
None
See application file for complete search history.

(56) References Cited

U.S. PATENT DOCUMENTS

| | | | | |
|---|---|---|---|---|
| 3,773,919 | A | 11/1973 | Boswell et al. | |
| 4,683,195 | A | 7/1987 | Mullis et al. | |
| 4,975,278 | A | 12/1990 | Senter et al. | |
| 5,019,368 | A | 5/1991 | Epstein et al. | |
| 5,208,020 | A | 5/1993 | Chari et al. | |
| 5,223,493 | A | 6/1993 | Boltralik | |
| 5,225,539 | A | 7/1993 | Winter et al. | |
| 5,420,120 | A | 5/1995 | Boltralik | |
| 5,530,101 | A | 6/1996 | Queen et al. | |
| 5,565,332 | A | 10/1996 | Hoogenboom et al. | |
| 5,580,859 | A | 12/1996 | Feigner et al. | |
| 5,589,466 | A | 12/1996 | Feigner et al. | |
| 5,654,316 | A | 8/1997 | Carruthers et al. | |
| 5,688,960 | A | 11/1997 | Shankar | |
| 5,691,362 | A | 11/1997 | McCormick et al. | |
| 5,693,761 | A | 12/1997 | Queen et al. | |
| 5,696,267 | A | 12/1997 | Reichard et al. | |
| 5,719,156 | A | 2/1998 | Shue et al. | |
| 5,733,743 | A | 3/1998 | Johnson et al. | |
| 5,783,579 | A | 7/1998 | McCormick | |
| 5,789,422 | A | 8/1998 | Reichard et al. | |
| 5,789,650 | A | 8/1998 | Lonberg et al. | |
| 5,795,894 | A | 8/1998 | Shue et al. | |
| 5,798,359 | A | 8/1998 | Shue et al. | |
| 5,821,337 | A | 10/1998 | Carter et al. | |
| 5,827,690 | A | 10/1998 | Meade et al. | |
| 5,859,205 | A | 1/1999 | Adair et al. | |
| 5,869,619 | A | 2/1999 | Studnicka | |
| 5,892,019 | A | 4/1999 | Schlom et al. | |
| 5,939,598 | A | 8/1999 | Kucherlapati et al. | |
| 5,942,417 | A * | 8/1999 | Ni et al. | 435/69.1 |
| 5,962,643 | A | 10/1999 | Sheppard et al. | |
| 5,985,278 | A | 11/1999 | Mitjans et al. | |
| 6,075,181 | A | 6/2000 | Kucherlapati et al. | |
| 6,150,584 | A | 11/2000 | Kucherlapati et al. | |
| 6,162,963 | A | 12/2000 | Kucherlapati et al. | |
| 6,180,370 | B1 | 1/2001 | Queen et al. | |
| 6,267,958 | B1 | 7/2001 | Andya et al. | |
| 6,291,650 | B1 | 9/2001 | Winter et al. | |
| 6,300,064 | B1 | 10/2001 | Knappik et al. | |
| 6,303,313 | B1 | 10/2001 | Wigler et al. | |
| 6,307,026 | B1 | 10/2001 | King et al. | |
| 6,358,710 | B1 | 3/2002 | Graves et al. | |
| 6,692,741 | B2 | 2/2004 | Huang et al. | |
| 6,787,322 | B2 | 9/2004 | Sheppard et al. | |
| 7,465,449 | B2 | 12/2008 | Violette et al. | |

(Continued)

FOREIGN PATENT DOCUMENTS

| | | |
|---|---|---|
| CA | 2 355 874 | 6/2000 |
| EP | 239 400 | 9/1987 |

(Continued)

OTHER PUBLICATIONS

Riechmann et al., "Reshaping human antibodies for therapy," *Nature*, 332(24):323-327, (1988).

(Continued)

*Primary Examiner* — Sean Aeder
(74) *Attorney, Agent, or Firm* — Fish & Richardson P.C.

(57) ABSTRACT

The present invention is in the fields of cell biology, immunology and oncology. The invention relates to the discovery that there is a relationship between the expression levels of the tumor suppressor gene smad4 (also known as dpc4) and integrin $\alpha_v\beta_6$, and the responsiveness of patient populations to $\alpha_v\beta_6$-active compounds and compositions (e.g., antibodies and other ligands that bind $\alpha_v\beta_6$), particularly in cancer cells from such patient populations, more particularly on carcinomas such as pancreatic carcinomas. The invention thus provides methods for determining the responsiveness of tumor cells (particularly those from pancreatic tumors) to such $\alpha_v\beta_6$-active compounds and compositions by examining the expression of $\alpha_v\beta_6$ and smad4 by the tumor cells, as well as methods of diagnosis and treatment/prevention of tumor progression using ligands, including antibodies and molecule drugs, that bind to integrin $\alpha_v\beta_6$ on the surfaces of tumor cells and/or that block one or more components of the TGF-β pathway, particularly in smad4-deficient tumor cells.

41 Claims, 57 Drawing Sheets

(56) References Cited

U.S. PATENT DOCUMENTS

| | | | | |
|---|---|---|---|---|
| 7,544,358 | B2 | 6/2009 | Huang et al. | |
| 7,550,142 | B2 | 6/2009 | Giles-Komar et al. | |
| 7,927,590 | B2 | 4/2011 | Violette et al. | |
| 7,943,742 | B2 | 5/2011 | Violette et al. | |
| 8,153,126 | B2 | 4/2012 | Violette et al. | |
| 2001/0056076 | A1 | 12/2001 | Huang et al. | |
| 2002/0004482 | A1 | 1/2002 | Huang et al. | |
| 2004/0048312 | A1* | 3/2004 | Li et al. | 435/7.1 |
| 2004/0142877 | A1 | 7/2004 | Schadt et al. | |
| 2004/0253311 | A1 | 12/2004 | Berlin et al. | |
| 2005/0148562 | A1 | 7/2005 | Pairet et al. | |
| 2005/0255102 | A1* | 11/2005 | Violette et al. | 424/143.1 |
| 2008/0286269 | A1 | 11/2008 | Violette et al. | |
| 2009/0028853 | A1 | 1/2009 | Sheppard et al. | |
| 2011/0287007 | A1 | 11/2011 | Sheppard et al. | |
| 2011/0293512 | A1 | 12/2011 | Violette et al. | |
| 2011/0305629 | A1 | 12/2011 | Violette et al. | |
| 2012/0027754 | A1 | 2/2012 | Sheppard et al. | |
| 2012/0251532 | A1 | 10/2012 | Violette et al. | |

FOREIGN PATENT DOCUMENTS

| | | |
|---|---|---|
| EP | 0 719 859 | 7/1996 |
| EP | 843 961 | 5/1998 |
| JP | 2005-506331 | 3/2005 |
| JP | 2005-528099 | 9/2005 |
| WO | WO 81/01145 | 4/1981 |
| WO | WO 88/07378 | 10/1988 |
| WO | WO 90/07861 | 7/1990 |
| WO | WO 93/21232 | 10/1993 |
| WO | WO 94/11026 | 5/1994 |
| WO | WO 97/06822 | 2/1997 |
| WO | WO 99/07405 | 2/1999 |
| WO | WO 99/37683 | 7/1999 |
| WO | WO 02/12501 | 2/2002 |
| WO | WO 02/50039 | 6/2002 |
| WO | WO 02/083854 | 10/2002 |
| WO | WO 2003/026692 | 4/2003 |
| WO | WO 2003/072040 | 9/2003 |
| WO | 2003/097615 | 11/2003 |
| WO | WO 2003/100033 | 12/2003 |
| WO | WO 2004/056308 | 7/2004 |
| WO | 2005/044794 | 5/2005 |
| WO | WO 2007/008712 | 1/2007 |
| WO | 2008/008315 | 1/2008 |
| WO | 2009/103542 | 8/2009 |
| WO | 2012/031008 | 3/2012 |

OTHER PUBLICATIONS

Davies et al., "Affinity improvement of single antibody VH domains: residues in all three hypervariable regions affect antigen binding," *Immunotech.*, 1996, 2(3):169-179.

Holt et al., "Domain antibodies: proteins for therapy," *Trends in BioTech.*, 2003, 21(11):484-490.

Maynard, "Antibody Engineering," *Annu. Rev. Biomed. Eng.*, 2000, 2:339-376.

Pini et al., "Design and use of a phage display library; Human antibodies with a subnanomolar affinity against a marker of angiogenesis eluted from a two-dimensional gel," *J. Biol. Chem.,* 1998, 273(34):21769-21776.

Abe et al., Anal. Biochem., 216(2):276-284 (1994).

Agrez et al., "The alpha v beta 6 integrin induces gelatinase B secretion in colon cancer cells," Int. J. Cancer, 81(1):90-97 (1999).

Agrez et al., J. Cell Biol., 127(2):547-556 (1994).

Ahmed et al., "Alpha(v)beta(6) integrin-A marker for the malignant potential of epithelial ovarian cancer," J. Histochem. Cytochem., 50(10):1371-1380 (2002).

Ahmed et al., "Overexpression of alpha(v)beta6 integrin in serous epithelial ovarian cancer regulates extracellular matrix degradation via the plasminogen activation cascade," Carcinogenesis, 23(2):237-244 (2002).

Akhurst et al., Trends Cell Biol., 11(11):544-551 (2001).

Akhurst, "TGF-beta antagonists: why suppress a tumor suppressor?," J. Clin. Invest., 109(12):1533-1536 (2002).

Albeda, Lab Invest., 68:4-17 (1993).

Aluwihare et al., "Mice that lack activity of alphavbeta6- and alphavbeta8-integrins reproduce the abnormalities of Tgfbl- and Tgfb3-null mice," J. Cell. Sci., 122(Pt 2):227-32 (2009).

Annes et al., "Making sense of latent TGFbeta activation," J. Cell Sci., 116(Pt 2):217-224 (2003).

Araya et al., "Integrin-mediated transforming growth factor-beta activation regulates homeostasis of the pulmonary epithelial-mesenchymal trophic unit," Am. J. Pathol., 169(2):405-415 (2006).

Arend et al., "Mouse beta(6) integrin sequence, pattern of expression, and role in kidney development," J. Am. Soc. Nephrol., 11(12):2297-2305 (2000).

Baraldo et al., "Decreased expression of TGF-beta type II receptor in bronchial glands of smokers with COPD," Thorax., 60:998-1002 (2005).

Barcellos-Hoff et al , "Immunohistochemical detection of active transforming growth factor-beta in situ using engineered tissue," Am. J. Pathol., 147(5):1228-1237 (1995).

Barcellos-Hoff, Latency and activation in the control of TGF-beta, J. Mammary Gland Biol. Neoplasia, 1(4):353-363 (1996).

Bates et al., "Transcriptional activation of integrin beta6 during the epithelial-mesenchymal transition defines a novel prognostic indicator of aggressive colon carcinoma," J. Clin. Invest., 115(2):339-347 (2005).

Bates et al., "Tumor necrosis factor-alpha stimulates the epithelial-to-mesenchymal transition of human colonic organoids," Mol. Biol. Cell, 14(5):1790-1800 (2003).

Beiboer et al., "Guided selection of a pan carcinoma specific antibody reveals similar binding characteristics yet structural divergence between the original murine antibody and its human equivalent," J. Mol. Biol., 296:833-849 (2000).

Bendig, M.M., Methods: a Companion to Methods in Enzymology, 8:83-93 (1995).

Blobe et al., "Role of transforming growth factor beta in human disease," N. Engl. J. Med., 342:1350-1358 (2000).

Bonniaud et al., "Progressive transforming growth factor beta1-induced lung fibrosis is blocked by an orally active ALK5 kinase inhibitor," Am. J. Respir. Crit. Care Med., 171(8):889-898 (2005).

Bonniaud et al., "Smad3 null mice develop airspace enlargement and are resistant to TGF-beta-mediated pulmonary fibrosis," J. Immunol., 173(3):2099-2108 (2004).

Border et al., "Interactions of transforming growth factor-beta and angiotensin II in renal fibrosis," Hypertension, 31(1 P 2):181-188 (1998).

Bottinger et al., "TGF-beta signaling in renal disease," J. Am. Soc. Nephrol., 13(10):2600-2610 (2002).

Breuss et al., "Expression of the beta 6 integrin subunit in development, neoplasia and tissue repair suggests a role in epithelial remodeling," J. Cell Sci., 108(Pt 6):2241-2251 (1995).

Breuss et al., "Restricted distribution of integrin beta 6 mRNA in primate epithelial tissues," J. Histochem. Cytochem., 41(10):1521-1527 (1993).

Broekelmann et al., "Transforming growth factor beta 1 is present at sites of extracellular matrix gene expression in human pulmonary fibrosis," Proc. Natl. Acad. Sci. USA, 88(15):6642-6646 (1991).

Brown et al., "Tolerance of single, but not multiple, amino acid replacements in antibody VH CDR 2: a means of minimizing B cell wastage from somatic hypermutation?," J. Immunol., 156(9):3285-91 (1996).

Brunton et al., "The protrusive phase and full development of integrin-dependent adhesions in colon epithelial cells require FAK- and ERK-mediated actin spike formation: deregulation in cancer cells," Neoplasia, 3(3):215-226 (2001).

Busk et al., "Characterization of the integrin alpha v beta 6 as a fibronectin-binding protein," J. Biol. Chem., 267(9):5790-5796 (1992).

Carrasquillo et al., "Indium-III T101 monoclonal antibody is superior to iodine-131 T101 in imaging of cutaneous T-cell lymphoma," J. Nucl. Med., 28(3):281-287 (1987).

(56) References Cited

OTHER PUBLICATIONS

Chapman, "Disorders of lung matrix remodeling," J. Clin. Invest., 113(2):148-157 (2004).
Chari et al., "Immunoconjugates containing novel maytansinoids: promising anticancer drugs," Cancer Res., 52(1):127-131 (1992).
Chevalier et al., "Renal tubulointerstitial injury from ureteral obstruction in the neonatal rat is allenuated by IGF-1," Kidney Int., 57(3):882-890 (2000).
Cho et al., J. Clin. Invest., 113:551-560 (2004).
Chorev et al., Biopolymers, 37:367-375 (1995).
Co et al., "Humanized antibodies for antiviral therapy," Proc. Natl. Acad. Sci., 88:2869-2873 (1991).
Collard et al., "Combined corticosteroid and cyclophosphamide therapy does not alter survival in idiopathic pulmonary fibrosis," Chest, 125(6):2169-2174 (2004).
Colman, P.M., Research in Immunology, 145:33-36 (1994).
Cooper et al., Proc. Natl. Acad. Sci. USA, 94:6450-6455 (1997).
Cosgrove et al., "Collagen COL4A3 knockout: a mouse model for autosomal Alport syndrome," Genes Dev., 10 (23):2981-2992 (1996).
Cosgrove et al., "Integrin alpha1beta1 and transforming growth factor-beta 1 play distinct roles in alport glomerular pathogenesis and serve as dual targets for metabolic therapy," Amer. J. Path., 157(5):1649-1659 (2000).
Dai et al., "Transforming growth factor-beta 1 potentiates renal tubular epithelial cell death by a mechanism independent of Smad signaling," J. Biol. Chem., 278(14):12537-12545 (2003).
Damiano, "Integrins as novel drug targets for overcoming innate drug resistance," Curr. Cancer Drug Targets, 2(1):37-43 (2002).
de Boer et al., Am. J. Respir. Crit. Care Med., 158:1951-1957 (1998).
De Pascalis et al., "Grafting of "abbreviated" complementarity-determining regions containing specificity-determining residues essential for ligand contact to engineer a less immunogenic humanized monoclonal antibody," J. Immunol., 169:3076-3084 (2002).
Deman et al., "Altered antioxidant defence in a mouse adriamycin model of glomerulosclerosis," Nephrol. Dial. Transplant., 16(1):147-150 (2001).
Denton et al., "Activation of a fibroblast-specific enhancer of the proalpha2(1) collagen gene in tight-skin mice," Arthritis Rheum., 44(3):712-722 (2001).
Dixit et al., J. Biol. Chem., 271(42):25976-25980 (1996).
Douglas et al., "Colchicine versus prednisone in the treatment of idiopathic pulmonary fibrosis. A randomized prospective study. Members of the Lung Study Group," Am. J. Respir. Crit. Care Med., 158(1):220-225 (1998).
Eickelberg et al., "Extracellular matrix deposition by primary human lung fibroblasts in response to TGF-beta1 and TGF-beta3," Am. J. Physiol., 276(5 Pt 1):L814-L824 (1999).
Esteban et al., "New method for the chelation of indium-III to monoclonal antibodies: biodistribution and imaging of athymic mice bearing human colon carcinoma xenografts," J. Nucl. Med., 28(5):861-870 (1987).
European Search Report for EP App. Ser. No. 06774580, dated Jun. 5, 2009.
European Search Report for EP App. Ser. No. 07810296.9, dated Apr. 8, 2010.
Extended European Search Report for EP App. Ser. No. 10012545.9, dated Apr. 29, 2011.
Extended European Search Report for EP App. Ser. No. 10013155.6, dated Apr. 28, 2011.
European Search Report for EP App. Ser. No. 11008296, dated Apr. 16, 2012.
Franko et al., Radiat. Res., 140(3):347-355 (1994).
George et al., "In vivo inhibition of rat stellate cell activation by soluble transforming growth factor beta type II receptor: a potential new therapy for hepatic fibrosis," Proc. Natl. Acad. Sci. USA, 96(22):12719-12724 (1999).
George et al., Am. J. Pathol., 156(1):115-124 (2000).
Ghannad et al, "Absence of avh6 integrin is linked to initiation and progression of periodontal disease," International Association for Dental Research, IADR, Abstract 85, Jul. 1-5, 2008.
Giusti et al., "Somatic diversification of S107 from an antiphosphocholine to an anti-DNA autoantibody is due to a single base change in its heavy chain variable region," *Sci. U.S.A., Proc. Natl. Acad.* 84(9):2926-30 (1987).
Gleizes et al. "TGF-beta latency: biological significance and mechanisms of activation," Stem Cells, 15(3):190-197 (1997).
Griffiths et al., "Inactivation of the beta 6 integrin subunit gene protects against bleomycin-induced pulmonary fibrosis," *Concurrent Symposium 7: Extracellular Matrix: Regulation and Cell Behavior,* 960-965 (1996), XP-000944784, p. 166A, Abstract only.
Guy et al., "Induction of mammary tumors by expression of polyomavirus middle T oncogene: a transgenic mouse model for metastatic disease," Mol. Cell Biol., 12(3):954-961 (1992).
Hakkinen et al , "Immunolocalization of tenascin-C, alpha9 integrin subunit, and alphavbeta6 integrin during wound healing in human oral mucosa," J. Histochem. Cytochem., 48(7):985-998 (2000).
Hakkinen et al., "Increased expression of beta6-integrin in skin leads to spontaneous development of chronic wounds," Am. J. Pathol., 164(1):229-242 (2004).
Halder et al., "A specific inhibitor of TFG-beta receptor kinase, Sb-431542, as a potent antitumor agent for human cancers," Neoplasia, 7(5):509-521 (2005).
Hamidi et al., "Expression of alpha(v)beta6 integrin in oral leukoplakia," Br. J. Cancer, 82(8):1433-1440 (2000).
Haston et al., "Inheritance of susceptibility to bleomycin-induced pulmonary fibrosis in the mouse," Cancer Res., 56 (11 ):2596-2601 (1996).
Hinman et al., "Preparation and characterization of monoclonal antibody conjugates of the calicheamicins: a novel and potent family of antitumor antibiotics," Cancer Research, 53(14):3336-3342 (1993).
Horan et al., "Partial inhibition of integrin alpha(v)beta6 prevents pulmonary fibrosis without exacerbating inflammation," Am. J. Respir. Crit. Care Med., 177(1):56-65 (2008).
Huang et al., "Inactivation of the integrin beta 6 subunit gene reveals a role of epithelial integrins in regulating inflammation in the lung and skin," J. Cell Biol., 133(4):921-928 (1996).
Huang et al., "The integrin alphavbeta6 is critical for keratinocyte migration on both its known ligand, fibronectin, and on vitronectin," J. Cell Sci., 111(Pt 15):2189-2195 (1998).
Huang et al., Am. J. Respir. Cell Mol. Biol., 13(2):245-251 (1995).
Huang et al., Am. J. Respir. Cell Mol. Biol., 19(4):636-642 (1998).
Hynes, "Integrins: versatility, modulation, and signaling in cell adhesion," Cell, 69:11-25 (1992).
Inazaki et al., "Smad3 deficiency attenuates renal fibrosis, inflammation, and apoptosis after unilateral ureteral obstruction," Kidney Int., 66(2):597-604 (2004).
International Preliminary Report on Patentability for App. Ser. No. PCT/US07/15692, dated Oct. 20, 2011.
International Preliminary Report on Patentability for App. Ser. No. PCT/US2007/081473, dated Apr. 22, 2009.
International Search Report and Written Opinion for App. Ser. No. PCT/US2007/081473, mailed Nov. 7, 2008.
Iyer et al., "Targeting TGFbeta signaling for cancer therapy," Cancer Biol. Ther., 4(3):261-266 (2005).
Jakobovits et al., Ann. NY Acad. Sci., 764:525-535 (1995).
Jalkanen et al., "Cell surface proteoglycan of mouse mammary epithelial cells is shed by cleavage of its matrix-binding ectodomain from its membrane-associated domain," J. Cell Biol., 105(6 Pt 2):3087-3096 (1987).
Jalkanen et al., "Heparan sulfate proteoglycans from mouse mammary epithelial cells: localization on the cell surface with a monoclonal antibody," J. Cell Biol., 101(3):976-985 (1985).
Janes et al., "Switch from alphavbeta5 to alphavbeta6 integrin expression protects squamous cell carcinomas from anoikis," J. Cell Biol., 166(3):419-431 (2004).
Ji et al., J. Viral Hepat., 4:167-173 (1997).
Juliano, "Signal transduction by integrins and its role in the regulation of tumor growth," Cancer Metastasis Rev., 13:25-30 (1994).

(56) References Cited

OTHER PUBLICATIONS

Kaminski et al., "Global analysis of gene expression in pulmonary fibrosis reveals distinct programs regulating lung inflammation and fibrosis," Proc. Natl. Acad. Sci. USA, 97(4):1778-1783 (2000).
Kaneda et al., Ann. NY Acad. Sci., 811:299-310 (1997).
Kasuga et al., "Effects of anti-TGF-beta type II receptor antibody on experimental glomerulonephritis," Kidney Int., 60 (5):1745-1755 (2001).
Kennedy et al., Clin. Chim. Acta, 70:1-31 (1976).
Khalil, "TGF-beta: from latent to active," Microbes Infect., 1(15):1255-1263 (1999).
Klimka et al., "Human anti-CD30 recombinant antibodies by guided phage antibody selection using cell panning," Br. J. Cancer, 83:252-260 (2000).
Knight et al., Am. J. Pathol., 161(3):771-779 (2002).
Koivisto et al., "Different integrins mediate cell spreading, haptotaxis and lateral migration of HaCaT keratinocytes on fibronectin," Cell Adhes. Commun., 7:245-257 (1999).
Kolbinger et al., Protein Eng., 8:971-980 (1993).
Konigshoff et al., "TGF-beta signaling in COPD: deciphering genetic and cellular susceptibilities for future therapeutic regimen," Swiss Med. Wkly., 139(39-40):554-563 (2009).
Kunicki et al., J. Biol. Chem., 270(28):16660-16665 (1995).
Kunicki et al., J. Biol. Chem., 272(7):4103-4107 (1997).
Kuntz, "Structure-based strategies for drug design and discovery," Science, 257:1078-1082 (1992).
Kussie et al., "A single engineered amino acid substitution changes antibody fine specificity," *J. Immunol.,* 152(1):146-52 (1994).
Leask et al.. "TGF-beta signaling and the fibrotic response," FASEB J., 18(7):816-827 (2004).
Leone et al., "A blocking monoclonal antibody to integrin alphavbeta6 inhibits tumor growth in a human pharyngeal 3 xenograft model," Proceedings of the Annual Meeting of the American Association for Cancer Research, vol. 44 (2003) XP008070338.
Li et al., "ALPHAVBETA6-Fyn signaling promotes oral cancer progression," J. Biol. Chem., 278(43):41646-41653 (2003).
Li et al., "Transforming growth factor-beta regulation of immune responses," Annu. Rev. Immunol., 24:99-146 (2006).
Liu et al., "Fine mapping of the antigen-antibody interaction of scFv215, a recombinant antibody inhibiting RNA polymerase II from *Drosophila melanogaster*," J. Mol. Recognit., 12(2):103-11 (1999).
Massague, "TGF-beta signal transduction," Annu. Rev. Biochem., 67:753-791 (1998).
Ludbrook et al., Biochem. J., 369(Pt 2):311-318 (2003).
Ma et al., "Accelerated fibrosis and collagen deposition develop in the renal interstitium of angiotensin type 2 receptor null mutant mice during ureteral obstruction," Kidney Int., 53(4):937-944 (1998).
Ma et al., "Transforming growth factor-beta-dependent and -independent pathways of induction of tubulointerstitial fibrosis in beta6(-/-) mice," Am. J. Pathol., 163(4):1261-1273 (2003).
Ma LJ. et al., J. Am. Soc. Nephrol., 12:819A (2001).
Ma, LJ. et al., Lab Investigation, 81:189A (2001).
Miller et al., "Ligand binding to proteins: the binding landscape model," Protein Sci., 6:2166-2179 (1997).
Miller et al., "MCF1ODCIS.com xenograft model of human comedo ductal carcinoma in situ," J. Natl. Cancer Inst., 92(14):1185-1186 (2000).
Miner et al., "Molecular and functional defects in kidneys of mice lacking collagen alpha 3(IV): implications for Alport syndrome," J. Cell Biol., 135(5):1403-1413 (1996).
Mitjans et al., J. Cell Sci., 108(Pt 8):2825-2838 (1995).
Morgan et al., "The integrin cytoplasmic-tall motif EKQKVDLSTDC is sufficient to promote tumor cell invasion mediated by matrix metalloproteinase (MMP)-2 or MMP-9," J. Biol. Chem., 279(25):26533-26539 (2004).
Morris et al., "Loss of integrin alpha(v)beta6-mediated TGF-beta activation causes Mmp12—dependent emphysema," Nature, 422(6928):169-173 (2003).
Movsas et al., "Pulmonary radiation injury," Chest, 111(4):1061-1076 (1997).
Mu et al., "The integrin alpha(v)beta8 mediates epithelial homeostasis through MT1-MMP-dependent activation of TGF-beta1," J. Cell Biol., 157(3):493-507 (2002).
Munger et al., "Latent transforming growth factor-beta: structural features and mechanisms of activation," Kidney Int., 51:1376-1382 (1997).
Munger et al., Cell, 96(3):319-328 (1999).
Muraoka et al., "Blockade of TGF-beta inhibits mammary tumor cell viability, migration, and metastases," J. Clin. Invest., 109(12):1551-1559 (2002).
Murayama et al., Antisense Nucleic Acid Drug Dev., 7:109-114 (1997).
Neuberger et al., Nature, 312:604-608 (1984).
Neurohr et al., "Activation of Transforming Growth Factor-beta by the Integrin aiphaVbeta8 Delays Epithelial Wound Closure," Am. J. Respir. Cell Mol. Biol., 35:252-259 (2006).
Niidome et al., J. Biol. Chem., 272:15307-15312 (1997).
Niu et al. "The alphaVbeta6 integrin regulates its own expression with cell crowding: implications for tumour progression," Int. J. Cancer, 92(1):40-48 (2001).
O'Brien et al., "Humanization of monoclonal antibodies by CDR grafting," Methods Mol. Biol., 207:81-100 (2003).
Oft et al., Curr. Biol., 8(23):1243-1252 (1998).
Ohta, "Gene polymorphism in airway remodeling of asthma," Tokyo University School of Medicine, 20-26 (2004) (with English translation).
Orlandi et al., "Cloning immunoglobulin variable domains for expression by the polymerase chain reaction," Proc. Natl. Acad. Sci. USA, 86(10):3833-3837 (1989).
Palmer et al., Chest, 69:307-309 (1976).
Pasqualini et al., J. Cell. Biol., 130: 1189-1196 (1995).
Pierschbacher et al., J. Cell. Biochem., 56:150-154 (1994).
Pittet et al., "TGF-beta is a critical mediator of acute lung injury," J. Clin. Invest., 107(12):1537-1544 (2001).
PLoS Medicine, Apr. 2006, vol. 3, Issue 4, p. 0420.
Pons et al., "Decreased macrophage release of TGF-beta and TIMP-1 in chronic obstructive pulmonary disease," Eur. Respir. J., 26:60-66 (2005).
Prieto et al., "Multiple integrins mediate cell attachment to cytotactin/tenascin," Proc. Natl. Acad. Sci. USA, 90(21):10154-10158 (1993).
Puthawala et al , "Inhibition of integrin alpha(v)beta6, an activator of latent transforming growth factor-beta, prevents radiation induced lung fibrosis," Am. J. Respir. Crit. Care Med., 177(1):82-90 (2008).
Queen et al., "A humanized antibody that binds to the interleukin 2 receptor," Proc. Natl. Acad. Sci. USA, 86(24):10029-10033 (1989).
Raguse et al., "Cilengitide (EMD 121974) arrests the growth of a heavily pretreated highly vascularized head and neck tumour," Oral Oncol., 40(2):228-230 (2004).
Regezi et al., "Tenascin and beta 6 integrin are overexpressed in floor of mouth in situ carcinomas and invasive squamous cell carcinomas," Oral Oncol., 38:332-336 (2002).
Ritter et al., "Serological analysis for human anti-human antibody responses in colon cancer patitents treated with repeated doses of humanized monoclonal antibody A33," *Cancer Research,* 61:6851-6859 (2001).
Roberts et al., "Transforming growth factor type beta: rapid induction of fibrosis and angiogenesis in vivo and stimulation of collagen formation in vitro," Proc. Natl. Acad. Sci. USA, 83(12):4167-4171 (1986).
Rudikoff et al., "Single amino acid substitution altering antigen-binding specificity," Proc. Natl. Acad. Sci. USA, 79(6):1979-1983 (1982).
Ruoslahti et al., "Anchorage dependence, integrins, and apoptosis," Cell, 77:477-478 (1994).
Ruoslahti et al., "Integrins and tumor cell dissemination," Cancer Cells, 1:119-126 (1989).
Ruoslahti, "Integrins," J. Clin. Invest., 87(1):1-5 (1991).
Ruoslahti, Ann. Rev. Cell. Dev. Biol., 12:697-715 (1996).
Sampson et al., "Global gene expression analysis reveals a role for the alpha 1 integrin in renal pathogenesis," J. Biol. Chem., 276(36):34182-34188 (2001).

(56) References Cited

OTHER PUBLICATIONS

Schildbach et al., "Heavy chain position 50 is a determinant of affinity and specificity for the anti-digoxin antibody 26-10," *J. Biol. Chem.,* 268(29):21739-47 (1993).
Schildbach et al., "Contribution of a single heavy chain residue to specificity of an anti-digoxin monoclonal antibody," Protein Sci., 3(5):737-49 (1994).
Schuurs et al., Clin. Chim. Acta, 81:1-40 (1977).
Selman, "Idiopathic pulmonary fibrosis challenges for the future," Chest, 120(1):8-10 (2001).
Shapiro, "The pathophysiology of COPD: What goes wrong and why?," Proceedings Adv. Stud. Med., 3(2B):S91-S98 (2003).
Sheppard et al., "Integrin-mediated activation of transforming growth factor-beta(1) in pulmonary fibrosis," Chest, 120(1 Suppl):49S-53S (2001).
Sheppard et al., "Transforming growth factor beta: a central modulator of pulmonary and airway inflammation and fibrosis," Proc. Am. Thorac. Soc., 3(5):413-417 (2006).
Sheppard et al., J. Biol. Chem., 265(20):11502-11507 (1990).
Sheppard, Am. J. Respir. Cell Mol. Biol., 19(3):349-351 (1998).
Sheppard. "Functions of pulmonary epithelial integrins: from development to disease," Physiol. Rev., 83(3):673-686 (2003).
Shihab et al., "Transforming growth factor-beta and matrix protein expression in acute and chronic rejection of human renal allografts," J. Am. Soc. Nephrol., 6(2):286-294 (1995).
Sime et al., "Adenovector-mediated gene transfer of active transforming growth factor-beta 1 induces prolonged severe fibrosis in rat lung," J. Clin. Invest., 100(4):768-776 (1997).
Sleijfer, "Bleomycin-induced pneumonitis," Chest, 120(2):617-624 (2001).
Smith et al., J. Biol. Chem., 269:32788-32795 (1994).
Tatler et al., "Integrin αvβ5-mediated TGF-β activation by airway smooth muscle cells in asthma," J. Immunol., 187:6094-6107 (2011).
Thomas et al., "AlphaVbeta6 integrin promotes invasion of squamous carcinoma cells through up-regulation of matrix metalloproteinase-9," Int. J. Cancer, 92(5):641-650 (2001).
Thomas et al., "Binding of TGF-betal latency-associated peptide (LAP) to alpha(v)beta6 integrin modulates behaviour of squamous carcinoma cells," Br. J. Cancer 87(8):859-867 (2002).
Thomas et al., "Expression of the alphavbeta6 integrin promotes migration and invasion in squamous carcinoma cells," J. Invest. Dermatol., 117(1):67-73 (2001).
Thomas et al., "TGF-beta directly targets cytotoxic T cell functions during tumor evasion of immune surveillance," Cancer Cell, 8:369-380 (2005).
Torra et al., "Collagen type IV (alpha3-alpha4) nephropathy: from isolated haematuria to renal failure," Nephrol. Dial Transplant., 19(10):2429-2432 (2004).
Trevillian et al., "alpha(v)beta(6) Integrin expression in diseased and transplanted kidneys," Kidney Int., 66:1423-1433 (2004).
Tsushima et al., Inter. Med., 48:621-630 (2009).
Turner-Warwick et al., "Cryptogenic fibrosing alveolitis: response to corticosteroid treatment and its effect on survival," Thorax, 35(8):593-599 (1980).
Vajdos et al., "Comprehensive functional maps of the antigen-binding site of an anti-ErbB2 antibody obtained with shotgun scanning mutagenesis," J. Mol. Biol., 320(2):415-428 (2002).
Van Den Broek and Van De Vijver, "Assesment of problems in diagnostic and research immunohistochemistry associate with epitope instability in stored paraffin sections," *Appl. Immunohistochem., Mol. Morphol.,* 8(4):316-21 (2000).
Varga et al., "Transforming growth factor beta (TGF beta) causes a persistent increase in steady-state amounts of type 33 I and type III collagen and fibronectin mRNAs in normal human dermal fibroblasts," Biochem. J., 247(3):597-604 (1987).
Vidal et al., CR Acad. Sci. III, 320:279-287 (1997).
Wada et al., "Cloning of mouse integrin alphaV cDNA and role of the alphaV-related matrix receptors in metanephric development," J. Cell Biol., 132(6):1161-1176 (1996).
Wahl, "Transforming growth factor beta: the good, the bad, and the ugly," J. Exp. Med., 180(5):1587-1590 (1994).
Walker et al., "Valvular myofibroblast activation by transforming growth factor-beta: implications for pathological extracellular matrix remodeling in heart valve disease," Circ. Res., 95(3):253-260 (2004).
Wang et al., "Progressive adriamycin nephropathy in mice: sequence of histologic and immunohistochemical events," Kidney Int., 58(4):1797-1804 (2000).
Wang et al., "Reduction of bleomycin induced lung fibrosis by transforming growth factor beta soluble receptor in hamsters," Thorax, 54(9):805-812 (1999).
Weinacker et al., "Role of the integrin alpha v beta 6 in cell attachment to fibronectin. Heterologous expression of intact and secreted forms of the receptor," J. Biol. Chem., 269(9):6940-6948 (1994).
Weinacker et al., J. Cell Biol., 269:1-9 (1994).
Wu et al., "An analysis of the sequences of the variable regions of Bence Jones proteins and myeloma light chains and their implications for antibody complementarity," J. Exp. Med., 132(2):211-250 (1970).
Wu et al., Proc. Natl. Acad. Sci. USA, 95(11 ):6037-6042 (1998).
Wyckoff et al., "A critical step in metastasis: in vivo analysis of intravasation at the primary tumor," Cancer Res., 60 (9):2504-2511 (2000).
Xiang et al., "Study of B72.3 combining sites by molecular modeling and site-directed mutagenesis," *Protein Eng.,* 13(5):339-44 (2000).
Xiao et al., Brain Res., 756:76-83 (1997).
Yamamoto et al., "Expression of transforming growth factor beta is elevated in human and experimental diabetic nephropathy," Proc. Natl. Acad. Sci. USA, 90(5):1814-1818 (1993).
Yang et al., "Lifetime exposure to a soluble TGF-beta antagonist protects mice against metastasis without adverse side effects," J. Clin. Invest., 109(12):1607-1615 (2002).
Yokosaki et al., "Differential effects of the integrins alpha9beta1, alphavbeta3, and alphavbeta6 on cell proliferative responses to tenascin. Roles of the beta subunit extracellular and cytoplasmic domains," J. Biol. Chem., 271(39):24144-24150 (1996).
Zambruno et al., "Transforming growth factor-beta 1 modulates beta 1 and beta 5 integrin receptors and induces the de novo expression of the alpha v beta 6 heterodimer in normal human keratinocytes: implications for wound healing," J. Cell Biol., 129(3):853-865 (1995).
Zhang et al., "Monoclonal antibody recognizing a carcinoembryonic antigen epitope differentially expressed in human colonie carcinoma versus normal adult colon tissues," *Cancer Research*, 49:5766-5773 (1989).
Zisman et al., "Cyclophosphamide in the treatment of idiopathic pulmonary fibrosis: a prospective study in patients who failed to respond to corticosteroids," Chest, 117(6):1619-1626 (2000).
Ziyadeh et al., "Long-term prevention of renal insufficiency, excess matrix gene expression, and glomerular mesangial matrix expansion by treatment with monoclonal antitransforming growth factor-beta antibody in db/db diabetic mice," Proc. Natl. Acad. Sci. USA, 97(14):8015-8020 (2000).
International Search Report and Written Opinion for International App. Ser. No. PCT/US2013/032082, mailed Jul. 8, 2013, 17 pages.
Xu et al., "Lysophosphatidic Acid Induces avB6 ntegrin-Mediated TGF-B Activation via the LPA2 Receptor and the Small G Protein Gaq," *American Journal of Pathology,* Apr. 2009, 174:1264-1279.
William E. Paul, ed., 3rd ed. 1993, Fundamental Immunology, p. 242.*
Kaiser (Science, 2006, 313, 1370).*
Bodey et al, 2001, Expert Opinion Biological Therapy, 1(4): 603-617.*
Bodey et al, 2000, Anticancer Res, 20: 2665-2676.*
Mellman I, 2006, The Scientist, 20(1): 47-56.*
Lee et al, 1999, J Immunol, 163: 6292-6300.*
Stedman's medical dictionary, 25th ed, 1990, p. 1652-1653.*
Redman, 2005, J Oral pathol Med, 34(1): 23-9.*
Xue et al, 2001, Biochem Biophys Res Comm, 288: 610-618.*
Sipos et al, 2004, Histopathology, 45: 226-236.*
Iacobuzio-Donahue et al, 2004, Clin Cancer Res, 10: 1597-1604.*
Watanabe et al, 1997, J Natl Cancer Institute, 89(7): 512-8, abstract only.*

(56) References Cited

OTHER PUBLICATIONS

European Patent Offce, Communication enclosing European search report, EP application No. 07810296.9, dated Apr. 8, 2010 (5 pages).
Weinreb, P H et al., "Function-Blocking Integrin Alphavbeta6 Monoclonal Antibodies: Distinct Ligand-Mimetic and Nonligand-Mimetic Classes", Journal of Biological Chemistry, American Society for Biochemistry and Molecular Biology, Inc., US, vol. 279, No. 17, Feb. 11, 2004, pp. 17875-17887, XP002405412, ISSN 0021-9258.
Kracklauer, M P et al, "TGF[beta]1 Signaling Via [alpha]V[beta]6 Integrin", Molecular Cancer 20030807 GB , vol. 2, Aug. 7, 2003, XP002573605, ISSN: 1476-4598.
Subramanian et al., "Targeting Endogenous Transforming Growth Factor—Receptor Signaling in SMAD4-Deficient Human Pancreatic Carcinoma Cells Inhibits Their Invasive Phenotype" Cancer Res., vol. 64, No. 15, Aug. 1, 2004, pp. 5200-5211, XP08102563.
Thomas et al., "Alpha v beta 6 Integrin in Wound Heading and Cancer of the Oral Cavity", J. Oral Pathol. Med., vol. 35, No. 1, Jan. 2006, pp. 1-10, XP008102570.

* cited by examiner

DCIS

BrCa 19

Invasive Carcinoma

BrCa 23

Matched cases
Pancreatic Adenocarcinoma, *Ductal*

Matched cases
Pancreatic Carcinoma pancreas sections pancreas sections

αvβ6 +/- heterogeneous pancreas sections

αvβ6 +/- heterogeneous

FIGURE 14

Results

| | | axb3 | smad4 | comments |
|---|---|---|---|---|
| 1 | 4107 | neg | pos | |
| 2 | 41519 | neg | pos | |
| 3 | 41522 | neg | pos | |
| 4 | 41462 | neg | pos | |
| 5 | 41463 | weak (neg) | pos | consider neg: axb3 expression is MUCH weaker than any other axb3 typically observed on axb3 positive tumors |
| 6 | 41479 | neg | pos | |
| 7 | 41475 | neg | pos | this is in the prominent tumor field (some axb3 pos glandular structure, is smad4 pos as well) |
| 8 | 41477 | pos | neg | |
| 9 | 41470 | pos | neg | |
| 10 | 41515 | pos | neg | |
| 11 | 41523 | pos | pos | |
| | heterogeneous | | | |
| 12 | 4104 | pos | neg | |
| | | neg | pos | |
| 13 | 41513 | pos | neg | |
| | | neg | pos | |
| 14 | 41517 | pos | neg | |
| | | neg | pos | |

Figure 15
| Cell Line | SMAD4 Protein | avb6 Protein |
|---|---|---|
| Aspc-1 | - | + |
| BxPC-3 | - | + |
| Capan-2 | - | + |
| CFPac-1 | - | + |
| Hpaf-II | - | + |
| Su86.86 | - | + |
| Capan-1 | faint | + |
| MiaPaCa | ++ | - |
| Panc04.03 | + | + |
| Panc-1 | ++ | - |
| Sw1990 | + | + |
| Hs766T | - | - |
| L3.6pl | + | + |
| Panc02.13 | - | + |
| Panc08.04 | - | + |
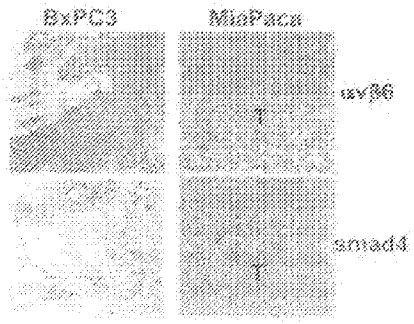
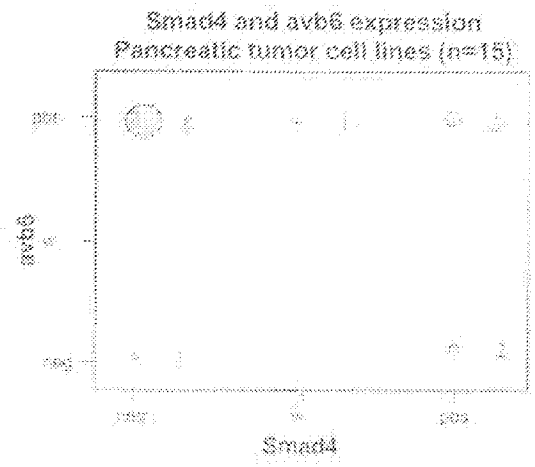

Change in body weight in response to treatment with αvβ6 mAb 3G9 and Doxorubicin, as single agents or in combination Vs vehicle control

| | | |
|---|---|---|
| 3G9 | d41-54: | $p < 0.01$ |
| Gemcitabine | d29-54: | $p < 0.01$ |
| TGF beta RII/Fc: | d29-47: | $p < 0.01$ |

3G9, Gem combo vs 3G9 d29-54: $p < 0.01$
3G9, Gem combo vs gem d32-54: $p < 0.01$ TGF beta RII/Fc Gem combo vs TGF beta RII/Fc : d41-54 $p < 0.05$
TGF beta RII/Fc Gem combo vs Gem: d47-54 $p < 0.05$ 3G9 vs vehilce: NS
Gemcitabine vs vehicle: P<0.05
combo vs vehicle: NS
combo vs 3G9: NS
combo vs Gem: P<0.05*

* growth enhancement compared to Gem alone

SW1990

| Cell Line | source | xenograft | response in vivo to 3G9 and gemzar | growth effect and p-values | avb6 protein | SMAD4 Protein | smad4 gene | Kras gene (BI) | P53 Sanger/ BIIE | TGFb prolif. responsive (in vitro) |
|---|---|---|---|---|---|---|---|---|---|---|
| BxPC-3 | prim Tumor | s.c. BIIB | 3G9 alone ns effect<br>3G9 + gemzar synergy | 20% inh. ns<br>60% inh. p<0.01 | + | - | HD | wt | Y220C/472P;<br>R248W;C993T | inh (~25%) |
| Su86.86 | liver met | s.c. BIIB | 3G9 alone ns effect<br>3G9 + gemzar synergy | ns<br>90% inh. p<0.01 | + | + | wt | G12D | nd/<br>WT | inh (15%) |
| Capan-2 | prim Tumor | s.c. BIIB | 3G9 alone efficacious<br>3G9 + gemzar synergy | 35% inh. p<0.01<br>70% inh. p<0.01 | + | - | wt | G12V | nd/<br>nd | inh (~20%) |
| Panc04.03 | prim Tumor | s.c. BIIB | 3G9 alone efficacious<br>3G9 + gemzar synergy | 30% inh. p<0.05<br>75% inh. p<0.05 | + | + | wt | G12D | n.d/<br>G245S;<br>G984A | inh (~35%) |
| Aspc-1 | ascites | s.c. orthotopic Parenqi | 3G9 alone ns effect<br>3G9 + gemzar efficacious | 27% inh. p<0.05<br>30% inh. p<0.05 | + | - | mt (exon2 arg100Thr) | G12D | nd/<br>T851del | n.d |
| Capan-1 | liver met | s.c. BIIB | ns effect | ns effect | + | + | G12V | A138V/<br>A159V;C727T | inh (25%) | inh (25%) |
| Swt990 | spleen met | s.c. BIIB | 3G9 alone stim<br>3G9 + gemzar no effect | 50% stim. p<0.01<br>ns | + | + | wt | G12D | WT/<br>WT | stim (30%) |

FIGURE 35

| Cell Line | source | xenograft | response in vivo to 3G9 and gemzar | growth effect and p-values | avb6 protein | SMAD4 Protein | smad4 gene ( | Kras gene (BI | P53 Sanger/ BIIE | TGFβ prolif. responsive (*in vitro*) |
|---|---|---|---|---|---|---|---|---|---|---|
| BxPC-3 | prim Tumo | s.c. BIB | 3G9 alone ns effect<br>3G9 + gemzar synergy | 20% inh, ns<br>60% inh, p<0.01 | + | - | HD | wt | Y220C/<br>R73P;<br>R248W C993T | inh (~25%) |
| Su86.86 | liver met | s.c. BIB | 3G9 alone ns effect<br>3G9 + gemzar synergy | ns<br>90% inh, p<0.01 | + | - | wt | G12D | wt/<br>wt | inh (15%) |
| Capan-2 | prim Tumo | s.c. BIB | 3G9 alone efficacious<br>3G9 + gemzar synergy | 35% inh, p<0.01<br>70% inh, p<0.01 | + | - | wt | G12V | nd/<br>nd | inh (~20%) |
| Panc04.03 | prim Tumo. | s.c. BIB | 3G9 alone efficacious<br>3G9 + gemzar synergy | 30% inh, p<0.05<br>75% inh, p<0.05 | + | + | wt | G12D | n.d/<br>G245S;G984A | inh (~35%) |
| Aspc-1 | ascites | s.c. Aspc emgi | 3G9 alone ns effect<br>3G9 + gemzar efficacious | 27% inh, p=0.06<br>30% inh, p<0.05 | + | - | mt (exon2 arg100thr) | G12D | nd/<br>T881del | n.d |
| Capan-1 | liver met | s.c. BIB | ns effect | ns effect | + | + | mt (exon8 ser343stop) | G12V | A159V/<br>A159V;C727T | inh (25%) |
| Sw1990 | spleen me. | s.c. BIB | 3G9 alone stim.<br>3G9 + gemzar no effect | 50% stim, p<0.01<br>ns | + | + | wt | G12D | WT/<br>WT | stim (30%) |

Figure 36

Response of the subcutaneously implanted Detroit 562, human pharynx carcinoma cell Line to avβ6 mAb therapy with 3G9.

Study TS #155

Response of the subcutaneously implanted Detroit 562, human pharynx carcinoma cell line to avb6 mAb therapy with murine or humanized 3G9, 8G9 and 4B4

TS#222

Response of the subcutaneously implanted Detroit 562, human pharynx carcinoma cell line to avb6 mAb therapy with murine or humanized 3G9, 8G9 and 4B4

TS#222

Response of the subcutaneously implanted Detroit 362, human pharynx carcinoma cell line to avb6 mAb therapy with murine or humanized 3G9, 8G9 and 4B4

TS#222

COMPOSITIONS AND METHODS FOR INHIBITING GROWTH OF SMAD4-DEFICIENT CANCERS

Matter enclosed in heavy brackets [ ] appears in the original patent but forms no part of this reissue specification; matter printed in italics indicates the additions made by reissue.

CROSS-REFERENCE TO RELATED APPLICATIONS

This application claims the benefit of U.S. Provisional Application No. 60/819,359, filed Jul. 10, 2006, which is incorporated herein by reference in its entirety.

BACKGROUND OF THE INVENTION

1. Field of the Invention

The present invention is in the fields of cell biology, immunology and oncology. The invention relates to the discovery that there is a relationship between the expression levels of the tumor suppressor gene smad4 (also known as dpc4) and integrin $\alpha_v\beta_6$, and the responsiveness of patient populations to $\alpha_v\beta_6$-active compounds and compositions (e.g., antibodies and other ligands that bind $\alpha_{v\beta 6}$), particularly in cancer cells from such patient populations, more particularly on carcinomas such as pancreatic carcinomas. The invention thus provides methods for determining the responsiveness of tumor cells (particularly those from pancreatic tumors) to such $\alpha_v\beta_6$-active compounds and compositions by examining the expression of $\alpha_v\beta_6$ and smad4 by the tumor cells, as well as methods of diagnosis and treatment/prevention of tumor progression using ligands, including antibodies and small molecule drugs, that bind to integrin $\alpha_v\beta_6$ on the surfaces of tumor cells and/or that block one or more components of the TGF-β pathway, particularly in smad4-deficient tumor cells.

2. Related Art

Integrins are cell surface glycoprotein receptors which bind extracellular matrix proteins and mediate cell-cell and cell-extracellular matrix interactions (generally referred to as cell adhesion events) (Ruoslahti, E., J Clin. Invest. 87:1-5 (1991); Hynes, R. O., Cell 69:11-25 (1992)). These receptors are composed of noncovalently associated alpha (α) and beta (β) chains which combine to give a variety of heterodimeric proteins with distinct cellular and adhesive specificities (Albeda, S. M., Lab. Invest. 68:4-14 (1993)). Recent studies have implicated certain integrins in the regulation of a variety of cellular processes including cellular adhesion, migration, invasion, differentiation, proliferation, apoptosis and gene expression (Albedo, S. M., Lab. Invest. 68:4-14 (1993); Juliano, R., Cancer Met. Rev. 13:25-30 (1994); Ruoslahti, E. and Reed, J. C., Cell 77:477-478 (1994); and Ruoslahti, E. and Giancotti, F. G., Cancer Cells 1:119-126 (1989); Plow, Haas et al. 2000; van der Flier and Sonnenberg 2001).

The $\alpha_v\beta_6$ receptor is one member of a family of integrins that are expressed as cell surface heterodimeric proteins (Busk, M. et al., J. Biol. Chem. 267(9):5790-5796 (1992)). While the $\alpha_v$ subunit can form a heterodimer with a variety of β subunits ($\beta_1$, $\beta_3$, $\beta_5$, $\beta_6$ and $\beta_8$), the $\beta_6$ subunit can only be expressed as a heterodimer with the $\alpha_v$ subunit. The $\alpha_v\beta_6$ integrin is known to be a fibronectin-, latency associated peptide (LAP)- and tenascin C-binding cell surface receptor, interacting with the extracellular matrix through the RGD tripeptide binding sites thereon (Busk, M. et al., J. Biol. Chem. 267:5790-5796 (1992); Weinacker, A. et al., J. Biol. Chem. 269:6940-6948 (1994); Prieto, A. L. et al., Proc. Natl. Acad. Sci. USA 90:10154-10158 (1993)). Although the $\alpha_v\beta_6$ integrin was first identified and sequenced more than 10 years ago, the biological significance of $\alpha_v\beta_6$, especially in disease, is still under investigation. The expression of $\alpha_v\beta_6$ is restricted to epithelial cells where it is expressed at relatively low levels in healthy tissue and significantly upregulated during development, injury, and wound healing (Breuss, J. M. et al., J. Histochem. Cytochem. 41:1521-1527 (1993); Breuss, J. M. et al., J Cell Sci. 108:2241-2251 (1995); Koivisto, L. et al., Cell Adhes. Communic. 7:245-257 (1999); Zambruno, G. et al., J. Cell Biol. 129(3):853-865 (1995); Hakkinen, L. et al., J. Histochem. Cytochem. 48(6):985-998 (2000)). An increasing number of recent reports demonstrate that $\alpha_v\beta_6$ is upregulated on cancers of epithelial origin, including colon carcinoma (Niu, J. et al, Int. J. Cancer 92:40-48 (2001); Bates, R. C. et al., J. Clin. Invest. 115:339-347 (2005)), ovarian cancer (Ahmed, N. et al., J. Cell. Biochem. 84:675-686 (2002); Ahmed, N. et al., J. Histochem. Cytochem. 50:1371-1379 (2002); Ahmed, N. et al., Carcinogen. 23:237-244 (2002)), squamous cell carcinoma (Koivisto, L. et al., Exp. Cell Res. 255:10-17 (2000); Xue, H. et al., Biochem. Biophys. Res. Comm. 288:610-618 (2001); Thomas, G. J. et al., J. Invest. Derinatol. 117:67-73 (2001); Thomas, G. J. et al., Int. J. Cancer 92:641-650 (2001); Ramos, D. M. et al., Matrix Biol. 21:297-307 (2002); (Agrez, M. et al., Br. J. Cancer 81:90-97 (1999); Hamidi, S. et al., Br. J. Cancer 82(8):1433-1440 (2000); Kawashima, A. et al., Pathol. Res. Pract. 99(2):57-64 (2003)), and breast cancer (Arihiro, K. et al., Breast Cancer 7:19-26 (2000)). It has also been reported that the cc subunit may be involved in tumor metastasis, and that blocking this subunit consequently may prevent metastasis (for review, see Imhof, B. A. et al., in: "Attempts to Understand Metastasis Formation I," U. Günthert and W. Birchmeier, eds., Berlin: Springer-Verlag, pp. 195-203 (1996)).

The $\alpha_v\beta_6$ integrin may have multiple regulatory functions in tumor cell biology. Recent studies have demonstrated that the extracellular and cytoplasmic domains of the $\beta_6$ subunit mediate different cellular activities. The extracellular and transmembrane domains have been shown to mediate TGF-β activation and adhesion (Sheppard, D., Cancer and Metastasis Rev. 24:395-402 (2005); Munger, J. S. et al., Cell 96:319-328 (1999)). The cytoplasmic domain of the $\beta_6$ subunit contains a unique 11-amino acid sequence that is important in mediating $\alpha_v\beta_6$ regulated cell proliferation, MMP production, migration, and pro-survival (Li, X. et al., J. Biol. Chem. 278(43):41646-41653 (2003); Thomas, G. J. et al., J Invest. Derm. 117(1):67-73 (2001); Thomas, G. J. et al., Br. J. Cancer 87(8):859-867 (2002); Janes, S. M. and Watt, F. M., J. Cell Biol 166(3):419-431 (2004)). The $\beta_6$ subunit has been cloned, expressed and purified (Sheppard et al., U.S. Pat. No. 6,787,322 B2, the disclosure of which is incorporated herein by reference in its entirety), and function-blocking antibodies that selectively bind to the $\alpha_v\beta_6$ integrin have been reported (Weinreb et al., J. Biol. Chem. 279:17875-17877 (2004), the disclosure of which is incorporated herein by reference in its entirety). Antagonists of ($\alpha_v\beta_6$ (including certain monoclonal antibodies) have also been suggested as possible treatments for certain forms of acute lung injury and fibrosis (see U.S. Pat. No. 6,692,741 B2 and WO 99/07405, the disclosures of which are incorporated herein by reference in their entireties).

$\alpha_v\beta_6$ can bind to several ligands including fibronectin, tenascin, and the latency associated peptide-1 and -3 (LAP1 and LAP3), the N-terminal 278 amino acids of the latent precursor form of TGF-β1 through a direct interaction with an arginine-glycine-aspartate ("RGD") motif (Busk. M. et al., J.

Biol. Chew. 267(9):5790-5796 (1992); Yokosaki, Y. et al., J. Biol. Chem. 271(39):24144-24150 (1996); Huang, X. Z. et al., J. Cell. Sci. 111:2189-2195 (1998); Munger, J. S. et al., Cell 96:319-328 (1999)). The TGF-β cytokine is synthesized as a latent complex which has the N-terminal LAP non-covalently associated with the mature active C-terminal TGF-β cytokine. The latent TGF-β complex cannot bind to its cognate receptor and thus is not biologically active until converted to an active form (Barcellos-Hoff, M. H., J. Mamm. Gland Biol. 1(4):353-363 (1996); Gleizes, P. E. et al., Stem Cells 15(3):190-197 (1997); Munger, J. S. et al., Kid. Int 51:1376-1382 (1997); Khalil, N., Microbes Infect. 1(15): 1255-1263 (1999)). $\alpha_v\beta_6$ binding to LAP1 or LAP3 leads to activation of the latent precursor form of TGF-β1 and TGF-β3 (Munger, J. S. et al., Cell 96:319-328 (1999)), proposed as a result of a conformational change in the latent complex allowing TGF-β to bind to its receptor. Thus, upregulated expression of $\alpha_v\beta_6$ can lead to local activation of TGF-β which in turn can activate a cascade of downstream events.

The TGF-β1 cytokine is a pleiotropic growth factor that regulates cell proliferation, differentiation, and immune responses (Wahl, S. M., J. Exp. Med. 180:1587-1590 (1994); Massague, J., Annu. Rev. Biochem. 67:753-791 (1998); Chen, W. and Wahl, S. M., TGF-β: Receptors, Signaling Pathways and Autoimmunity, Basel: Karger, pp. 62-91 (2002); Thomas, D. A. and Massague, J., Cancer Cell 8:369-380 (2005)). The role that TGF-β1 plays in cancer is two-sided. TGF-β is recognized to tumor suppressor and growth inhibitory activity yet, many tumors evolve a resistance to growth suppressive activities of TGF-β1 (Yingling, J. M. et al., Nature Rev. Drug Discov. 3(12):1011-1022 (2004); Akhurst, R. J. et al., Trends Cell Biol. 11(11):S44-S51 (2001); Balmain, A. and Akhurst, R. J., Nature 428(6980): 271-272 (2004)). In established tumors, TGF-β1 expression and activity has been implicated in promoting tumor survival, progression, and metastases (Akhurst, R. J. et al., Trends Cell Biol. 11(11): S44-S51 (2001); Muraoka, R. S. et al., J. Clin. Invest. 109 (12):1551 (2002); Yang, Y. A. et al., J. Clin. Invest. 109(12): 1607-1615 (2002)). This is postulated to be mediated by both autocrine and paracrine effects in the local tumor-stromal environment including the effects of TGF-β on immune surveillance, angiogenesis, and increased tumor interstitial pressure. Several studies have now shown the anti-tumor and anti-metastatic effects of inhibiting TGF-β1 (Akhurst, R. J., J. Clin. Invest. 109(12):1533-1536 (2002); Muraoka, R. S. et al., J. Clin. Invest. 109(12):1551 (2002); Yingling, J. M. et al., Nat. Rev. Drug Discov. 3(12):1011-1022 (2004); Yang, Y. A. et al., J. Clin. Invest. 109(12):1607-1615 (2002); Halder, S. K. et al., Neoplasia 7(5):509-521 (2005); Tyer, S. et al., Cancer Biol. Ther. 4(3):261-266 (2005)).

Increased expression of $\alpha_v\beta_6$ on tumors, particularly at the tumor-stromal interface, may reflect a unique mechanism for local activation of TGF-β1 and the ability to promote tumor survival, invasion, and metastasis. The high level of expression in human metastases infers a potential role for $\alpha_v\beta_6$ in establishing metastases which is consistent with previous reports that $\alpha_v\beta_6$ can mediate epithelial to mesenchymal transition, tumor cell invasion in vitro, and expression correlated with metastases in a mouse model (Bates, R. C. et al., J. Clin. Invest. 115(2):339-347 (2005); Thomas, G. J. et al., Br. J. Cancer 87(8):859-867 (2002); Morgan, M. R. et al., J. Biol. Chem. 279(25):26533-26539 (2004)). We have previously described the generation of potent and selective anti-$\alpha_v\beta_6$ monoclonal antibodies (mAbs) that bind to both the human and murine forms of $\alpha_v\beta_6$ and block the binding of $\alpha_v\beta_6$ to its ligands and $\alpha_v\beta_6$ mediated activation of TGF-β1 (Weinreb, P. H. et al., J. Biol. Chem. 279(17):17875-17887 (2004)).

The generation of potent and selective anti-$\alpha_v\beta_6$ monoclonal antibodies (mAbs) that bind to both the human and murine forms of $\alpha_v\beta_6$ and block the binding of $\alpha_v\beta_6$ to its ligands and $\alpha_v\beta_6$ mediated activation of TGF-β1 has been previously described (Weinreb, P. H. et al., J. Biol. Chem. 279(17):17875-17887 (2004); see also U.S. patent application Ser. No. 11/483,190 by Violette et al., entitled "Anti-$\alpha_v\beta_6$ Antibodies and Uses Thereof," filed on Jul. 10, 2006, which is incorporated herein by reference in its entirety). As also described in PCT Publication WO 03/100033, herein incorporated in its entirety by reference, high affinity antibodies against $\alpha_v\beta_6$, including the identification and analysis of key amino acid residues in the complementary determining regions (CDRs) of such antibodies, were discovered and characterized. In particular, these high affinity antibodies (a) specifically bind to $\alpha_v\beta_6$; (b) inhibit the binding of $\alpha_v\beta_6$ to its ligand such as LAP, fibronectin, vitronectin, and tenascin with an $IC_{50}$ value lower than that of 10D5 (International Patent Application Publication WO 99/07405); (c) block activation of TGF-β; (d) contain certain amino acid sequences in the CDRs that provide binding specificity to $\alpha_v\beta_6$; (e) specifically bind to the $\beta_6$ subunit; and/or (f) recognize $\alpha_v\beta_6$ in immunostaining procedures, such as immunostaining of paraffin-embedded tissues.

WO 03/100033 also describes the discovery that antibodies that bind to $\alpha_v\beta_6$ can be grouped into biophysically distinct classes and subclasses. One class of antibodies exhibits the ability to block binding of a ligand (e.g., LAP) to $\alpha_v\beta_6$ (blockers). This class of antibodies can be further divided into subclasses of cation-dependent blockers and cation-independent blockers. Some of the cation-dependent blockers contain an arginine-glycine-aspartate (RGD) peptide sequence, whereas the cation-independent blockers do not contain an RGD sequence. Another class of antibodies exhibits the ability to bind to $\alpha_v\beta_6$ and yet does not block binding of $\alpha_v\beta_6$ to a ligand (nonblockers).

Furthermore, WO 03/100033 discloses antibodies comprising heavy chains and light chains whose complementarity determining regions (CDR) 1, 2 and 3 consist of certain amino acid sequences that provide binding specificity to $\alpha_v\beta_6$. WO 03/100033 also provides for antibodies that specifically bind to $\alpha_v\beta_6$ but do not inhibit the binding of $\alpha_v\beta_6$ to latency associated peptide (LAP) as well as antibodies that bind to the same epitope.

WO 03/100033 further discloses cells of hybridomas 6.1A8, 6.2B10, 6.3G9, 6.8G6, 6.2B1, 6.2A1, 6.2E5, 7.1G10, 7.7G5, and 7.1C5, isolated nucleic acids comprising a coding sequences and isolated polypeptides comprising amino acid sequences of the anti-$\alpha_v\beta_6$ antibodies. In particular, WO 03/100033 discloses anti-$\alpha_v\beta_6$ antibodies comprising heavy and light chain polypeptide sequences as antibodies produced by hybridomas 6.1A8, 6.3G9, 6.8G6, 6.2B1, 6.2B10, 6.2A1, 6.2E5, 7.1G10, 7.7G5, or 7.1C5. Several of the hybridomas were deposited at the American Type Culture Collection ("ATCC"; P.O. Box 1549, Manassas, Va. 20108, USA) under the Budapest Treaty. In particular, hybridoma clones 6.3G9 and 6.8G6 were deposited on Aug. 16, 2001, and have accession numbers MCC PTA-3649 and PTA-3645, respectively. The murine antibodies produced by hybridomas 6.3G9 and 6.8G6 are being further explored in the present application for their potential development as humanized antibodies.

The murine monoclonal antibody 3G9 is a murine IgG1, kappa antibody isolated from the $\beta_6$ integrin −/− mouse (Huang et al., J. Cell Biol. 133:921-928 (1996)) immunized with human soluble $\alpha_v\beta_6$. The 3G9 antibody specifically recognizes the $\alpha_v\beta_6$ integrin epitope which is expressed at upregulated levels during injury, fibrosis and cancer (see, e.g., Thomas et al., J. Invest. Dermatology 117:67-73 (2001); Brunton et al., Neoplasia 3: 215-226 (2001); Agrez et al., Int. J. Cancer 81:90-97 (1999); Breuss, J. Cell Science 108:2241-2251 (1995)). It does not bind to other $\alpha_v$ integrins and is cross-reactive to both human and murine molecules. The murine monoclonal antibody 3G9 has been described to block the binding of $\alpha_v\beta_6$ to LAP as determined by blocking of ligand binding either to purified human soluble $\alpha_v\beta_6$ or to $\beta_6$-expressing cells, thereby inhibiting the pro-fibrotic activity of TGF-β receptor activation (see WO 03/100033). It has also been shown to inhibit $\alpha_v\beta_6$-mediated activation of TGF-β with an $IC_{50}$ value lower than one of the known $\alpha_v\beta_6$ antibodies, 10D5 (Huang et al., J. Cell Sci. 111:2189-2195 (1998)).

The murine monoclonal antibody 8G6 is a murine IgG1, kappa antibody which also recognizes the $\alpha_v\beta_6$ integrin epitope, as described in WO 03/100033. The murine monoclonal antibody 8G6 is a cation-dependent, high affinity blocker of $\alpha_v\beta_6$ displaying the ability to inhibit $\alpha_v\beta_6$—mediated activation of TGF-β with an $IC_{50}$ value lower than 10D5 (see WO 03/100033).

Both the 3G9 and 8G6 murine antibodies were effective in preventing fibrosis of the kidney and lung, as described in WO 03/100033. Furthermore, the murine antibody 3G9 was able to effectively inhibit tumor growth in a human tumor xenograft model, suggesting the potential role of $\alpha_v\beta_6$ in cancer pathology and the effectiveness of such blockade using antibodies directed at $\alpha_v\beta_6$.

Smad4 is a component of the Smad pathway that is involved in signal transduction in the TGF-β pathway (Levy, L. and Hill, C. S., Molec. Cell. Biol. 25:8108-8125 (2005); Fukuchi, M. et al., Cancer 95:737-743 (2002)). This gene, also known as dpc4 (for "decreased in pancreatic carcinoma"), appears to be a tumor suppressor gene, and a decrease in smad4 expression has been observed in a variety of primary carcinomas, including pancreatic carcinomas (Luttges, J. et al., Am. J. Pathol. 158:1677-1683 (2001); Subramanian, G. et al., Cancer Res. 64:5200-5211 (2004)), esophageal carcinomas (Fukuchi, M. et al., Cancer 95:737-743 (2002), cervical carcinomas (Maliekal, T. T. et al., Oncogene 22:4889-4897 (2003), and other primary human cancers (Iacobuzio-Donahue, C. A. et al., Clin. Canc. Res. 10:1597-1604 (2004), as well as in cell line cancer models including of pancreatic cancers (Lohr, M. et al., Cancer Res. 61:550-555 (2001); Yasutome, M. et al., Clin. Exp. Metastasis 22:461-473 (2005)), and of colon cancers (Levy, L., and Hill, C. S., Molec. Cell. Biol. 25:8108-8125 (2005)). A reduced expression of smad4 in tumors has been associated with poor prognosis for patient survival, particularly in patients with smad4-deficient pancreatic adenocarcinomas (Liu, F., Clin. Cancer Res. 7:3853-3856 (2001); Tascilar, M. et al., Clin. Cancer Res. 7:4115-4121 (2001); Toga, T. et al., Anticancer Res. 24:1173-1178 (2004)). The mechanism of the tumor suppressive activity of the smad4 gene product is poorly understood, but it is thought that it may act as a "switch" regulating the growth-suppressive and growth-activating activities of certain components of the TGF-β signaling pathway (for reviews, see Akhurst, A. J., J. Clin. Invest. 109:1533-1536 (2002); Bachman, K. E., and Park, B. H., Curr. Opin. Oncol. 17:49-54 (2004); Bierie, B., and Moses, H. L., Nature Rev. Cancer 6:506-520 (2006)).

BRIEF SUMMARY OF THE INVENTION

The present invention relates to methods of cancer diagnosis, treatment and prevention using $\alpha_v\beta_6$-binding ligands, such as $\alpha_v\beta_6$-binding antibodies. In particular, the invention relates to the discovery of a correlation between reduced expression of smad4 and increased expression of integrin $\alpha_v\beta_6$ in tumor cells, and the propensity of tumor cells with such expression patterns to be more likely to respond to $\alpha_v\beta_6$-active compounds and to TGF-β-inhibitory ligands.

Thus, in one embodiment, the invention provides methods of characterizing a tumor, e.g., identifying a tumor that is more likely to progress to a metastatic or invasive tumor, or identifying a tumor for treatment with a preselected agent, e.g., an anti-$\alpha_v\beta_6$ agent described herein, comprising: (a) obtaining from a patient a cancerous tissue sample comprising a tumor or a portion thereof, and optionally a noncancerous tissue sample; (b) determining the level of expression of smad4 in cells from said cancerous tissue sample and optionally from said noncancerous tissue sample; (c) contacting cells from said tissue sample or samples with one or more ligands that bind to one or more subunits of integrin $\alpha_v\beta_6$; and (d) determining the level of expression of integrin $\alpha_v\beta_6$ in said cells from said cancerous tissue sample, and optionally from said cells from said noncancerous tissue sample, and comparing the level of expression in said cancerous tissue sample with a reference sample, e.g., the level of expression in said noncancerous tissue sample, thereby characterizing the tumor. A level of expression in the cancerous sample which meets or exceeds a reference value indicates the presence of a tumor more likely to progress to a metastatic or invasive tumor. For example, a decrease in smad4 expression and a concomitant increase in the level of expression of integrin $\alpha_v\beta_6$ in cells from said cancerous tissue sample, relative to the levels of expression of smad4 and integrin $\alpha_v\beta_6$ in said noncancerous tissue sample, indicates the presence in said patient of a tumor that is more likely to progress to a metastatic or invasive tumor. In certain such embodiments of the invention, the tumor cell is a carcinoma, such as an adenocarcinoma. In more particular embodiments, the carcinoma is a pancreatic carcinoma, a colorectal carcinoma, a cervical carcinoma, a squamous cell carcinoma (such as an esophageal carcinoma), a head and neck carcinoma, a liver carcinoma, an ovarian carcinoma and a lung carcinoma. More particularly, the carcinoma is a pancreatic carcinoma, a colorectal carcinoma, a cervical carcinoma, or a head and neck carcinoma. Suitable embodiments according to this aspect of the invention use $\alpha_v\beta_6$ integrin-binding ligands which are $\alpha_v\beta_6$-binding antibodies or $\alpha_v\beta_6$ epitope-binding fragments thereof. According to certain such embodiments, the antibodies are monoclonal antibodies (which may be chimeric, primatized, human or humanized), including those disclosed in U.S. patent application publication no. U.S. 2005/0255102 A1, the disclosure of which is incorporated herein in its entirety. Suitable such antibodies include, but are not limited to, the $\alpha_v\beta_6$-binding monoclonal antibodies designated 1A8, 3G9, 8G6, 2B1, 2B10, 2A1, 2E5, 1G10, 7G5, 1C5, 10D5 (ATCC deposit no. HB12382) and CSβ6, as well as fragments, chimeras and hybrids thereof. Particularly suitable for use in such embodiments of the invention are monoclonal antibodies 3G9 and 8G6. Also particularly suitable for use in such embodiments of the invention are humanized monoclonal antibodies, such as the humanized 3G9 antibody designated hu3G9 (BG00011) and the humanized 8G6 antibody designated hu8G6. In certain such aspects of the invention, the ligand is conjugated with at least one detectable label, such as a chromogenic label (e.g., diaminobenzidine or 4-hydroxyazo-benzene-2-carboxylic acid), an enzyme label (e.g., malate dehydrogenase, staphylococcal nuclease, delta-5-steroid isomerase, yeast-alcohol dehydrogenase, alpha-glycerol phosphate dehydrogenase, those phosphate isomerase, peroxidase, alkaline phosphatase, asparaginase, glucose oxidase, β-galactosidase, ribonuclease, urease, catalase, glucose-6-phosphate dehydrogenase, glucoamylase and acetylcholine esterase), a radioisotopic label (e.g., $^{3}H$, $^{111}In$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$ and $^{109}Pd$), a non-radioactive isotopic label (e.g., $^{157}Gd$, $^{55}Mn$, $^{162}Dy$, $^{52}Tr$, $^{56}Fe$, $^{99m}Tc$ and $^{112}In$), a fluorescent label (e.g., a $^{152}Eu$ label, a fluorescein label, an isothiocyanate label, a rhodamine label, a phycoerythrin label, a phycocyanin label, an allophycocyanin label, a Green Fluorescent Protein (GFP) label, an o-phthaldehyde label and a fluorescamine label), a toxic label (e.g., a diphtheria toxin label, a ricin label and a cholera toxin label), a chemiluminescent label (e.g., a luminol label, an isoluminol label, an aromatic acridinium ester label, an imidazole label, an acridinium salt label, an oxalate ester label, a luciferin label, a luciferase label and an aequorin label), an X-radiographic label (e.g., barium or cesium), a spin label (e.g., deuterium) or a nuclear magnetic resonance contrast agent label (e.g., Gd, Mn and iron).

In related embodiments, the invention provides therapeutic methods for eliminating tumors from patients, e.g, wherein the tumors have an increased potential to become metastatic or invasive. Such methods comprise, e.g., characterizing a tissue sample as described herein, for example: (a) identifying, in a tissue sample from a patient, a tumor that is more likely to progress to a metastatic or invasive tumor, according to the methods for identifying such tumors that are described above; and (b) administering to a patient, in which such a tumor has been identified, a therapeutically effective amount of one or more ligands that binds to one or more subunits of integrin $\alpha_v\beta_6$ on one or more $\alpha_v\beta_6$-positive metastatic tumor cells, wherein the binding of the ligand to the integrin results in the death, chemosensitization or decreased invasiveness of said metastatic tumor cell. In a preferred embodiment, the same agent, e.g., the same antibody is used to characterize the tumor and treat the patient. In other embodiments, different agents or antibodies are used. For example, characterizing can be performed with an antibody having a first label, and treating can be performed with an antibody having a second label, e.g., a therapeutic agent.

In related embodiments, the invention provides methods of reducing or preventing the progression of a pre-metastatic tumor to a metastatic tumor in a patient, comprising (a) characterizing a tissue sample as described herein, e.g., identifying, in a tissue sample from a patient, a tumor that is more likely to progress to a metastatic or invasive tumor, according to the methods for identifying such tumors that are described above; and (b) administering to the patient a therapeutically effective amount of one or more ligands that binds to one or more subunits of integrin $\alpha_v\beta_6$ on one or more cells in the pre-metastatic or pre-invasive tumor, wherein the binding of the ligand to the integrin results in the reduction or prevention of invasion of cells of the pre-metastatic cancer into tissue areas surrounding the primary tumor. In therapeutic embodiments according to this aspect of the invention, the $\alpha_v\beta_6$-binding ligands (e.g., $\alpha_v\beta_6$-binding antibodies) can be conjugated with or bound to one or more cytotoxic compounds or agents which lead to or cause the death of the cell or tissue upon binding of the $\alpha_v\beta_6$-binding ligand-toxic compound conjugate to one or more $\alpha_v\beta_6$ integrins on the cell or tissue. In some embodiments, the antibody used to characterize the tumor will lack the cytoxic compound or agent. In additional therapeutic embodiments of the invention, the $\alpha_v\beta_6$-binding ligands (e.g., $\alpha_v\beta_6$-binding antibodies) are administered to a patient in conjunction with one or more such cytotoxic compounds or agents. Cytotoxic compounds or agents which can be suitably used according to these aspects of the invention include, but are not limited to, cytotoxic agents (e.g., cisplatin, carboplatin, oxaliplatin, paclitaxel, melphalan, doxorubicin, methotrexate, 5-fluorouracil, etoposide, mechlorethamine, cyclophosphamide, bleomycin, a calicheamicin, a maytansine, a trichothene, CC1065, diphtheria A chain, Pseudomonas aeruginosa exotoxin A chain, ricin A chain, abrin A chain, modeccin A chain, alpha-sarcin, Aleurites fordii proteins, dianthin proteins, Phytolaca americana proteins, momordica charantia inhibitors, curcin, crotin, sapaonaria officinalis inhibitors, gelonin, mitogellin, restrictocin, adriamycin (also known as, and used interchangeably herein with, doxorubicin), gemcitabine, phenomycin, enomycin, tricothecenes, ribonucleases and deoxyribonucleases), radioisotopes (such as $^{211}At$, $^{131}I$, $^{125}I$, $^{90}Y$, $^{186}Re$, $^{188}Re$, $^{153}Sm$, $^{212}Bi$, $^{32}P$, and radioactive isotopes of Lu) and prodrug-activating enzymes (such as alkaline phosphatase, arylsulfatase, cytosine deaminase, proteases, D-alanylcarboxy-peptidases, carbohydrate-cleaving enzymes, P-lactamase and penicillin amidase. Cytotoxic agents can also be agents which recruit particular cells or generally increase the immune response to a tumor. In certain embodiments, the one or more $\alpha_v\beta_6$ integrin-binding ligands are administered to the patient in the form of a pharmaceutical composition comprising an effective amount of one or more of the $\alpha_v\beta_6$ integrin-binding ligands and one or more pharmaceutically acceptable carriers or excipients. The one or more $\alpha_v\beta_6$ integrin-binding ligands and/or one or more pharmaceutical compositions comprising the one or more $\alpha_v\beta_6$ integrin-binding ligands can be administered to the patient by any suitable mode of administering pharmaceutical compositions, including but not limited to oral administration, parenteral administration (including, for example, injection via an intramuscular, intravenous, intraarterial, intraperitoneal, or subcutaneous route), intracranial administration, transdermal administration, intrapulmonary administration and intranasal administration.

In additional embodiments, the present invention provides methods of diagnosing or identifying a tumor, such as a carcinoma (e.g., an adenocarcinoma), that is more likely to progress to an invasive carcinoma, and/or that is more likely to respond to treatment with a ligand that binds to one or more subunits of integrin $\alpha_v\beta_6$. Suitable such methods may comprise, for example, (a) obtaining from a patient a cancerous epithelial tissue sample comprising a tumor or a portion thereof, and a noncancerous epithelial tissue sample; (b) determining the level of expression of smad4 in cells from said tissue samples; (c) contacting the tissue samples with one or more ligands that binds to one or more subunits of integrin $\alpha_v\beta_6$; and (d) determining the level of expression of integrin $\alpha_v\beta_6$ in the tissue samples, wherein a decrease in the level of expression of smad4 and a concomitant increase in the level expression of integrin $\alpha_v\beta_6$ in the cancerous tissue sample, relative to the levels of expression of smad4 and integrin $\alpha_v\beta_6$ in the noncancerous tissue sample, indicates the presence in the patient of a tumor that: (a) has an increased likelihood of progressing from an in situ or noninvasive form, to an invasive, metastatic form; and/or (b) is more likely to respond to treatment with one or more of the above-referenced treatment methods that relies upon the binding of an $\alpha_v\beta_6$-binding ligand, particularly an $\alpha_v\beta_6$-binding ligand that is conjugated to or that is administered in conjunction with one or more cytotoxic compounds or agents such as those described above. Such methods are suitable for diagnosing or identifying a variety of tumors, including but not limited to those involving the epithelial tissues noted above. In certain such embodiments, the ligand that binds to one or more subunits of integrin $\alpha_v\beta_6$ is an $\alpha_v\beta_6$ integrin-binding antibody (which may be a monoclonal antibody such as those described above) or an $\alpha_v\beta_6$ epitope-binding fragment thereof. Particularly suitable for use in such diagnostic methods of the invention are $\alpha_v\beta_6$-binding ligands (e.g., antibodies) that are detectably labeled, i.e., that comprise, are conjugated to, or are bound with at least one detectable label such as a chromogenic label (e.g., diaminobenzidine or 4-hydroxyazobenzene-2-carboxylic acid), an enzyme label (e.g., malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase or acetylcholine esterase), a radioisotopic label g, $^{3}$H, $^{11}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc or $^{109}$Pd), a non-radioactive isotopic label (e.g., $^{157}$Gd, $^{55}$Mn, $^{162}$Dy, $^{52}$Tr, $^{56}$Fe, $^{99m}$Tc or $^{112}$In), a fluorescent label (e.g., a $^{152}$Eu label, a fluorescein label, an isothiocyanate label, a rhodamine label, a phycoerythrin label, a phycocyanin label, an allophycocyanin label, a Green Fluorescent Protein (GFP) label, an o-phthaldehyde label or a fluorescamine label), a toxic label (e.g., a diphtheria toxin label, a ricin label or a cholera toxin label), a chemiluminescent label (e.g., a luminol label, an isoluminol label, an aromatic acridinium ester label, an imidazole label, an acridinium salt label, an oxalate ester label, a luciferin label, a luciferase label or an aequorin label), an X-radiographic label (e.g., barium or cesium), a spin label (e.g., deuterium) and a nuclear magnetic resonance contrast agent label (e.g., Gd, Mn and iron).

In one aspect, the invention features a method of inhibiting growth of a cell from a tumor that is smad4 deficient. The method includes, for example, determining the level of expression of smad4 in a cell from the tumor, and treating a tumor cell that is deficient in smad4 expression with one or more agents that cause growth inhibition or death of the tumor cell. The one or more agents can be, for example, a ligand that binds to one or more subunits of integrin $\alpha_v\beta_6$, such as an anti-$\alpha_v\beta_6$ antibody, or an $\alpha_v\beta_6$ epitope-binding fragment thereof. In another embodiment, the one or more agents inhibits the TGF-β signaling pathway in the cell. Such agents include, e.g., protein kinase molecules, small molecule therapeutic compounds, or soluble TGF-β receptor polypeptides.

In another aspect, the invention features a method of chemosensitizing a smad-4-deficient tumor cell to treatment with a growth-inhibiting chemotherapeutic compound. The method includes, for example, determining the level of expression of smad4 in a cell from the tumor, and treating a tumor cell deficient for smad4 expression with one or more agents, such that the treatment results in increased responsiveness to one or more growth-inhibiting chemotherapeutic compounds. The one or more agents can be, for example, ligands that bind to one or more subunits of integrin $\alpha_v\beta_6$, or agents that inhibit the TGF-β signaling pathway.

Other preferred embodiments of the present invention will be apparent to one of ordinary skill in light of the following drawings and description of the invention, and of the claims.

BRIEF DESCRIPTION OF THE DRAWINGS

FIGS. 4A-4C: expression in primary tumor samples from three different patients.

FIGS. 4D-4F: expression in matched lymph node metastases from these same three patients. FIGS. 4G-4H:: expression in normal pancreatic tissue obtained from two of the three patients.

FIGS. 5A-5E: expression in primary tumor samples from five different patients, three with tumors characterized as adenosquamous (FIGS. 5A-5C), and two with tumors characterized as poorly differentiated (FIGS. 5D-5E). FIGS. 5F-5J: expression in matched lymph node metastases from these same five patients. FIGS. 5K-5L: expression in normal pancreatic tissue obtained from two of the five patients.

FIG. 6A: photomicrograph of a section of xenograft tumor stained via immunohistochemistry with an anti-αvβ6 monoclonal antibody (3G9). FIG. 6B: BxPC-3 xenograft tumor growth curves during treatment with αvβ6 mAb 3G9 (▲), soluble TGFbRII-Fc-Ig fusion protein (▼), or vehicle PBS (■). FIG. 6C: scatter plot of individual tumor sizes at the end of the study (day 66).

FIG. 14 is a summary of αvβ6 and smad4 expression levels in a panel of pancreatic cancer cell lines.

FIG. 15 is a composite of photomicrographs depicting the levels of αvβ6 and smad4 expression in pancreatic cancers as assayed by Folio array.

FIG. 30B is a line graph demonstrating the response of Panc04 human pancreatic adenocarcinoma cells, subcutaneously implanted into athymic nude mice, to mAb 3G9 and TGF-β RII-Fc, and to either agent in combination with gemcitabine, expressing the results of test animals as a percentage of control (vehicle) results.

FIG. 35 is a Table summarizing the results depicted in FIGS. 29-34.

FIGS. 36A-36D are Kaplan-Meier curves representing the cumulative survival of 26 patients from Leiden University Medical Center with pancreatic ductal adenocarcinoma in function of retention of avb6 or deficiencies of avb6 expression, or retention of smad4 or deficiencies of smad4 expression, and combinations of these phenotypes. Only data from primary tumors was analyzed.

DETAILED DESCRIPTION OF THE INVENTION

Figure 1:
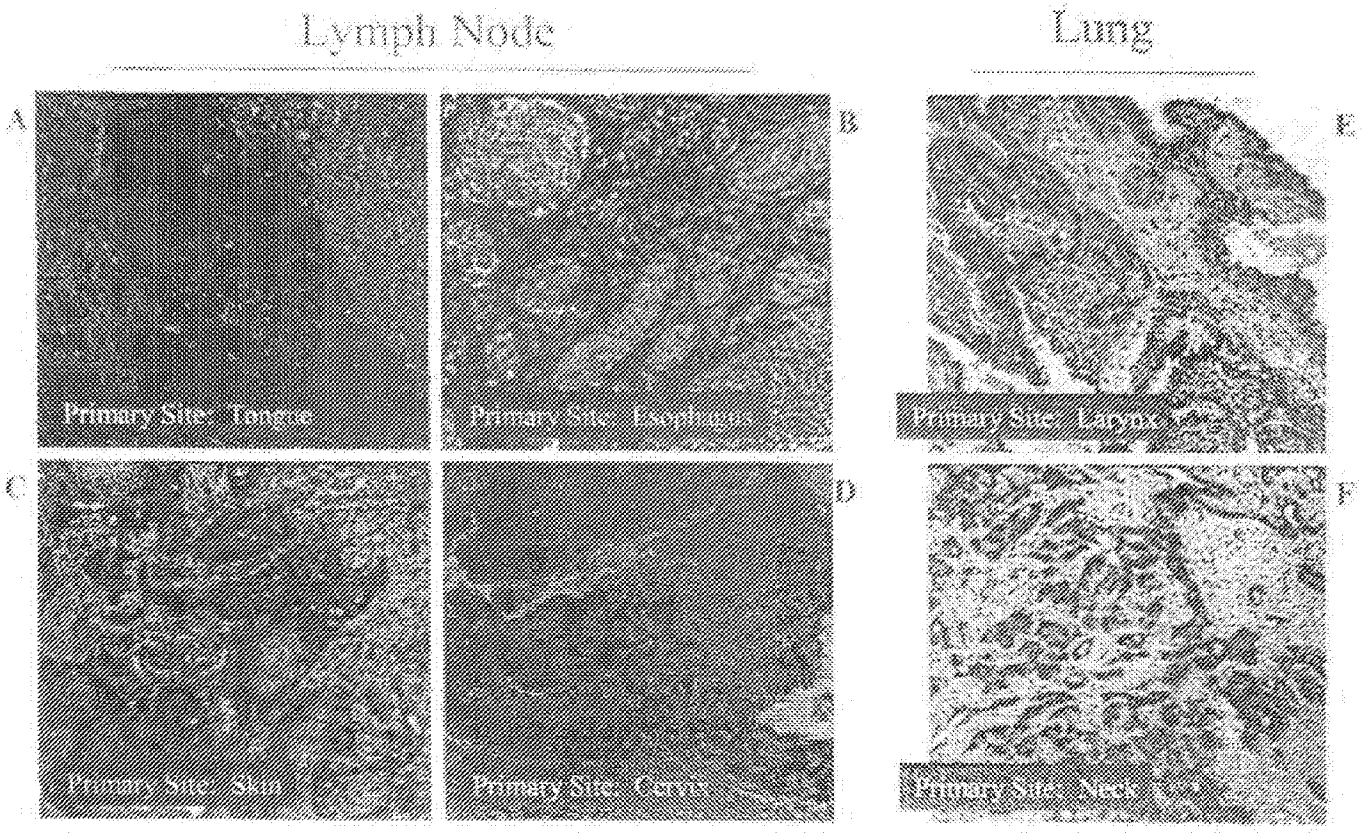
FIG. 1 is a composite of photomicrographs depicting the levels of $\alpha_v\beta_6$ expression (dark areas) in certain human carcinomas that have metastasized to either lymph node (FIGS. 1A-1D) or lung (FIGS. 1E-1F), from the indicated primary tumor sites.
Figure 2:
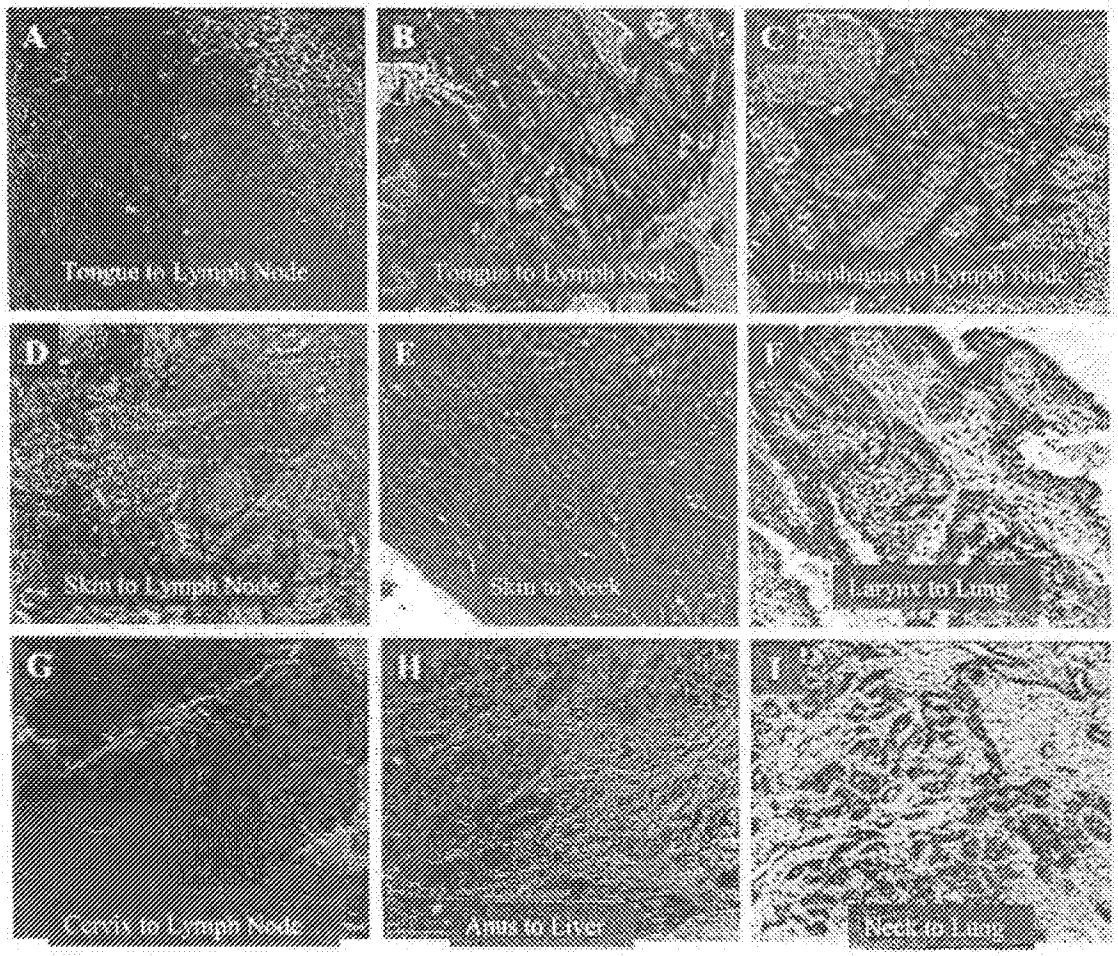
FIG. 2 is a composite of photomicrographs depicting the levels of $\alpha_v\beta_6$ expression (dark areas) in certain human carcinomas that have metastasized from the indicated primary tumor site to the indicated metastatic tumor site.
Figure 3A:
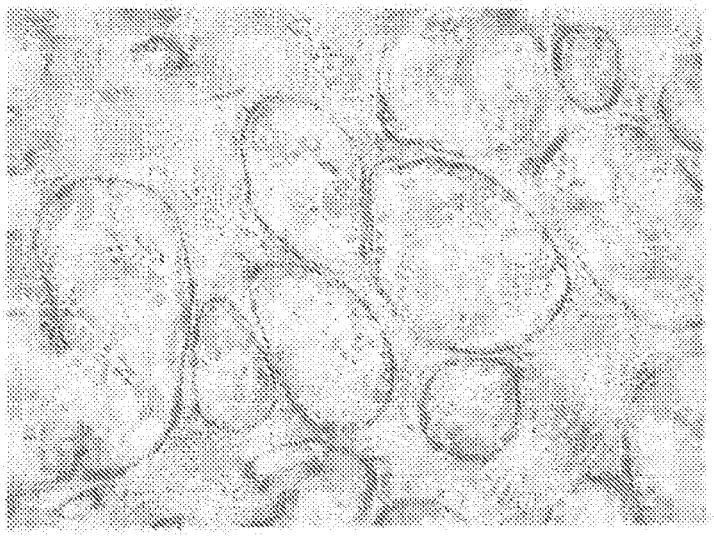
FIG. 3 is a composite of two photomicrographs depicting the levels of $\alpha v\beta_6$ expression (dark areas) observed in tissue sections of ductal carcinoma in situ (DCIS; BrCa 19) (FIG. 3A) and invasive breast carcinoma (BrCa 23) (FIG. 3B).
Figure 3B:
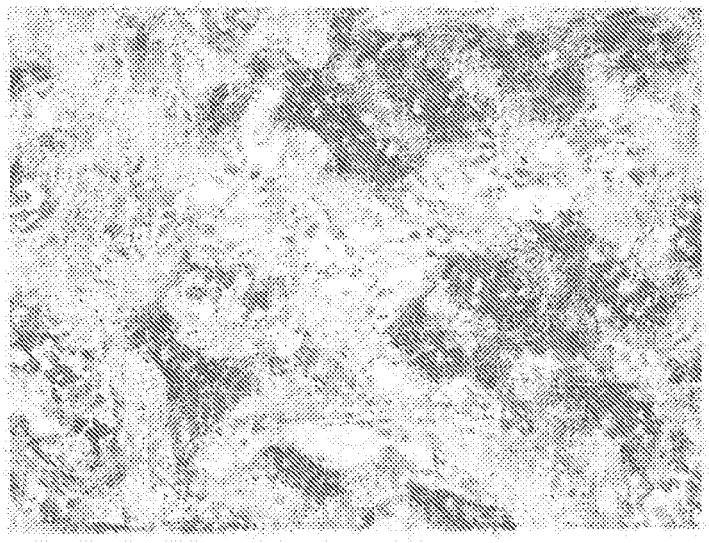

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described hereinafter.

Definitions

About: As used herein when referring to any numerical value, the term "about" means a value of ±10% of the stated value (e.g., "about 50° C." encompasses a range of temperatures from 45° C. to 55° C., inclusive; similarly, "about 100 mM" encompasses a range of concentrations from 90 mM to 110 mM, inclusive).

Antagonist: As used herein, the term "antagonist" refers to a compound, molecule, moiety or complex that reduces, substantially reduces or completely inhibits the biological and/or physiological effects of the $\alpha_v\beta_6$ integrin in a cell, tissue or organism. Antagonists, which may be ligands for $\alpha_v\beta_6$, may carry out such effects in a variety of ways, including but not limited to competing with another ligand for binding to $\alpha_v\beta_6$ on the cell surface; interacting with $\alpha_v\beta_6$ in such a way as to reduce, substantially reduce or inhibit the ability of the integrin to bind other ligands; binding to and inducing a conformational change in cell surface $\alpha_v\beta_6$ such that the integrin assumes a structure to which other ligands can no longer bind (or can bind only with reduced or substantially reduced affinity and/or efficiency); inducing a physiological change (e.g., increase in intracellular signaling complexes; increase in transcriptional inhibitors; reduction in cell surface $\alpha_v\beta_6$ expression; etc.) in cells, tissues or organisms such that the binding of other ligands, or the physiological signal induced by such ligands upon binding to the $\alpha_v\beta_6$ on the cell, is reduced, substantially reduced or completely inhibited; and other mechanisms by which antagonists may carry out their activities, that will be familiar to the ordinarily skilled artisan. As the ordinarily skilled artisan will understand, an antagonist may have a similar structure to another $\alpha_v\beta_6$-binding moiety (e.g., an $\alpha_v\beta_6$-binding ligand) that it antagonizes (e.g., the antagonist may be a mutein, variant, fragment or derivative of the agonist), or may have a wholly unrelated structure.

Bound: As used herein, the term "bound" refers to binding or attachment that may be covalent, e.g., by chemically coupling, or non-covalent, e.g., ionic interactions, hydrophobic interactions, hydrogen bonds, etc. Covalent bonds can be, for example, ester, ether, phosphoester, thioester, thioether, urethane, amide, amine, peptide, imide, hydrazone, hydrazide, carbon-sulfur bonds, carbon-phosphorus bonds, and the like.

The term "bound" is broader than and includes terms such as "coupled," "conjugated" and "attached."

Conjugate/conjugation: As used herein, "conjugate" refers to the product of covalent attachment of a moiety, e.g., a chemical or radioisotope, to a ligand that binds to $\alpha_v\beta_6$, e.g., an $\alpha_v\beta_6$-binding antibody or fragment thereof. "Conjugation" refers to the formation of a conjugate as defined in the previous sentence. Any method normally used by those skilled in the art of conjugation of chemicals or radioisotopes to biologically active materials, such as proteins or polypeptides (including antibodies) can be used in the present invention.

Disease, disorder, condition: As used herein, the terms "disease" or "disorder" refer to any adverse condition of a human or animal including tumors, cancer, allergies, addiction, autoimmunity, infection, poisoning or impairment of optimal mental or bodily function. "Conditions" as used herein includes diseases and disorders but also refers to physiologic states. For example, fertility is a physiologic state but not a disease or disorder. Compositions of the invention suitable for preventing pregnancy by decreasing fertility would therefore be described as a treatment of a condition (fertility), but not a treatment of a disorder or disease. Other conditions are understood by those of ordinary skill in the art.

Effective Amount: As used herein, the term "effective amount" refers to an amount of a given compound, conjugate or composition that is necessary or sufficient to realize a desired biologic effect. An effective amount of a given compound, conjugate or composition in accordance with the methods of the present invention would be the amount that achieves this selected result, and such an amount can be determined as a matter of routine by a person skilled in the art, using assays that are known in the art and/or that are described herein, without the need for undue experimentation. For example, an effective amount for treating or preventing cancer metastasis could be that amount necessary to prevent migration and invasion of a tumor cell across the basement membrane or across an endothelial layer in vivo. The term is also synonymous with "sufficient amount." The effective amount for any particular application can vary depending on such factors as the disease, disorder or condition being treated, the particular composition being administered, the route of administration, the size of the subject, and/or the severity of the disease or condition. One of ordinary skill in the art can determine empirically the effective amount of a particular compound, conjugate or composition of the present invention, in accordance with the guidance provided herein, without necessitating undue experimentation.

One, a, or an: When the terms "one," "a," or "an" are used in this disclosure, they mean "at least one" or "one or more," unless otherwise indicated. An such, the terms "a" (or "an"), "one or more," and "at least one" can be used interchangeably herein.

Peptide, polypeptide, protein: As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. In accordance with this definition, polypeptides used in the present invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to at unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue. Preferred polypeptides used in accordance with the invention include polypeptides that are ligands or that bind to an $\alpha_v\beta_6$ integrin on the surface of a cell, including but not limited to antibodies (especially monoclonal antibodies) that recognize and bind to one or more epitopes on $\alpha_v\beta_6$.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

Also included as polypeptides of the present invention are fragments, derivatives, analogs, or variants of the foregoing polypeptides, and any combination thereof. The terms "fragment," "variant," "derivative" and "analog" when referring to anti-$\alpha_v\beta_6$ antibodies or antibody polypeptides include any polypeptides which retain at least some of the antigen-binding properties of the corresponding native antibody or polypeptide, i.e., those polypeptides that retain the ability to bind to one or more epitopes on an $\alpha_v\beta_6$ integrin. Fragments of polypeptides of the present invention include proteolytic fragments, as well as deletion fragments, in addition to specific antibody fragments discussed elsewhere herein. Variants of anti-$\alpha_v\beta_6$ antibodies and antibody polypeptides useful in accordance with the present invention include fragments as described above, and also polypeptides with altered amino acid sequences due to amino acid substitutions, deletions, or insertions. Variants may occur naturally or be non-naturally occurring Non-naturally occurring variants may be produced using art-known mutagenesis techniques. Variant polypeptides may comprise conservative or non-conservative amino acid substitutions, deletions or additions. Derivatives of anti-$\alpha_v\beta_6$ antibodies and antibody polypeptides useful in accordance with the present invention are polypeptides which have been altered so as to exhibit additional features not found on the native polypeptide. Examples include fusion proteins. Variant polypeptides may also be referred to herein as "polypeptide analogs." As used herein a "derivative" of an anti-$\alpha_v\beta_6$ antibody or antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

smad4: As used herein, the tumor suppressor gene smad4 is synonymous with other designations for the same tumor suppressor gene that are known to those of skill in the art, including but not limited to madh4 and dpc4. As is conventional, the products of the expression of this gene is designated herein as SMAD4, which is synonymous with the corresponding other designations for the expression product of this gene that are known to those of skill in the art, including but not limited to MADH4 and DPC4.

Substantially, substantial: As used herein, conjugation of a protein is said not to interfere "substantially" with the ability of the protein to bind to its receptor(s) if the rate and/or amount of binding of a conjugated protein to a receptor is not less than about 40%, about 50%, about 60%, about 65%, about 70%, about 75%, about 80%, about 85%, about 90%, about 91%, about 92%, about 93%, about 94%, about 95%, about 96%, about 97%, about 98%, about 99% or about 100% or more, of the binding rate and/or amount of the corresponding cytokine, chemokine, growth factor or polypeptide hormone that has not been conjugated.

Treatment: As used herein, the terms "treatment," "treat," "treated" or "treating" refer to prophylaxis and/or therapy, particularly wherein the object is to prevent or slow down (lessen) an undesired physiological change or disorder, such as the progression of multiple sclerosis. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. By "subject" or "individual" or "animal" or "patient" or "mammal," is meant any subject, particularly a mammalian subject, for whom diagnosis, prognosis, or therapy is desired. Mammalian subjects include humans and other primates, domestic animals, farm animals, and zoo, sports, or pet animals such as dogs, cats, guinea pigs, rabbits, rats, mice, horses, cattle, cows, and the like.

Overview

The present invention is based at least in part upon the findings that there is an inverse relationship between the level of expression of the tumor suppressor gene smad4 and the integrin $\alpha_v\beta_6$ in certain tumor cells, and that the levels of expression of these two markers can be used to determine or predict the susceptibility to treatment with anti-integrin ligands, and with agents that antagonize the TGF-β signalling pathway, of such tumor cells. Specifically, it has been found that tumor cells that display decreased levels of expression of smad4 concomitantly express increased amounts of the integrin $\alpha_v\beta_6$; therefore, smad-4-deficient tumor cells have a higher propensity to be responsive to ligands that bind to integrin $\alpha_v\beta_6$, compared to tumor cells that display higher expression levels of smad4 (and, concomitantly, lower levels of surface integrin $\alpha_v\beta_6$). In related embodiments, it has also been found by the present inventors that smad-4-deficient tumor cells are also more likely to be responsive to ligands that antagonize one or more components of the TGF-β signalling pathway, compared to tumor cells that display higher expression levels of smad4. As used herein, a tumor cell that is "responsive" to a ligand that binds to integrin $\alpha_v\beta_6$, or to a ligand that antagonizes one or more components of the TGF-β pathway, refers to a tumor cell in which the growth, division, and/or other metabolic pathways are adversely affected such that the cell is inhibited from growing or dividing and/or undergoes apoptosis or other forms of cell death.

In other embodiments, the invention also provides methods using identification of this differential expression in determining the invasive and/or metastatic potential of tumor cells and in identifying those carcinomas, such as certain adenocarcinomas (including pancreatic carcinomas), that may be more likely to rapidly progress and which should be aggressively treated in a patient. The invention also provides methods of identifying those tumors in which the cells making up the tumor may be more likely to respond to treatment with one or more ligands that bind to integrin $\alpha_v\beta_6$. The invention also provides methods of diagnosis and treatment/prevention of tumor metastasis.

Determination of Expression of smad4 and Integrin $\alpha_v\beta_6$

In one embodiment, the present invention is directed to methods for identifying tumors and tumor cells, particularly carcinoma cells such as pancreatic carcinoma cells, that are more likely to be responsive to ligands that bind to integrin αvβ6, and/or to ligands that antagonize one or more components of the TGF-β signaling pathway. Such methods include, for example, determining the levels of expression of the tumor suppressor gene smad4 by the tumor cells, wherein a reduced expression of smad4 indicates that the tumor cell is more likely to be responsive to ligands that bind to integrin αvβ6, and/or to ligands that antagonize one or more components of the TGF-β signalling pathway. In certain such embodiments, the level of expression of smad4 in cells of a tumor, e.g., a carcinoma, is determined in tissue sections obtained from a patient suffering from such a tumor, wherein a decrease in the expression of smad4 in the tumor cells relative to that in non-tumor tissue samples (ideally, from the same organ in the same patient) indicates that the tumor is more likely to be responsive to ligands that bind to integrin αvβ6, and/or to ligands that antagonize one or more components of the TGF-β signalling pathway. In this way, appropriate and aggressive protocols for treating such tumors in a patient can rapidly be identified and implemented, thereby providing an increased likelihood of positive treatment outcomes for cancer patients.

In each such embodiment, the invention relies upon identification or exploitation of the decreased expression of smad4, and the concomitant increased expression of $\alpha_v\beta_6$, in certain tumor cells. The level of expression of smad4 can be readily determined using methods that are well-known in the art for measuring gene expression, including, for example, hybridization or PCR/RT-PCR using known genetic probes or primers specific for the smad4 gene (see, e.g., Maliekal, T. T. et al., Oncogene 22:4889-4897 (2003); Iacobuzio-Donahue, C. A. et al., Clin. Cancer Res. 10:1597-1604 (2004)), northern blotting (see, e.g., Yasutome, M. et al., Clin. Exper. Metast. 22:461-473 (2005)), and immunohistochemical analysis with anti-SMAD4 antibodies (see, e.g., Lüttges, J. et al., Am. J. Pathol. 158:1677-1683 (2001); Fukuchi, M. et al., Cancer 95:737-743 (2002); Subramanian, G. et al., Cancer Res. 64:5200-5211 (2004); Levy, L. and Hill, C. S., Mol. Cell. Biol. 25:8108-8125 (2005); Toga, T. et al., Anticancer Res. 24:1173-1178 (2004)). Other methods suitable for detecting the level of smad4 gene expression in a given cell, tissue, organ or biological sample will be familiar to those of ordinary skill in the art. Similarly, the level of expression of $\alpha_v\beta_6$ can be readily determined using methods that are well-known in the art for measuring integrin expression. In certain such embodiments, such determinations are accomplished by contacting the tissue, tumor or tumor cells with one or more ligands that binds to integrin $\alpha_v\beta_6$ in the tissue, tumor or tumor cells.

In certain such embodiments, the tissue, tumor or tumor cells are carcinoma tissues, tumors or tumor cells, including those from carcinomas such as adenocarcinomas. In more particular embodiments, the carcinoma is pancreatic carcinoma, a colorectal carcinoma, a cervical carcinoma, a squamous cell carcinoma (such as an esophageal carcinoma), a head and neck carcinoma, a liver carcinoma, an ovarian carcinoma and a lung carcinoma. More particularly, the carcinoma is a pancreatic carcinoma, a colorectal carcinoma, a cervical carcinoma, or a head and neck carcinoma.

In certain embodiments of the invention, the ligands that bind to $\alpha_v\beta_6$ are antagonists of $\alpha_v\beta_6$. Such antagonists include but are not limited to antibodies which specifically bind to $\alpha_v\beta_6$; antibodies which specifically bind to $\beta_6$; antibodies that bind to $\alpha_v$; antibodies that bind to ligands for $\alpha_v\beta_6$; ligands for $\alpha_v\beta_6$; antisense nucleic acids; and peptide, non-peptide, and peptidomimetic analogs of such ligands.

In certain such embodiments of the present invention, the ligand that binds to integrin $\alpha_v\beta_6$ is an antibody that binds to integrin $\alpha_v\beta_6$, or integrin $\alpha_v\beta_6$-binding fragments, variants, or derivatives thereof. Such antibodies may bind to one subunit of the integrin (e.g., antibodies that bind to an epitope located on the $\alpha_v$ subunit or to an epitope that is located on the $\beta_6$ subunit), or to both subunits (e.g., antibodies that bind to an epitope that is located in a region of the integrin heterodimer that bridges both the $\alpha_v$ and $\beta_6$ subunits). Unless specifically referring to full-sized antibodies such as naturally occurring antibodies, the term "$\alpha_v\beta_6$ antibodies" encompasses full-sized antibodies as well as $\alpha_v\beta_6$-binding fragments, variants, analogs, or derivatives of such antibodies, e.g., naturally occurring antibody or immunoglobulin molecules or engineered antibody molecules or fragments that bind antigen in a manner similar to antibody molecules. Antibodies can be synthetic, monoclonal, or polyclonal and can be made by techniques well known in the art. For therapeutic applications, "human" monoclonal antibodies having human constant and variable regions are often preferred so as to minimize the immune response of a patient against the antibody. Such antibodies can be generated by immunizing transgenic animals which contain human immunoglobulin genes (see, e.g., Jakobovits et al., Ann. N.Y. Acad. Sci. 764:525-535 (1995)). In connection with synthetic and semi-synthetic antibodies, such terms are intended to cover but are not limited to antibody fragments, isotype switched antibodies, humanized antibodies (e.g., mouse-human, human-mouse, and the like), hybrids, antibodies having plural specificities, fully synthetic antibody-like molecules, and the like.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988). As will be understood by those of ordinary skill, the terms "antibody" and "immunoglobulin" comprise various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma$1-$\gamma$4). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernable to the skilled artisan in view of the instant disclosure and, accordingly, are within the scope of the instant invention.

Antibodies that bind to $\alpha_v\beta_6$ , or $\alpha_v\beta_6$-binding fragments, variants, or derivatives thereof, that are suitable for use in the present invention include but are not limited to polyclonal, monoclonal, multispecific, human, humanized, primatized, or chimeric antibodies, single chain antibodies, epitope-binding fragments, e.g., Fab, Fab' and $F(ab')_2$, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to anti-$\alpha_v\beta_6$ antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Antibody fragments, including single-chain antibodies, may comprise the variable region(s) alone or in combination with the entirety or a portion of the following: hinge region, $C_H1$, $C_H2$, and $C_H3$ domains. Also included in the invention are antigen-binding fragments also comprising any combination of variable region(s) with a hinge region, $C_H1$, $C_H2$, and $C_H3$ domains. Antibodies or immunospecific fragments thereof for use in the diagnostic and therapeutic methods disclosed herein may be from any animal origin including birds and mammals. Preferably, the antibodies are human, murine, rat, donkey, rabbit, goat, guinea pig, camel, llama, horse, bovine or chicken antibodies. Most preferably, the antibodies are human, humanized or primatized antibodies, or chimeric antibodies, particularly monoclonal antibodies. As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al. As used herein, the term "chimeric antibody" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g. mouse or primate) and the constant region is human.

Particularly preferred antibodies for use in accordance with the present invention are anti-$\alpha_v\beta_6$ monoclonal antibodies such as those disclosed in Weinreb et al., J. Biol. Chem. 279(17):17875-17877 (2004) (the disclosure of which is incorporated herein by reference in its entirety), including monoclonal antibodies 6.8G6 ("8G6") and 6.3G9 ("3G9") disclosed therein. Additional antibodies that bind to $\alpha_v\beta_6$ and that therefore are suitable for use in accordance with the present invention include antibodies (or fragments, variants or derivatives thereof) that bind to the $\beta_6$ subunit of integrin $\alpha_v\beta_6$ (and that are therefore considered "anti-$\beta_6$ antibodies"), such as those disclosed in Weinacker et al., J. Cell Biol. 269:1-9 (1994), which is incorporated herein by reference in its entirety; and in U.S. Pat. No. 6,692,741 B2, which is incorporated herein by reference in its entirety, particularly at columns 2-3 and 7-8 thereof, including the monoclonal antibody designated 10D5 (ATCC deposit no. HB12382, deposited Aug. 6, 1997, American Type Culture Collection, P.O. Box 1549, Manassas, Va. 20108) (see U.S. Pat. No. 6,692,741 at col. 3, lines 7-13, and at cols. 7-8) and CSβ6 (see U.S. Pat. No. 6,692,741 at cols. 7-8). Suitable embodiments according to this aspect of the invention use $\alpha_v\beta_6$ integrin-binding ligands which are $\alpha_v\beta_6$-binding antibodies or $\alpha_v\beta_6$ epitope-binding fragments thereof. Additional antibodies suitable for use in accordance with this aspect of the invention include, but are not limited to, the $\alpha_v\beta_6$-binding monoclonal antibodies disclosed in U.S. patent application publication no. US 2005/0255102 A1, the disclosure of which is incorporated herein in its entirety, including those designated therein as 3G9, 8G6, 1A8, 2B1, 2B10, 2A1, 2E5, 1G10, 7G5, 1C5, as well as fragments, chimeras and hybrids thereof. Particularly suitable antibodies for use in accordance with the present invention are monoclonal antibodies 2B1, 3G9 and 8G6.

In some embodiments, the antibodies comprise the same heavy and light chain polypeptide sequences as an antibody produced by hybridoma 6.1A8, 6.3G9, 6.8G6, 6.2B1, 6.2B10, 6.2A1, 6.2E5, 7.1G10, 7.7G5, or 7.1C5. Particularly suitable antibodies for use in accordance with the present invention are monoclonal antibodies that comprise the same heavy and light chain polypeptide sequences as 2B1 antibodies produced by hybridoma 6.2B1 (ATCC deposit no. PTA-3646, deposited Aug. 16, 2001, American Type Culture Collection, P.O. Box 1549, Manassas, Va. 20108), 8G6 antibodies produced by hybridoma 6.8G6 (ATCC deposit no. PTA-3645, deposited Aug. 16, 2001, American Type Culture Collection, P.O. Box 1549, Manassas, Va. 20108) and 3G9 antibodies produced by hybridoma 6.3G9 (ATCC deposit no. PTA-3649, deposited Aug. 16, 2001, American Type Culture Collection, P.O. Box 1549, Manassas, Va. 20108) (see published U.S. Appl. No. U.S. 2005/0255102 A1, the disclosure of which is incorporated herein by reference in its entirety, particularly at page 1, paragraph 0008; at page 2, paragraphs 0032 and 0036; and in the Examples at pages 6-14), and the antibody designated as 10D5 (the hybridoma secreting which antibody was deposited on Aug. 6, 1997, as ATCC deposit no. HB12382, American Type Culture Collection, P.O. Box 1549, Manassas, Va. 20108) (see U.S. Pat. No. 6,692,741, the disclosure of which is incorporated herein by reference in its entirety, particularly at col. 3, lines 7-13, and at cols. 7-8).

In some embodiments, the antibodies comprise a heavy chain whose complementarity determining regions (CDR) 1, 2 and 3 consist essentially (i.e., with the exception of some conservative variations) of the sequences shown in Table 1 below. In certain such embodiments, the antibodies comprise a heavy chain whose CDR1 consists essentially of any one of SEQ ID NOs:1-5; whose CDR2 consists essentially of any one of SEQ ID NOs: 6-11; and whose CDR3 consists essentially of any one of SEQ ID NOs:12-17; and/or a light chain whose CDRs 1, 2 and 3 consist essentially of any one of the sequences of SEQ ID NOs:18-23, 24-27, and 28-33, respectively.

TABLE 1

| Antibody | Amino Acid Sequence | SEQ ID NO: |
|---|---|---|
| | Heavy Chain CDR1 Sequences | |
| 8G6 | SYTFTDYAMH | 1 |
| 1A8 | SYTFTDYTMH | 2 |

TABLE 1-continued

| Antibody | Amino Acid Sequence | SEQ ID NO: |
|---|---|---|
| 2B1 | GFTFSRYVMS | 3 |
| 3G9 | GFTFSRYVMS | 3 |
| 2A1 | GYDFNNDLIE | 4 |
| 2G2 | GYAFTNYLIE | 5 |
| | Heavy Chain CDR2 Sequences | |
| 8G6 | VISTYYGNTNYNQKFKG | 6 |
| 1A8 | VIDTYYGKTNYNQKFEG | 7 |
| 2B1 | SISSG-GSTYYPDSVKG | 8 |
| 3G9 | SISSG-GRMYYPDTVKG | 9 |
| 2A1 | VINPGSGRTNYNEKFKG | 10 |
| 2G2 | VISPGSGIINYNEKFKG | 11 |
| | Heavy Chain CDR3 Sequences | |
| 8G6 | GGLRRGDRPSLRYAMDY | 12 |
| 1A8 | GGFRRGDRPSLRYAMDS | 13 |
| 2B1 | GAIYDG-----YYVFAY | 14 |
| 3G9 | GSIYDG-----YYVFPY | 15 |
| 2A1 | IYYGPH-----SYAMDY | 16 |
| 2G2 | ID-YSG-----PYAVDD | 17 |
| | Light Chain CDR1 Sequences | |
| 8G6 | RASQSVSTSS-YSYMY | 18 |
| 1A8 | RASQSVSIST-YSYIH | 19 |
| 2B1 | SASSSVSSS----YLY | 20 |
| 3G9 | SANSSVSSS----YLY | 21 |
| 2A1 | KASLDVRTAVA | 22 |
| 2G2 | KASQAVNTAVA | 23 |
| | Light Chain CDR2 Sequences | |
| 8G6 | YASNLES | 24 |
| 1A8 | YASNLES | 24 |
| 2B1 | STSNLAS | 25 |
| 3G9 | STSNLAS | 25 |
| 2A1 | SASYRYT | 26 |
| 2G2 | SASYQYT | 27 |
| | Light Chain CDR3 Sequences | |
| 8G6 | QHNWEIPFT | 28 |
| 1A8 | QHSWEIPYT | 29 |
| 2B1 | HQWSSYPPT | 30 |
| 3G9 | HQWSTYPPT | 31 |
| 2A1 | QQHYGTPWT | 32 |
| 2G2 | QHHYGVPWT | 33 |

In other related embodiments, the monoclonal antibodies used in accordance with the present invention are chimeric antibodies, i.e., those in which a cognate antibody from one species (e.g., murine, rat or rabbit) is altered by recombinant DNA technology such that part or all of the hinge and/or constant regions of the heavy and/or light chains are replaced with the corresponding components of an antibody from another species (e.g., human). Generally, the variable domains of the engineered antibody remain identical or substantially so to the variable domains of the cognate antibody. Such an engineered antibody is called a chimeric antibody and is less antigenic than the cognate antibody when administered to an individual of the species from which the hinge and/or constant region is derived (e.g., a human). Methods of making chimeric antibodies are well known in the art.

In other related embodiments, the monoclonal antibodies used in accordance with the present invention are fully human antibodies. Methods for producing such fully human monoclonal antibodies are well known in the art (see, e.g., U.S. 2005/0255102 A1 at page 4, paragraphs 0069-0070, which are incorporated herein by reference).

In other related embodiments, the monoclonal antibodies used in accordance with the present invention are humanized versions of cognate anti-$\alpha_{84}$ $\beta_6$ antibodies derived from other species. A humanized antibody is an antibody produced by recombinant DNA technology, in which some or all of the amino acids of a human immunoglobulin light or heavy chain that are not required for antigen binding (e.g., the constant regions and the framework regions of the variable domains) are used to substitute for the corresponding amino acids from the light or heavy chain of the cognate, nonhuman antibody. By way of example, a humanized version of a murine antibody to a given antigen has, on both of its heavy and light chain: (a) constant regions of a human antibody, (b) framework regions from the variable domains of a human antibody; and (c) CDRs from the murine antibody. When necessary, one or more residues in the human framework regions can be changed to residues at the corresponding positions in the murine antibody so as to preserve the binding affinity of the humanized antibody to the antigen. This change is sometimes called "back mutation." Humanized antibodies generally are less likely to elicit an immune response in humans as compared to chimeric human antibodies because the former contain considerably fewer non-human components. Methods for producing such humanized monoclonal antibodies are well known in the art (see, e.g., U.S. 2005/0255102 A1 at pages 4-5, paragraphs 0072-0077, which are incorporated herein by reference).

In additional such embodiments, the humanized antibodies comprise one or more CDRs in the heavy and/or light chain that are derived from the corresponding CDRs in the heavy and/or light chain of a different antibody. One suitable non-limiting example of such an antibody is a humanized 3G9 antibody comprising a light chain CDR1 that has the sequence of the light chain CDR1 derived from the 2B1 antibody (SEQ ID NO:20) instead of the sequence of the light chain CDR1 for the deposited 3G9 antibody (SEQ ID NO:21). Such a humanized 3G9 antibody having a light chain CDR1 sequence set forth in SEQ ID NO:20 is designated herein as hu3G9 (or BG00011). Another suitable non-limiting example of such an antibody is a humanized 8G6 antibody comprising a light chain CDR1 that has the sequence of the light chain CDR1 derived from the 2B1 antibody (SEQ ID NO:20) instead of the sequence of the light chain CDR1 for the deposited 8G6 antibody (SEQ ID NO: 18) Such a humanized 8G6 antibody having a light chain CDR1 sequence set forth in SEQ ID NO:20 is designated herein as hu8G9. Additional examples of such derivative antibodies, in which one or more heavy chain and/or light chain CDRs has been replaced with one or more corresponding heavy chain and/or light chain CDRs from another antibody, and which are suitable for use in accordance with the present invention, will be readily apparent to those of ordinary skill in view of the sequences depicted in Table 1 and the guidance provided herein. Suitable methods for preparing such humanized antibodies, including such derivative humanized antibodies, are familiar to those of ordinary skill and are set forth, for example, in U.S. published application no. 2005/0255102 A1, the disclosure of which is incorporated herein by reference in its entirety.

In certain embodiments, the ligands, e.g., the antibodies, that bind to $\alpha_v\beta_6$ can be used in unconjugated form. In such embodiments, the tumor cells are contacted with the ligand binding to $\alpha_v\beta_6$, under conditions favoring binding of the ligand to $\alpha_v\beta_6$ on the cell surface. Suitable such conditions are well-known in the art, and are described in detail in the Examples hereinbelow. In certain such embodiments, the binding of the ligand sensitizes the tumor cell to which the ligand has bound to the action of one or more toxic compounds, i.e., the binding of the ligand to $\alpha v\beta 6$ on the tumor cell surface induces the tumor cell to become more sensitive to the growth-inhibiting and/or death-inducing actions of one or more toxins Thus, in additional embodiments, the invention provides methods of inhibiting the growth of a tumor cell, or of killing a tumor cell, comprising (a) contacting the tumor cell with one or more ligands (e.g., one or more antibodies or fragments thereof that bind to $\alpha_v\beta_6$ on the cell surface, under conditions favoring the binding of the ligand $\alpha_v\beta_6$ on the cell surface; and then (b) contacting the tumor cell with one or more toxic compounds that inhibits the growth of and/or kills the tumor cell. Suitable toxic compounds for use in accordance with this aspect of the invention, and appropriate dosages and administration regimens therefor, are known in the art and are described in detail elsewhere herein.

In related embodiments, the invention provides methods of sensitizing tumor cells to one or more toxic compounds by treating the tumor cells with one or more agents that modulates (e.g., inhibits or activates) one or more components of the TGF-β signaling pathway. Suitable such agents include, for example, TGF-β or a fragment thereof, a soluble TGF-β receptor or a fragment thereof, or a fusion protein comprising a soluble TGF-β receptor or a fragment thereof (e.g., a TGF-β type II receptor fragment fused to the Fc region of an antibody, to produce a soluble "TGF-β RII-Fc" polypeptide). In use, the binding or internalization of the TGF-β-modulating agent sensitizes the tumor cell by which the agent has been bound or internalized to the action of one or more toxic compounds, i.e., induces the tumor cell to become more sensitive to the growth-inhibiting and/or death-inducing actions of one or more toxins. Thus, in additional embodiments, the invention provides methods of inhibiting the growth of a tumor cell, or of killing a tumor cell, comprising (a) contacting the tumor cell with one or more agents that modulates (e.g., inhibits or activates) one or more components of the TGF-β signaling pathway, under conditions favoring the binding or internalization of the agent by the tumor cell; and then (b) contacting the tumor cell with one or more toxic compounds that inhibits the growth of and/or kills the tumor cell. Suitable toxic compounds for use in accordance with this aspect of the invention, and appropriate dosages and administration regimens therefor, are known in the art and are described in detail elsewhere herein.

Conjugates an Other Modifications of $\alpha_v\beta_6$-Binding Ligands

As noted above, in certain embodiments, the ligands, e.g., the antibodies, that bind to $\alpha_v\beta_6$ can be used in unconjugated form. In other embodiments, the ligands, e.g., the antibodies, that bind to $\alpha_v\beta_6$ can be conjugated, e.g., to a detectable label, a drug, a prodrug or an isotope.

In certain methods of the invention described in more detail below, such as methods of detecting $\alpha_v\beta_6$ expression in cells or tissues in conjunction with detection of smad4 expression as a measure of the potential of tumor cells to be responsive to $\alpha_v\beta_6$-binding ligands and/or TGF-β-blocking agents, the $\alpha_v\beta_6$-binding ligands (e.g., antibodies) are conjugated to one or more detectable labels. For such uses, the $\alpha_v\beta_6$-binding ligands, e.g., $\alpha_v\beta_6$-binding antibodies, may be detectably labeled by covalent or non-covalent attachment of a chromogenic, enzymatic, radioisotopic, isotopic, fluorescent, toxic, chemiluminescent, nuclear magnetic resonance contrast agent or other label.

Examples of suitable chromogenic labels include diaminobenzidine and 4-hydroxyazo-benzene-2-carboxylic acid.

Examples of suitable enzyme labels include malate dehydrogenase, staphylococcal nuclease, Δ-5-steroid isomerase, yeast-alcohol dehydrogenase, α-glycerol phosphate dehydrogenase, triose phosphate isomerase, peroxidase, alkaline phosphatase, asparaginase, glucose oxidase, β-galactosidasce, ribonuclease, urease, catalase, glucose-6-phosphate dehydrogenase, glucoamylase, and acetylcholine esterase.

Examples of suitable radioisotopic labels include $^{3}H$, $^{111}In$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope where in vivo imaging is used since its avoids the problem of dehalogenation of the $^{125}$I or $^{131}$I-labeled $\alpha_v\beta_6$-binding ligands by the liver. In addition, this radionucleotide has a more favorable gamma emission energy for imaging (Perkins et al., Eur. J. Nucl. Med. 10:296-301 (1985); Carasquillo et al., J. Nucl. Med. 28:281-287 (1987)). For example, $^{111}$In coupled to monoclonal antibodies with 1-(P-isothiocyanatobenzyl)-DPTA has shown little uptake in non-tumorous tissues, particularly the liver, and therefore enhances specificity of tumor localization (Esteban et al., J. Nucl. Med. 28:861-870 (1987)).

Examples of suitable non-radioactive isotopic labels include $^{157}$Gd, $^{55}$Mn, $^{162}$Dy, $^{52}$Tr, $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, a Green Fluorescent Protein (GFP) label, an o-phthaldehyde label, and a fluorescamine label. Examples of suitable toxin labels include diphtheria toxin, ricin, and cholera toxin.

Examples of chemiluminescent labels include a luminol label, an isoluminol label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to $\alpha_v\beta_6$-binding ligands, e.g., $\alpha_v\beta_6$-binding antibodies, are provided by Kennedy et al., Clin. Chim. Acta 70:1-31 (1976), and Schurs et al., Clin. Chim. Acta 81:1-40 (1977). Coupling techniques mentioned in the latter are the glutaraldehyde method, the periodate method, the dimaleimide method, the m-maleimidobenzyl-N-hydroxy-succinimide ester method, all of which methods are incorporated by reference herein.

For use in certain therapeutic approaches of the invention such as ablation of tumor cells, or prevention of tumor cell growth, invasion or metastasis, the $\alpha_v\beta_6$-binding ligands can be conjugated to one or more drugs, prodrugs or isotopes. Preferred such conjugates comprise one or more ligands, e.g., one or more antibodies or fragments, derivatives or variants thereof, that bind to $\alpha_v\beta_6$, conjugated to one or more cytotoxic agents; such conjugates are useful in the methods of treatment and prevention of tumor metastasis provided by the invention. According to certain such embodiments of the invention, the $\alpha_v\beta_6$-binding ligand, e.g., antibody, is conjugated to a cytotoxic agent. Cytotoxic, e.g., chemotherapeutic, agents useful in the generation of $\alpha_v\beta_6$-binding ligand-cytotoxic agent conjugates are well known in the art, and include but are not limited to cisplatin, carboplatin, oxaliplatin, paclitaxel, gemcitabine, adriamycin (doxorubicin), melphalan, methotrexate, 5-fluorouracil, etoposide, mechlorethamine, cyclophosphamide, bleomycin, a calicheamicin, a maytansine, a trichothene. Particularly suitable for use in accordance with this aspect of the invention are paclitaxel, gemcitabine and adriamycin (doxorubicin). Other chemotherapeutic agents suitable for use in accordance with this aspect of the invention are well-known and will be familiar to the ordinarily skilled artisan.

Thus, the use of conjugates of one or more $\alpha_v\beta_6$-binding ligand, e.g., one or more $\alpha_v\beta_6$-binding antibodies, and one or more small molecule toxins, such as paclitaxel, adriamycin (doxorubicin), gemcitabine, a calicheamicin, a maytansine (U.S. Pat. No. 5,208,020), a trichothene, and CC1065, is also contemplated herein. In one embodiment of the invention, the $\alpha_v\beta_6$-binding ligand is conjugated to one or more maytansine molecules (e.g. about 1 to about 10 maytansine molecules per $\alpha_v\beta_6$-binding ligand). Maytansine may, for example, be converted to May-SS-Me which may be reduced to May-SH3 and reacted with modified $\alpha_v\beta_6$-binding ligands (Chari et al. Cancer Research 52: 127-131 (1992)) to generate a maytansinoid-$\alpha_v\beta_6$-binding ligand conjugate.

Alternatively, the $\alpha_v\beta_6$-binding ligand can be conjugated to one or more calicheamicin molecules. The calicheamicin family of antibiotics are capable of producing double-stranded DNA breaks at sub-picomolar concentrations. Structural analogues of calicheamicin which may be used include, but are not limited to, $\gamma_1^I$, $\alpha_2^I$, $\alpha_3^I$, N-acetyl-$\gamma_1^I$, PSAG and $\Phi_1^I$ (Hinman et al. Cancer Research 53: 3336-3342 (1993) and Lode et al. Cancer Research 58: 2925-2928 (1998)).

Enzymatically active toxins and fragments thereof which can be used to produce conjugates with one or more $\alpha_v\beta_6$-binding ligands, e.g., one or more $\alpha_v\beta_6$-binding antibodies, include diphtheria A chain, nonbinding active fragments of diphtheria toxin, exotoxin A chain (from Pseudomonas aeruiginosa), ricin A chain, abrin A chain, modeccin A chain, alpha-sarcin, Aleuiritesfordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published in the English language on Oct. 28, 1993, the disclosure of which is incorporated herein by reference in its entirety. Mytansinoids may also be conjugated to one or more αvβ6-binding ligands, e.g., one or more $\alpha_v\beta_6$-binding antibodies. The present invention further contemplates $\alpha_v\beta_6$-binding ligands conjugated with a compound with nucleolytic activity (e.g., a ribonuclease or a DNA endonuclease such as a deoxyribonuclease; DNase).

A variety of radioactive isotopes are also available for the production of radioconjugated $\alpha_v\beta_6$-binding ligands for use in therapeutic methods of the invention. Examples include $^{211}$At, $^{131}$I, $^{125}$I, $^{90}$Y, $^{186}$Re, $^{188}$Re, $^{153}$Sm, $^{212}$Bi, $^{32}$P and radioactive isotopes of Lu.

Conjugates of the $\alpha_v\beta_6$-binding ligands and cytotoxic agents may be made using a variety of bifunctional protein coupling agents such as N-succinimidyl-3-(2-pyridyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), his-azido compounds (such as bis(p-azidobenzoyl) hexanediamine), bis-diazonium derivatives (such as bis-(p-diazoniumbenzoyl)-ethylenediamine), diusocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). $^{14}$Carbon-labeled 1-isothiocyanatobenzyl-3-methyldiethylene triaminepentaacetic acid (MX-DTPA) is an exemplary chelating agent for conjugation of radionucleotide to the $\alpha_v\beta_6$-binding ligand. See WO 94/11026. The linker may be a "cleavable linker" facilitating release of the cytotoxic drug in the cell. For example, an acid-labile linker, peptidase-sensitive linker, dimethyl linker or disulfide-containing linker (Chari et al. Cancer Research 52:127-131 (1992)) may be used.

Alternatively, a fusion protein comprising the αvβ6-binding ligand and cytotoxic agent may be made, e.g. by recombinant techniques or peptide synthesis.

In yet another embodiment, the $\alpha_v\beta_6$-binding ligand may be conjugated to a "receptor" (such streptavidin) for utilization in "pretargeting" wherein the $\alpha_v\beta_6$-binding ligand-receptor conjugate is administered to the patient, followed by removal of unbound conjugate from the circulation using a clearing agent and then administration of a "ligand" (e.g. avidin) which is conjugated to a cytotoxic agent (e.g., a radionucleotide).

The $\alpha_v\beta_6$-binding ligands of the present invention may also be conjugated with a prodrug-activating enzyme which converts a prodrug (e.g. a peptidyl chemotherapeutic agent, see WO 81/01145) to an active drug. See, for example, WO 88/07378 and U.S. Pat. No. 4,975,278. The enzyme component of such conjugates includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as Serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as O-galactosidase and neuraminidase useful for converting glycosylated prodrugs into free drugs; P-lactamase useful for converting drugs derivatized with P-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs.

Enzymes can be covalently bound to the $\alpha_v\beta_6$-binding ligand by techniques well known in the art such as the use of the heterobifunctional crosslinking reagents. Alternatively, fusion proteins comprising at least the antigen binding region of a $\alpha_v\beta_6$-binding ligand of the invention linked to at least a functionally active portion of an enzyme can be constructed using recombinant DNA techniques well known in the art (see, e.g., Neuberger et al., Nature 312: 604-608 (1984)).

Disease Diagnosis and Prognosis

As noted above, it has now been found that cells from certain tumors that display significantly decreased levels of smad4 gene expression and significantly enhanced levels of integrin $\alpha_v\beta_6$ are more likely to be responsive to ligands that bind to $\alpha_v\beta_6$, and to agents that block one or more components of the TGF-β signalling pathway, when compared to cells that are display higher levels of smad4 gene expression. Thus, in one aspect, the invention provides a method useful in determining the likelihood of a tumor cell to respond to or to be chemosensitized by treatment with anti-αvβ6 ligands (e.g., antibodies) or with TGF-β-blocking agents, including tumors from carcinomas such as an adenocarcinoma. In more particular embodiments, the carcinoma is a pancreatic carcinoma, a colorectal carcinoma, a cervical carcinoma, a squamous cell carcinoma (such as an esophageal carcinoma), a head and neck carcinoma, a liver carcinoma, an ovarian carcinoma and a lung carcinoma. More particularly, the carcinoma is a pancreatic carcinoma, a colorectal carcinoma, a cervical carcinoma, or a head and neck carcinoma.

Methods according to this aspect of the invention involve assaying the level of expression of smad4 in the tumor cells or in a tumor tissue sample, and comparing these expression levels with a standard smad4 expression level (e.g., in normal cells or tissues, preferably obtained from the same animal, such as a human patient), wherein a decrease in the expression of smad4 in a tumor or in the cells thereof indicates that the tumor is more likely to be responsive to the growth-inhibiting actions of anti-αvβ6 ligands (e.g., antibodies) or with TGF-β-blocking agents, or to be chemosensitized by such ligands and agents to subsequent (or simultaneous) co-treatment with one or more chemotherapeutic compounds or compositions. As noted above, decreased expression of smad4 in tumors is often associated with a poor patient prognosis, so the methods of the invention provide a way to rapidly diagnose and aggressively treat such tumors with compounds and compositions that are most likely to provide a specifically targeted therapeutic approach, and thereby providing for a more favorable clinical outcome for the patient.

By "assaying the levels of expression of smad4" is intended qualitatively or quantitatively measuring or estimating the levels of smad4 in a first biological sample (e.g., a tumor sample, a tissue biopsy or aspirate, etc.) either directly (e.g., by determining or estimating absolute level of expression of $\alpha_v\beta_6$ in the sample) or relatively (e.g., by comparing the level of expression of smad4 in a first biological sample to that in a second biological sample). Preferably, the level of smad4 in the first biological sample is measured or estimated and compared to that in a standard taken from a second biological sample obtained from an individual not having a cancer or pre-cancerous lesion. The levels of smad4 can be measured in a given cell, tissue, organ or biological sample according to art-known methods of measuring gene expression, including, for example, hybridization or PCR/RT-PCR detection of the smad4 gene using known genetic probes or primers (see, e.g., Maliekal, T. T. et al., Oncogene 22:4889-4897 (2003); Iacobuzio-Donahue, C. A. et al., Clin. Cancer Res. 10:1597-1604 (2004)), northern blotting (see, e.g., Yasutome, M. et al., Clin. Exper. Metast. 22:461-473 (2005)), and immunohistochemical analysis with anti-SMAD4 antibodies (see, e.g., Lüttges, J. et al., Am. J. Pathol. 158:1677-1683 (2001); Fukuchi, M. et al., Cancer 95:737-743 (2002); Subramanian, G. et al., Cancer Res. 64:5200-5211 (2004); Levy, L. and Hill, C. S., Mol. Cell. Biol. 25:8108-8125 (2005)). As will be appreciated by one of ordinary skill in the art, once a standard smad4 expression level is known for a given non-cancerous tissue, it can be used repeatedly as a standard for comparison.

Similarly, by "assaying the levels of expression of $\alpha_v\beta_6$" is intended qualitatively or quantitatively measuring or estimating the levels of $\alpha_v\beta_6$ in a first biological sample (e.g., a tumor sample, a tissue biopsy or aspirate, etc.) either directly (e.g., by determining or estimating absolute amount of $\alpha_v\beta_6$ in the sample) or relatively (e.g., by comparing the level of expression of $\alpha_v\beta_6$ in a first biological sample to that in a second biological sample). Preferably, the level of $\alpha_v\beta_6$ in the first biological sample is measured or estimated and compared to that in a standard taken from a second biological sample obtained from an individual not having a cancer or pre-cancerous lesion. As will be appreciated by one of ordinary skill in the art, once a standard $\alpha_v\beta_6$ expression level is known for a given non-cancerous tissue, it can be used repeatedly as a standard for comparison.

By "biological sample" is intended any biological sample obtained from an individual (such as a patient), cell line, tissue culture, or other source which may contain cells or cellular products such as extracellular matrix. Such biological samples include mammalian body tissues and cells, including leukocyte, ovary, prostate, heart, placenta, pancreas, liver, spleen, lung, breast, head and neck tissues (e.g., oral, pharyngeal, lingual and laryngeal tissues), squamous cells (e.g., esophageal), endometrium, colon (or colorectal), cervix, stomach and umbilical tissues which may express $\alpha_v\beta_6$.

Methods for obtaining tissue biopsies and body fluids from mammals are well known in the art. Preferred mammals include monkeys, apes, cats, dogs, cows, pigs, horses, rabbits and humans. Particularly preferred are humans.

Assaying $\alpha_v\beta_6$ expression levels in a biological sample can occur using any art-known method. Preferred for assaying $\alpha_v\beta_6$ expression levels in a biological sample are immunological techniques. For example, $\alpha_v\beta_6$ expression in tissues can be studied with classical immunohistological methods. In these, the specific recognition is provided by a primary ligand, e.g., an antibody (polyclonal or monoclonal), that binds to $\alpha_v\beta_6$. This primary ligand can be labeled, e.g., with a fluorescent, chemiluminescent, phosphorescent, enzymatic or radioisotopic label. Alternatively, these methods of the invention can use a secondary detection system in which a second ligand that recognizes and binds to the $\alpha_v\beta_6$-binding ligand, e.g., a so-called "secondary" antibody which recognizes and binds to a first $\alpha_v\beta_6$-binding antibody, is detectably labeled as described above. As a result, an immunohistological staining of tissue section for pathological examination is obtained. Alternatively, tissues and cell samples can also be extracted, e.g., with urea and neutral detergent, for the liberation of $\alpha_v\beta_6$ protein for Western-blot or dot/slot assay (Jalkanen, M., et al., J. Cell. Biol. 101:976-985 (1985); Jalkanen, M., et al., J. Cell. Biol. 105:3087-3096 (1987)) for direct quantitation, relative to a standard tissue or cell sample known to have lower levels of expression of $\alpha_v\beta_6$.

As noted above, the methods of the present invention are useful for detecting cancers in mammals, for determining the likelihood that a given tumor cell will be responsive to treatment and/or chemosensitization with anti-$\alpha v\beta 6$ ligands and/or with TGF-$\beta$), and for treating carcinomas of a variety of types. In particular the methods of the invention are useful in detecting and/or treating cancers of epithelial tissues (i.e., carcinomas), including of the pancreas, colon/rectum, cervix, esophagus (and other squamous epithelial tissues), head and neck, liver, ovary and lung. Particularly amenable to detection by the methods of the present invention are invasive and/or metastatic adenocarcinomas, including but not limited to pancreatic carcinomas, colorectal carcinomas, cervical carcinomas, and head and neck carcinomas. Early identification and treatment of such carcinomas is associated with a better long-term prognosis for patients. For example, it has been reported that if left untreated, a significant proportion of noninvasive breast tumors become invasive and can lead to metastatic cancers which have a much poorer prognosis (see Sakorafas, G. H., and Tsiotou, A. G. H., Cancer Treatment Rev. 26:103-125 (2000)). In addition, as noted above, reduced expression of smad4 in primary pancreatic adenocarcinomas has been associated with poor prognosis for patients having such tumors (Liu, F., Clin. Cancer Res. 7:3853-3856 (2001); Tascilar, M. et al., Clin. Cancer Res. 7:4115-4121 (2001); Toga, T. et al., Anticancer Res. 24:1173-1178 (2004)). Thus, early diagnosis and initiation of treatment, preferably according to the methods described herein, is key to long-term survival of patients having smad4-deficient cancers.

Accordingly, the present invention contemplates methods of treating or preventing cancers by identifying smad4-deficient pre-cancerous lesions or carcinomas in patients, and treating the patient to eliminate the pre-cancerous lesion before it has the opportunity to evolve into a more advance form of cancer. Such methods comprise, for example, (a) obtaining a tissue sample that is suspected of containing a cancer or a pre-cancerous lesion, and a tissue sample that does not contain a cancer or pre-cancerous lesion (preferably from the same tissue or organ as that suspected of containing a cancer or pre-invasive lesion); and (b) determining the level of smad4 expression in the tumor or tissue samples, or cells therefrom, wherein a decrease in the level of smad4 expression in the tissue sample containing the cancerous or pre-invasive lesion, relative to the levels of smad4 expression in the non-cancerous tissue sample (or cells thereof), is indicative of a cancer or a precancerous lesion that is more likely to progressive to a more invasive or aggressive form of cancer. In other related embodiments, the invention contemplates methods of reducing or preventing the progression of a pre-cancerous lesion to a tumor in a patient, comprising identifying in a patient tumors (or cells thereof) that have a reduced level of smad4 expression (preferably using the methods described hereinabove), and administering to the patient a therapeutically effective amount of one or more ligands that binds to one or more subunits of integrin $\alpha_v\beta_6$ on one or more cells in the pre-cancerous, wherein the binding of the ligand to the integrin results in the death or inhibition of growth of the pre-cancerous lesion, or in the chemosensitization of the pre-cancerous lesion to the death-inducing or growth-inhibiting actions of one or more chemotherapeutic compounds.

Suitable tissues and organs from which samples can be obtained for use in accordance with these methods of the invention include, but are not limited to, the epithelial tissues described elsewhere herein. Cancers and tumors that may be advantageously treated or prevented according to such methods of the invention include, but are not necessarily limited to, carcinomas, particularly adenocarcinomas, including the carcinomas and adenocarcinomas described in detail elsewhere herein. Once such a carcinoma has been detected according to the methods of the invention, it can then be eliminated from the patient via surgical, chemotherapeutic, radiological or other methods of cancer therapy that are well-known in the art and that therefore will be familiar to those of ordinary skill. Alternatively, such a carcinoma can be eliminated using the methods of treatment of the present invention, by administering to the patient, or to the organs or tissues of the patient, one or more $\alpha_v\beta_6$-binding ligands, such as one or more $\alpha_v\beta_6$-binding antibodies or fragments thereof. In certain non-limiting examples of such embodiments, the one or more $\alpha_v\beta_6$-binding ligands have been conjugated with one or more cytotoxic compounds or agents as described in detail hereinabove. In additional non-limiting examples of such embodiments, the one or more $\alpha_v\beta_6$-binding ligands, such as one or more $\alpha_v\beta_6$-binding antibodies or fragments thereof, are administered to a subject, such as a patient, in conjunction with one or more cytotoxic compounds or agents as described in detail hereinabove. In other related embodiments, such methods of the invention comprise administering one or more TGF-$\beta$-blocking agents, such as those described herein, which inhibit the growth of the tumor cells and/or chemosensitize the tumor cells to the actions of one or more toxic chermotherapeutic compounds.

In related embodiments, the invention contemplates determining the metastatic potential of a tumor or cancer cell by measuring the levels of expression of smad4 and $\alpha_v\beta_6$ by the tumor or cancer cell. In such embodiments, tumor or cell samples are obtained from a patient as described above and are assayed according to the methods described herein for the levels of expression of smad4 and $\alpha_v\beta_6$ by the tumor or cancer cell. According to these methods of the invention, there is an inverse correlation between the level of expression of smad4 by the tumor or cancer cell and the level of expression of $\alpha_v\beta_6$ by the tumor or cancer cell that provides a useful clinical picture that can be used to determine the metastatic potential of a tumor or cancer cell. Specifically, a decrease in the expression of smad4 by a tumor or cancer cell and a concomitant increase in the expression of $\alpha_v\beta_6$ by the tumor or cancer cell direct correlation between the level of expression of $\alpha_v\beta_6$ by the tumor or cancer cell indicates that that tumor or cancer cell is more likely to metastasize to a secondary locus from the primary tumor site. Hence, the levels of expression of smad4 and of $\alpha_v\beta_6$ by a tumor or cancer cell can be used as a prognostic indicator of the metastatic potential of a tumor or cancer cell, which can assist cancer patients and their physicians in making appropriate treatment decisions based on the present or predicted future aggressiveness or invasiveness of the cancer.

In addition to assaying smad4 and $\alpha_v\beta_6$ expression levels in a biological sample obtained from an individual, such as a tissue or tumor cell sample, the level and pattern of expression of $\alpha_v\beta_6$ can also be detected in vivo by imaging. In such methods of the invention, one or more SMAD4-binding ligands and $\alpha_v\beta_6$-binding ligands, e.g., one or more SMAD4-binding antibodies and one or more $\alpha_v\beta_6$-binding antibodies, are detectably labeled with one or more labels suitable for in vivo imaging. Suitable labels or markers for in vivo imaging include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium.

A ligand binding to SMAD4 or $\alpha_v\beta_6$, e.g., a SMAD4– or an $\alpha_v\beta_6$-binding antibody or antibody fragment, which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for cancer or carcinoma in situ. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled ligand, e.g., SMAD4– or $\alpha_v\beta_6$-binding antibody or antibody fragment, will then preferentially accumulate at the location of cells or tissues which contain or express SMAD4 or $\alpha_v\beta_6$ integrin. In vivo tumor imaging is then accomplished as described in S. W. Burchiel et al., "Immunopharmacokinetics of Radiolabelled Antibodies and Their Fragments" (Chapter 13 in Tumor Imaging: The Radiochemical Detection of Cancer, S. W. Burchiel and B. A. Rhodes, eds., Masson Publishing Inc. (1982)).

Therapeutic Methods

In additional embodiments of the invention, the methods of the present invention can be used therapeutically regimens for treating mammals afflicted with certain diseases, particularly with certain carcinomas such as those described elsewhere herein. Such methods of the invention are useful in treating cancer and associated events, including tumor growth, metastasis and angiogenesis. Particularly amenable to such an approach are those diseases or cancers that are characterized by decreased levels of smad4 expression, and concomitantly increased levels of $\alpha_v\beta_6$ expression, in the tissues or cells of a mammal suffering from the disease, and which are responsive to treatments which target the tissues or cells expressing increased levels of $\alpha_v\beta_6$ and eliminate those tissues or cells. Methods according to this aspect of the invention comprise, for example, (a) identifying tumors or tumor cells with decreased smad4 expression in a patient, and (b) treating the patient with one or more $\alpha_v\beta_6$-binding ligands, such as one or more $\alpha_v\beta_6$-binding antibodies or fragments thereof, or with one or more TGF-β-blocking agents or fragments thereof. Alternative such methods comprise, for example, (a) identifying tumors or tumor cells with decreased smad4 expression in a patient; (b) treating the patient with one or more $\alpha_v\beta_6$-binding ligands, such as one or more $\alpha_v\beta_6$-binding antibodies or fragments thereof, or with one or more TGF-β-blocking agents or fragments thereof, wherein the binding of the $\alpha_v\beta_6$-binding ligands or the TGF-β-blocking agents to the tumor cells chemosensitizes the tumor cells to the growth-inhibiting and/or death-inducing actions of one or more chemotherapeutic compounds; and (c) treating the patient with one or more chemotherapeutic compounds that inhibits the growth of, or kills, the tumor cells.

Diseases that are particularly treatable by these methods include metastatic cancers of epithelial tissues (i.e., metastatic carcinomas and/or adenocarcinomas), including of the pancreas, colon/rectum, cervix, esophagus (and other squamous epithelial tissues and organs), head and neck, liver, ovary and lung. Particularly suitable for treatment by these methods of the present invention are carcinomas of the pancreas, colon/rectum, cervix, head and neck and esophagus. Preferred mammals for treatment include monkeys, apes, cats, dogs, cows, pigs, horses, rabbits and humans. Particularly preferred are humans.

In related embodiments, as described above, the invention provides methods of reducing or preventing the progression of a pre-metastatic tumor to a metastatic tumor in a patient, comprising administering to the patient a therapeutically effective amount of one or more ligands that binds to one or more subunits of integrin $\alpha_v\beta_6$ on one or more cells in the pre-metastatic tumor, wherein the binding of the ligand to the integrin results in the reduction or prevention of invasion of cells of the pre-metastatic cancer into tissue areas surrounding the primary tumor.

In carrying out these therapeutic methods of the invention, $\alpha_v\beta_6$-binding ligands, such as $\alpha_v\beta_6$-binding antibodies or fragments thereof, or TGF-β-blocking agents or fragments thereof, may be administered to patients in the form of therapeutic formulations (which are also referred to herein interchangeably and equivalently as pharmaceutical compositions). Therapeutic formulations of the $\alpha_v\beta_6$-binding ligands or TGF-β-blocking agents or fragments thereof used in accordance with the present invention are prepared for storage by mixing a $\alpha_v\beta_6$-binding ligand or TGF-β-blocking agent or fragment thereof having the desired degree of purity with optional pharmaceutically acceptable carriers, excipients or stabilizers (Remington's Pharmaceutical Sciences 16th edition, Osol, A. Ed. (1980)), for example in the form of lyophilized formulations or aqueous solutions. In addition to the pharmacologically active compounds such as the $\alpha_v\beta_6$-binding ligands or the TGF-β-blocking agents or fragments thereof, the compositions used in the therapeutic methods of the invention can contain one or more suitable pharmaceutically acceptable carriers comprising excipients and auxiliaries that facilitate processing of the active compounds into preparations that can be used pharmaceutically. The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as starch paste, using, for example, maize starch, wheat starch, rice starch, potato starch, gelatin, tragacanth, methyl cellulose, hydroxypropylmethylcellulose, sodium carboxy-methylcellulose, and/or polyvinyl pyrrolidone. If desired, disintegrating agents can be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example silica, talc, stearic acid or salts thereof, such as magnesium stearate or calcium stearate, and/or polyethylene glycol. Dragee cores are provided with suitable coatings, that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethylcellulose phthalate, are used. Dye stuffs or pigments can be added to the tablets or dragee coatings, for example, for identification or in order to characterize combinations of active compound doses.

Other pharmaceutical preparations that can be used orally include push-fit capsules made of gelatin, as well as soft, sealed capsules made of gelatin and a plasticizer such as glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids such as fatty oils or liquid paraffin. In addition, stabilizers may be added.

Suitable formulations for parenteral administration include aqueous solutions of the active compounds in water-soluble form, for example water-soluble salts and alkaline solutions. Alkaline salts can include ammonium salts prepared, for example, with Tris, choline hydroxide, bis-Tris propane, N-methylglucamine, or arginine. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example sodium carboxymethyl cellulose, sorbitol, and/or dextran. Optionally, the suspension may also contain stabilizers.

The compounds of the present invention may be administered to the eye in animals and humans as a drop, or within ointments, gels, liposomes, or biocompatible polymer discs, pellets or carried within contact lenses. The intraocular composition may also contain a physiologically compatible ophthalmic vehicle as those skilled in the art can select using conventional criteria. The vehicles may be selected from the known ophthalmic vehicles which include but are not limited to water, polyethers such as polyethylene glycol 400, polyvinyls such as polyvinyl alcohol, povidone, cellulose derivatives such as carboxymethylcellulose, methylcellulose and hydroxypropyl methylcellulose, petroleum derivatives such as mineral oil and white petrolatum, animal fats such as lanolin, vegetable fats such as peanut oil, polymers of acrylic acid such as carboxylpolymethylene gel, polysaccharides such as dextrans and glycosaminoglycans such as sodium chloride and potassium, chloride, zinc chloride and buffer such as sodium bicarbonate or sodium lactate. High molecular weight molecules can also be used. Physiologically compatible preservatives which do not inactivate the compounds of the present invention in the composition include alcohols such as chlorobutanol, benzalkonium chloride and EDTA, or any other appropriate preservative known to those skilled in the art.

Lyophilized formulations of antibodies adapted for subcutaneous administration are described in U.S. Pat. No. 6,267,958, the disclosure of which is incorporated herein by reference in its entirety. Such lyophilized formulations may be reconstituted with a suitable diluent to a high protein concentration and the reconstituted formulation may be administered subcutaneously to the patient to be treated herein.

The $\alpha_v\beta_6$-binding ligands may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of $\alpha_v\beta_6$-binding ligands may be prepared. Suitable examples of sustained-release preparations include semipermeable matrices of solid hydrophobic polymers containing the $\alpha_v\beta_6$-binding ligand, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

The $\alpha_v\beta_6$-binding ligand or TGF-β-blocking agents or fragments thereof may be administered to the subject or patient by any suitable means, including parenteral, intrapulmonary, intracranial, transdermal and intranasal. Parenteral infusions include intramuscular, intravenous, intraarterial, intraperitoneal, or subcutaneous administration. In addition, the $\alpha_v\beta_6$-binding ligand or TGF-β-blocking agents or fragments thereof may suitably be administered by pulse infusion, e.g., with declining doses of the $\alpha_v\beta_6$-binding ligand or TGF-β-blocking agent or fragments thereof. Preferably the dosing is given by injections, most preferably intravenous or subcutaneous injections, depending in part on whether the administration is brief or chronic.

In certain exemplary embodiments of the invention, the $\alpha_v\beta_6$-binding ligands or TGF-β-blocking agents or fragments thereof are administered to the patient (e.g., intravenously) in a dosage of between about 1 mg/m$^2$ and about 500 mg/m$^2$. For instance, the $\alpha_v\beta_6$-binding ligand or TGF-β-blocking agent or fragments thereof may be administered in a dosage of about 1 mg/m$^2$, 2 mg/m$^2$, 3 mg/m$^2$, 4 mg/m$^2$, 5 mg/m$^2$, 10 mg/m$^2$, 15 mg/m$^2$, 20 mg/m$^2$, 25 mg/m$^2$, 30 mg/m$^2$, 35 mg/m$^2$, 40 mg/m$^2$, 45 mg/m$^2$, 50 mg/m$^2$, 55 mg/m$^2$, 60 mg/m$^2$, 65 mg/m$^2$, 70 mg/m$^2$, 75 mg/m$^2$, 80 mg/m$^2$, 85 mg/m$^2$, 90 mg/m$^2$, 95 mg/m$^2$, 100 mg/m$^2$, 105 mg/m$^2$, 110 mg/m$^2$, 115 mg/m$^2$, 120 mg/m$^2$, 125 mg/m$^2$, 130 mg/m$^2$, 135 mg/m$^2$, 140 mg/m$^2$, 145 mg/m$^2$, 150 mg/m$^2$, 155 mg/m$^2$, 160 mg/m$^2$, 165 mg/m$^2$, 170 mg/m$^2$, 175 mg/m$^2$, 180 mg/m$^2$, 185 mg/m$^2$, 190 mg/m$^2$, 195 mg/m$^2$, 200 mg/m$^2$, 205 mg/m$^2$, 210 mg/m$^2$, 215 mg/m$^2$, 220 mg/m$^2$, 225 mg/m$^2$, 230 mg/m$^2$, 235 mg/m$^2$, 240 mg/m$^2$, 245 mg/m$^2$, 250 mg/m$^2$, 255 mg/m$^2$, 260 mg/m$^2$, 265 mg/m$^2$, 270 mg/m$^2$, 275 mg/m$^2$, 280 mg/m$^2$, 285 mg/m$^2$, 290 mg/m$^2$, 295 mg/m$^2$, 300 mg/m$^2$, 305 mg/m$^2$, 310 mg/m$^2$, 315 mg/m$^2$, 320 mg/m$^2$, 325 mg/m$^2$, 330 mg/m$^2$, 335 mg/m$^2$, 340 mg/m$^2$, 345 mg/m$^2$, 350 mg/m$^2$, 355 mg/m$^2$, 360 mg/m$^2$, 365 mg/m$^2$, 370 mg/m$^2$, 375 mg/m$^2$, 380 mg/m$^2$, 385 mg/m$^2$, 390 mg/m$^2$, 395 mg/m$^2$ or 400 mg/m$^2$.

The $\alpha_v\beta_6$-binding ligand or TGF-β-blocking agents or fragments thereof can be administered according to a wide variety of dosing schedules. For example, the $\alpha_v\beta_6$-binding ligand or TGF-β-blocking agents or fragments thereof can be administered once daily for a predetermined amount of time (e.g., four to eight weeks, or more), or according to a weekly schedule (e.g., one day per week, two days per week, three days per week, four days per week, five days per week, six days per week or seven days per week) for a predetermined amount of time (e.g., four to eight weeks, or more). A specific example of a "once weekly" dosing schedule is administration of the $\alpha_v\beta_6$-binding ligand or TGF-β-blocking agents or fragments thereof on days 1, 8, 15 and 22 of the treatment period. In alternative embodiments the $\alpha_v\beta_6$-binding ligand or TGF-β-blocking agents or fragments thereof may be administered intermittently over a period of months. For example, the $\alpha_v\beta_6$-binding ligand or TGF-β-blocking agents or fragments thereof may be administered weekly for three consecutive weeks biannually (i.e., repeat the weekly dosing schedule every six months). It will be appreciated that such administration regimens may be continued for extended periods (on the order of years) to maintain beneficial therapeutic effects provided by initial treatments. In yet other embodiments such maintenance therapy may be effected following an acute dosing regimen designed to reduce the immediate symptoms of the cancerous, metastatic or in situ carcinoma condition.

The amount of $\alpha_v\beta_6$-binding ligand or TGF-β-blocking agents or fragments thereof administered each time throughout the treatment period can be the same; alternatively, the amount administered each time during the treatment period can vary (e.g., the amount administered at a given time can be more or less than the amount administered previously). For example, doses given during maintenance therapy may be lower than those administered during the acute phase of treatment. Appropriate dosing schedules depending on the specific circumstances will be apparent to persons of ordinary skill in the art.

In certain embodiments of the invention, multiple types or species of $\alpha_v\beta_6$-binding ligands are combined with one another and administered to a patient to treat one or more cancerous, metastatic or in situ carcinoma conditions. For example, the invention contemplates the administration of two or more different $\alpha_v\beta_6$-binding antibodies and/or TGF-β-blocking agents or fragments thereof to a patient, such as those disclosed herein. When multiple $\alpha_v\beta_6$-binding ligands and/or TGF-β-blocking agents or fragments thereof are administered to a patient, the different $\alpha_v\beta_6$-binding ligands and/or TGF-β-blocking agents or fragments thereof can be administered together in a single pharmaceutical composition, or, more preferably, can be administered sequentially in separate dosages. The effective amount of such other agents depends on the amount of $\alpha_v\beta_6$-binding ligand and/or TGF-β-blocking agents or fragments thereof present in the formulation, the type of disease or disorder or treatment, and other factors.

The present invention also includes methods for treating cancerous or metastatic conditions that comprise administering to a patient a first agent in conjunction with a second agent, wherein the first agent is a $\alpha_v\beta_6$-binding ligand and the second agent is an agent that is useful for treating one or more cancerous, metastatic or in situ carcinoma conditions but that is not necessarily a $\alpha_v\beta_6$-binding ligand. In other aspects, the invention provides methods for treating cancerous or metastatic conditions that comprise administering to a patient a first agent in conjunction with a second agent, wherein the first agent is a TGF-β-blocking agent or fragment thereof and the second agent is an agent that is useful for treating one or more cancerous, metastatic or in situ carcinoma conditions but that is not necessarily a TGF-β-blocking agent. By administering a first agent "in conjunction with" a second agent is meant that the first agent can be administered to the patient prior to, simultaneously with, or after, administering the second agent to the patient, such that both agents are administered to the patient during the therapeutic regimen. For example, according to certain such embodiments of the invention, a $\alpha_v\beta_6$-binding ligand is administered to a patient in conjunction (i.e., before, simultaneously with, or after) administration of an antagonist of one or more other integrin receptors (e.g., $\alpha_1\beta_1$, $\alpha_4\beta_1$, $\alpha_v\beta_8$, $\alpha_v\beta_5$, $\alpha_5\beta_1$, etc.) to the patient, including antibodies, polypeptide antagonists and/or small molecule antagonists specific for one or more integrin receptors (e.g., $\alpha_1\beta_1$, $\alpha_4\beta_1$, $\alpha_v\beta_8$, $\alpha_v\beta_5$, $\alpha_5\beta_1$, etc.) which are known in the art.

In certain embodiments of this aspect of the invention, the second agent that is administered in conjunction with an $\alpha_v\beta_6$-binding ligand or TGF-β-blocking agents or fragments thereof is, e.g., a steroid, a cytotoxic compound (including those described elsewhere herein, and particularly paclitaxel, gemicitabine or adriamycin (doxorubicin), a radioisotope (including those described elsewhere herein), a prodrug-activating enzyme (including those described elsewhere herein), colchicine, oxygen, an antioxidant (e.g., N-acetylcysteine), a metal chelator (e.g., terathiomolybdate), IFN-β, IFN-γ, alpha-antitrypsin and the like. Additional second agents or compounds that can be administered to a patient in conjunction with one or more first agents, such as one or more $\alpha_v\beta_6$-binding ligands, for therapeutic purposes according to this aspect of the invention, will be familiar to those of ordinary skill in the art; the use of such additional second agents or compounds is therefore considered to be encompassed by the present invention.

Diagnostic Kits

In additional embodiments, the present invention provides kits, particularly kits useful in diagnosis and/or prognosis of diseases or disorders such as cancers. Kits according to this aspect the present invention may comprise at least one container containing one or more of the above-described ligands, such as antibodies, that bind to or recognize integrin αvβ6. These kits of the invention may optionally further comprise at least one additional container which may contain, for example, a reagent (such as a buffered salt solution) for delivering the ligand (e.g., antibody) to a test sample such as an organ, tissue or cell sample from a patient; at least one additional container containing, for example, a reagent (including but not limited to the nucleic acid reagents described above) suitable for determining the expression of smad4 in a biological sample; TGF-β; one or more detergents, lysis agents, or other solutions suitable for preparation of a biological sample for testing; and the like. Other suitable additional components of such kits of the invention will be familiar to those of ordinary skill in the art.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

$\alpha_v\beta_6$ is Highly Expressed in Metastases Relative to Primary Tumors In the present experiments, we set out to study the expression of $\alpha_v\beta_6$ in a variety of cancers of epithelial origin and on metastatic lesions and to determine if function blocking $\alpha_v\beta_6$ mAbs could inhibit the growth of $\alpha_v\beta_6$ expressing tumors in vivo. We evaluated the in vitro and in vivo anti-tumor activity of our anti-human $\alpha_v\beta_6$ mAbs on a human pharyngeal carcinoma, Detroit62, and compared this to the in vivo anti-tumor activity of TGFβRII:Fc. Our data support a role in human cancer for $\alpha_v\beta_6$ and potential for therapeutic intervention with a function-blocking $\alpha_v\beta_6$ mAb.

A. Materials and Methods

For immunohistochemistry, tissue sections were deparaffinized in xylene and ethanol, rehydrated in distilled water, and then immersed in methanol containing 0.45% $H_2O$. Tissues were incubated with pepsin (00-3009, Zymed, San Francisco, Calif.) and blocked with avidin and biotin (SP-2001; Vector Laboratories, Burlingame, Calif.). Primary antibody was diluted in phosphate-buffered saline (PBS) containing 0.1% bovine serum albumin (BSA) and tissues were incubated overnight at 4° C. For immunostaining β6 on mouse xenograft tissue, sections were incubated with a human/mouse chimeric form of the anti-$\alpha_v\beta_6$ mAb, 2A1 (Weinreb, P. H. et al., J. Biol. Chem. 279(17):17875-17887 (2004)), and an anti-human biotinylated secondary antibody (PK-6103, Vector Laboratories, Burlingame, Calif.). For immunostaining $\beta_6$ on human tissue, sections were incubated with murine 2A1 and an anti-mouse-biotinylated secondary antibody (PK-6102, Vector Laboratories). Avidin-biotin complex-horseradish peroxidase (Vector Kit, PK-6102) was applied to sections, incubated for 30 minutes at room temperature, and 3,3'-diaminobenzidine (DAB) substrate was prepared as directed (SK-4100, Vector Laboratories) and applied to sections for five minutes at room temperature. Tissue sections were stained with Mayer's Hematoxylin for 1 minute and rinsed in water and PBS.

B. Results

1. $\alpha_v\beta_6$ Expression in Metastases $\alpha_v\beta_6$ immunostaining was evaluated on a variety of tumor metastases. 78% of the metastases (43/55) were positively immunostained showing intense staining over a majority of the metastases (FIGS. 1A-F; FIGS. 2A-I). This result was found to be an increase in percent positive immunostaining in that only head and neck, cervical and pancreatic tumors were found to have an equivalent level of expression (Table 2):

TABLE 2

$a_v\beta_6$ Expression in Human Tumors (immunohistochemistry)

| Tissue | $\alpha_v\beta_6^+$/total | % $\alpha_v\beta_6^+$ |
|---|---|---|
| Oral | 4/4 | 100% |
| Cervical | 79/98 | 81% |
| Pancreas | 31/39 | 80% |
| Skin | 41/53 | 77% |
| Larynx & pharynx | 43/64 | 67% |
| Esophageal | 35/56 | 63% |
| Endometrium | 17/32 | 53% |
| Lung | 28/70 | 40% |
| Breast | 41/101 | 41% |
| Colorectal | 181/488 | 37% |

Figure 4:
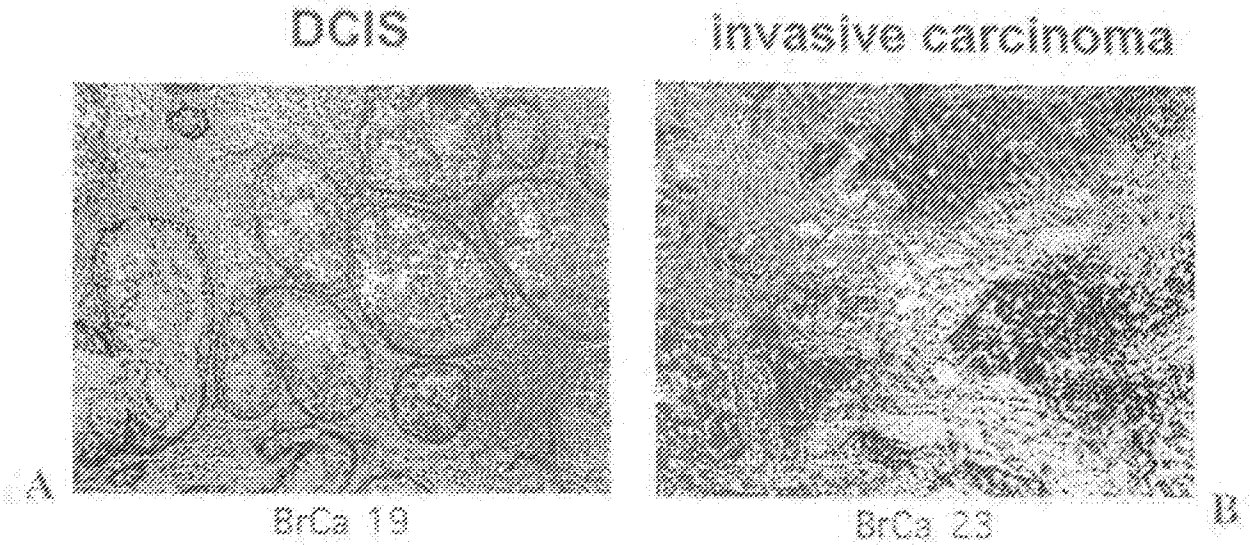
FIG. 4 is a composite of photomicrographs depicting the levels of αvβ6 expression (dark areas) observed in matched samples of primary and metastic pancreatic ductal adenocarcinoma tumors from three different patients.
Figure 5:
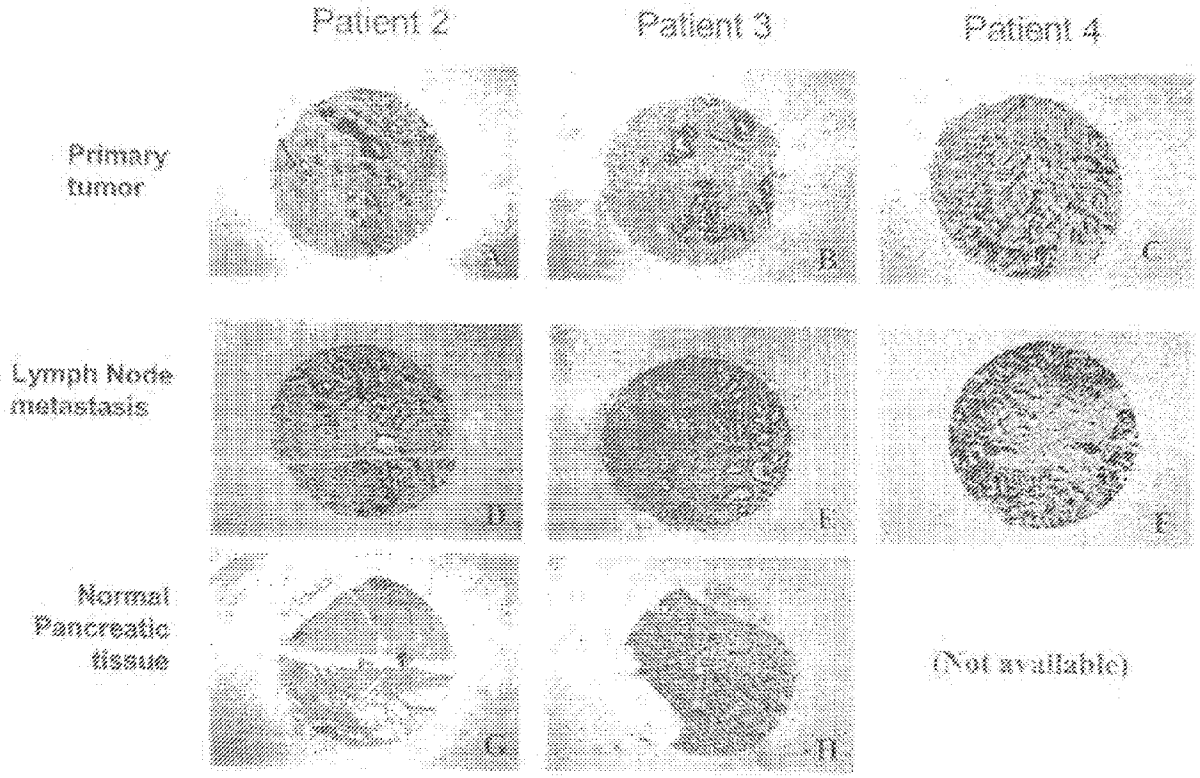
FIG. 5 is a composite of photomicrographs depicting the levels of αvβ6 expression (dark areas) observed in matched samples of primary and metastatic pancreatic adenocarcinoma tumors from five different patients.

2. $\alpha_v\beta_6$ Expression in Human Pancreatic Tumor Samples, Patient-Matched Metastases and Mouse Xenograft Model of Invasive Pancreatic Tumor As noted above in Table 2, $\alpha_v\beta_6$ immunostaining was positive on 80% of pancreatic tumors examined. When samples from primary pancreatic tumors from eight different patients were examined by immunohistochemistry, staining was prominent in invasive regions of high grade tumors (FIGS. 4A-4C; 5A-5E). The primary tumor samples also had matched lymph node metastases (FIGS. 4D-4F; 5F-5J), which also demonstrated strong $\alpha_v\beta_6$ staining, supporting the notion that $\alpha_v\beta_6$-positive cells have disseminated from the primary tumor site. In normal pancreas (FIGS. 4G-4H; 5A-5E), staining was confined to occasional cells on the surface layer.

To further examine the influence of $\alpha_v\beta_6$ expression on tumor cell invasion, we used a BxPC-3 mouse tumor xenograft as a model of invasive human pancreatic adenocarcinoma. Animals were implanted (day 0) subcutaneously on the flank with $5\times10^6$ cells/mouse, suspended in sterile saline, using a injection of 0.1 ml/mouse. At day 30, mice with established tumors (~60-100 $mm^3$) were pair-matched to each of three treatment groups (PBS; mAb 3G9; soluble TGF-β receptor II-Ig fusion protein (solTGFβRII -Fc)) for all studies. Test agents were administered to mice intraperitoneally on a 3 times per week treatment schedule. Mice were injected with 3G9 at 10 mg/kg, solTGFβRII-Fc at 2 mg/kg, or PBS (negative control). Tumor growth was measured twice a week and tumor volume estimated according to the formula: $[(\text{width})^2\times\text{length}]/2$. Tumors from treatment groups were excised, fixed in 10% paraformaldehyde, paraffin-embedded and sectioned for immunohistochemical analysis using the non-blocking v6 chimeric mAb 6.2A1.

Figure 6:
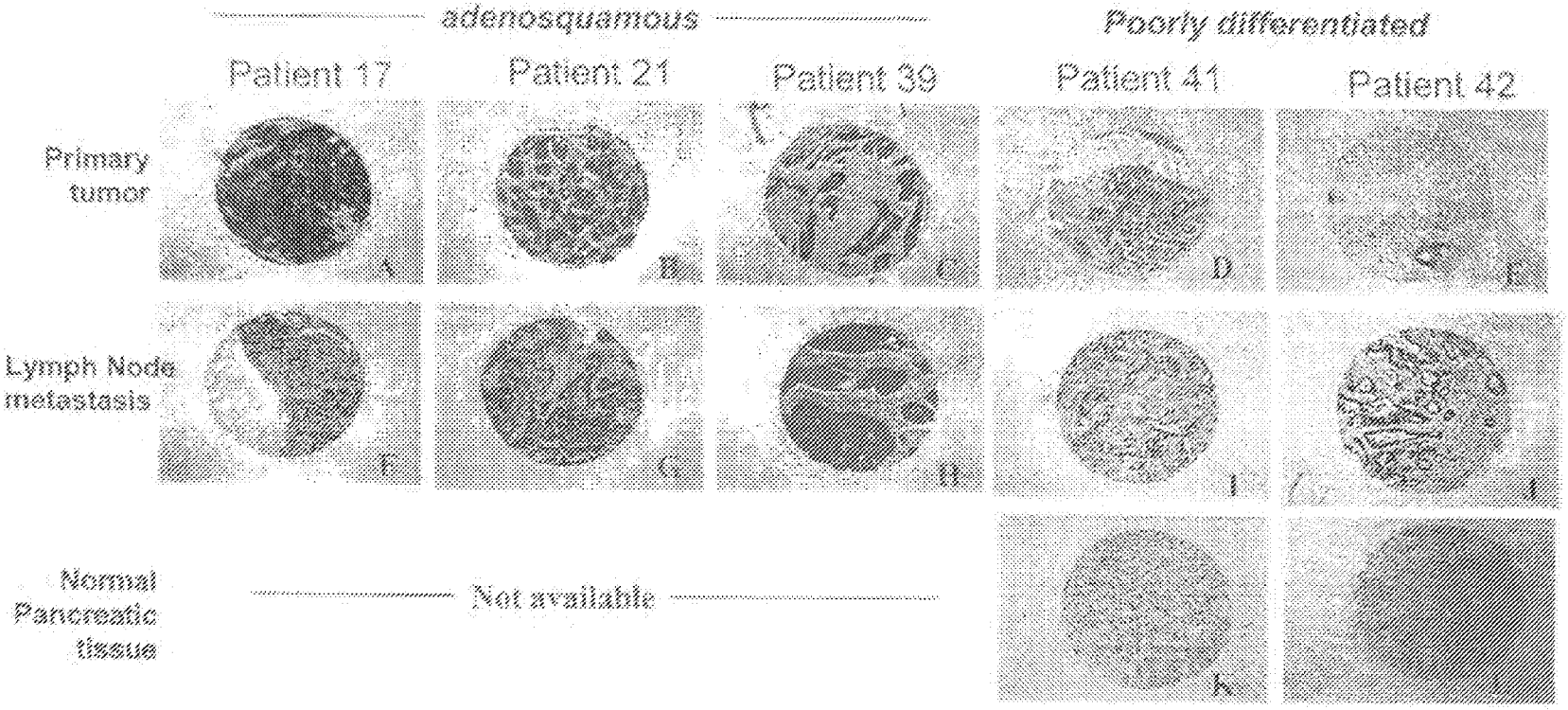
FIG. 6 demonstrates the ability of an anti-αvβ6 monoclonal antibody (3G9) to inhibit tumor growth in the BxPC-3 mouse xenograft model of human pancreatic cancer.
Figure 7:
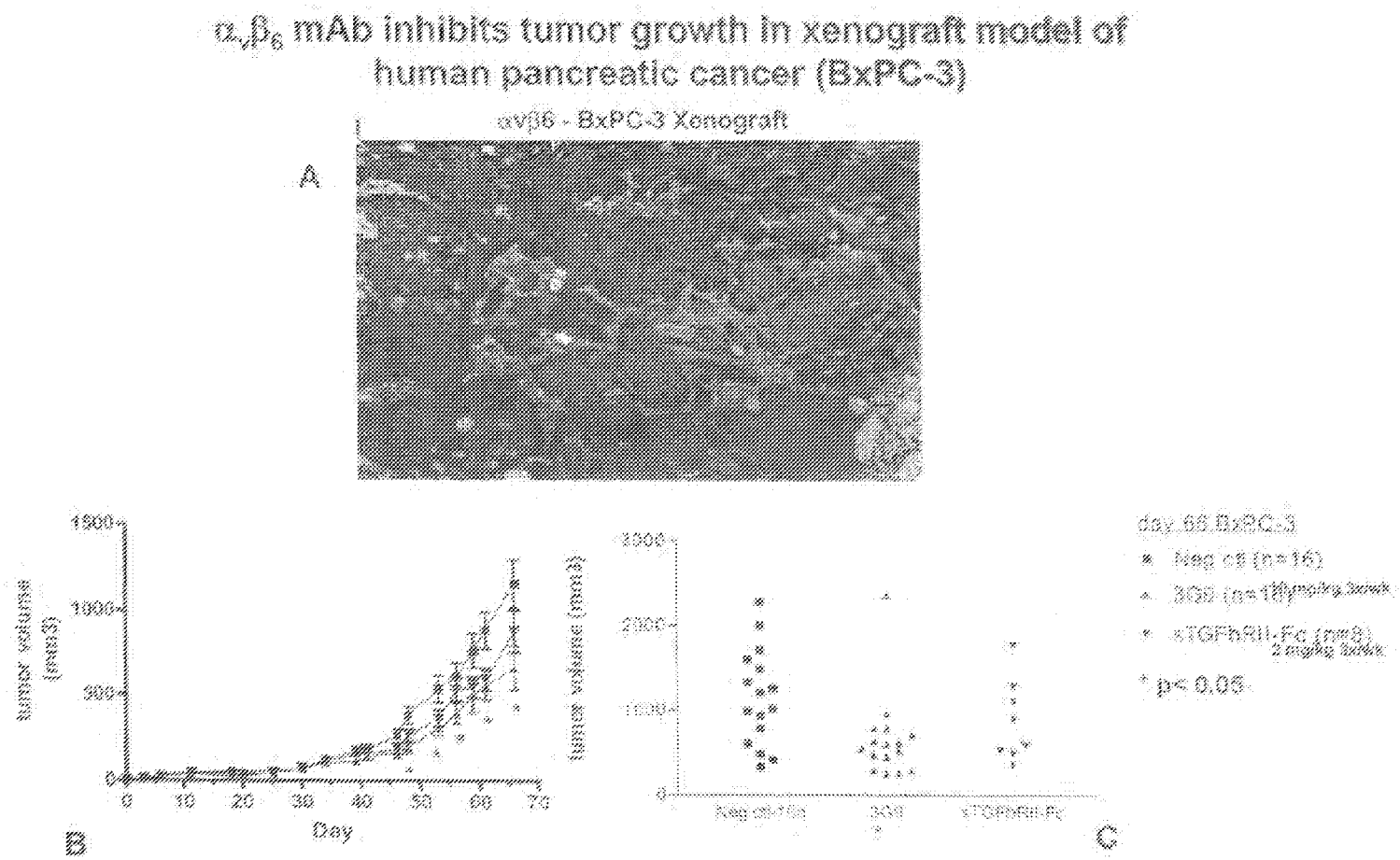
FIG. 7 is a series of photomicrographs of pancreatic tissue/tumor sections from three different patient samples, probed for expression of integrin αvβ6 (top three panels) or of smad4 (bottom three panels).

Treatment with anti-$\alpha_v\beta_6$ mAb 3G9 had a direct effect on tumor growth (FIGS. 6B, 6C), with significantly reduced tumor growth observed after about 48 days of treatment with the antibody. The level of growth inhibition observed with solTGFβRII-Fc was somewhat lower than that observed for 3G9. These results indicate that the anti-$\alpha_v\beta_6$ mAb 3G9 inhibits tumor growth in a xenograft model of human pancreatic cancer, and suggest that such blocking antibodies could be useful in inhibiting tumor growth, and by extension tumor invasion, in primary human pancreatic adenocarcinomas.

Example 2

Inverse Relationship Between smad4 Gene Expression and Integrin Expression in Primary Human Pancreatic Tumors To examine the relationship between smad4 expression and αvβ6 expression in primary tumor cells, sections of human primary pancreatic tumors were obtained and stained via immunohistochemistry for SMAD4 protein and for αvβ6. Fourteen tumor samples from different patients were examined. Results are shown in FIGS. 7-13.

Figure 8:
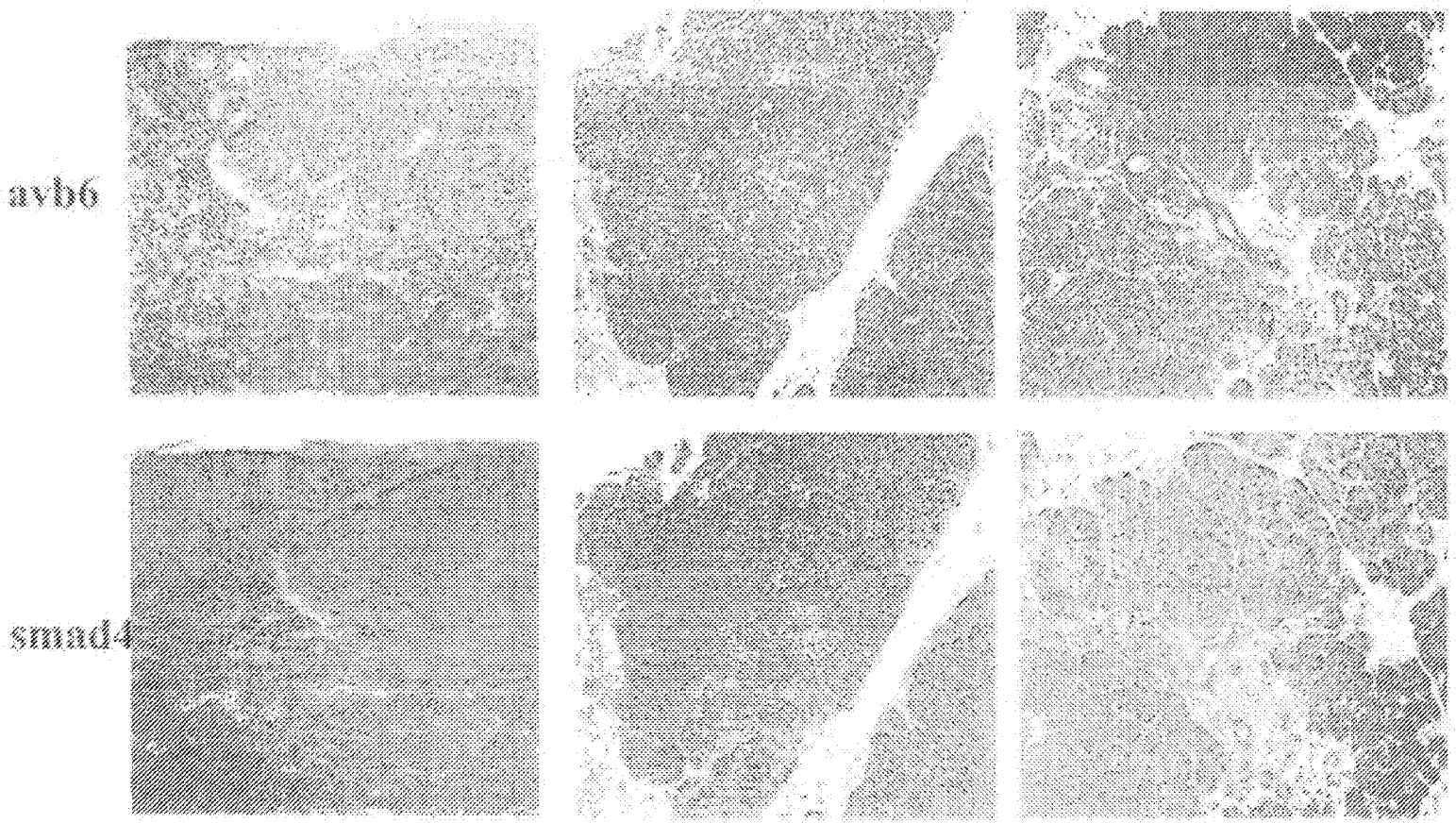
FIG. 8 is a series of photomicrographs of pancreatic tissue/tumor sections from three different patient samples (and different from those in FIG. 7), probed for expression of integrin αvβ6 (top three panels) or of smad4 (bottom three panels).
Figure 9:
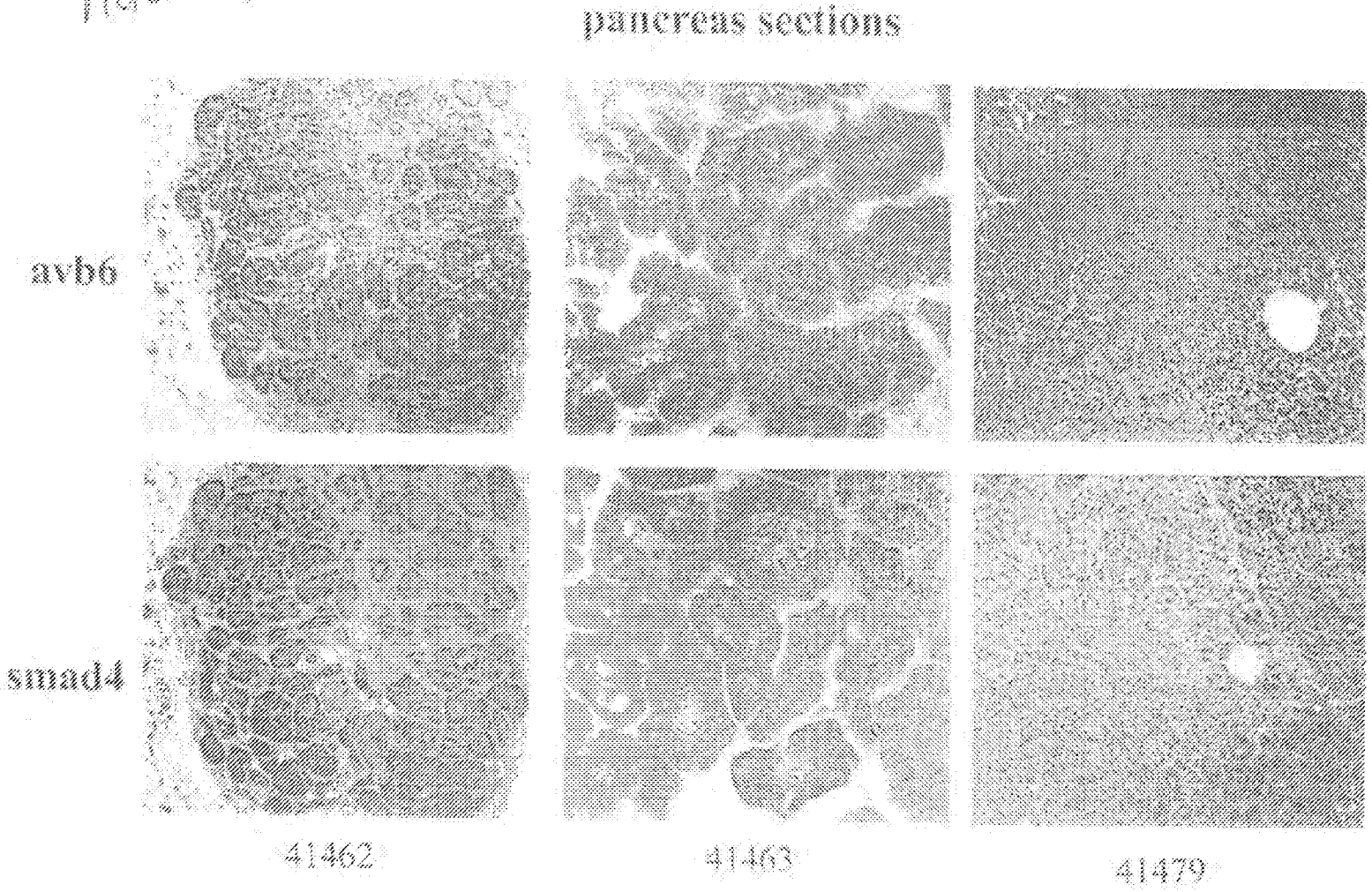
FIG. 9 is a series of photomicrographs of pancreatic tissue/tumor sections from three different patient samples (and different from those in FIGS. 7 and 8), probed for expression of integrin αvβ6 (top three panels) or of smad4 (bottom three panels).
Figure 10:
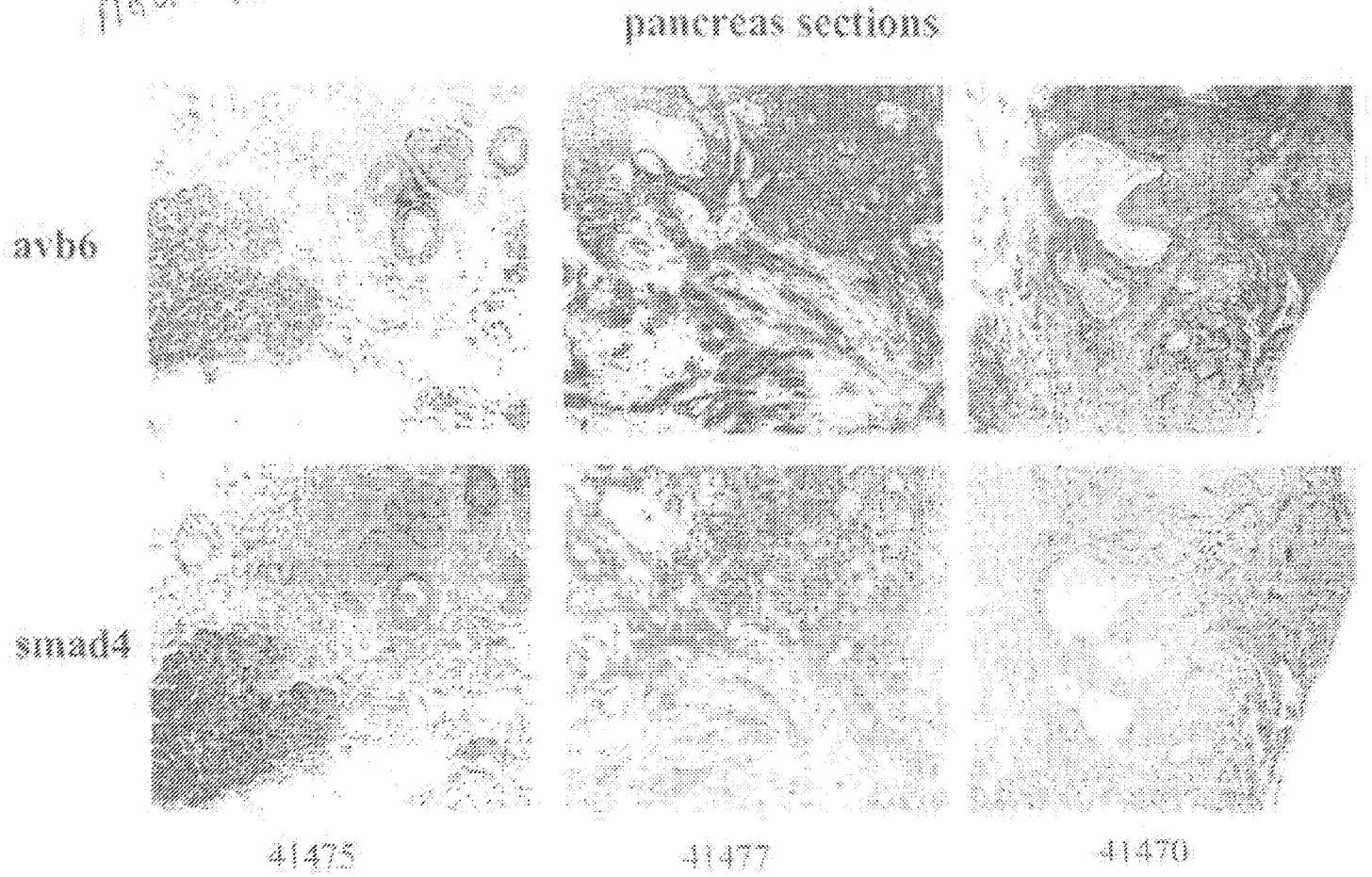
FIG. 10 is a series of photomicrographs of pancreatic tissue/tumor sections from two different patient samples (and different from those in FIGS. 7-9), probed for expression of integrin αvβ6 (top two panels) or of smad4 (bottom two panels).
Figure 11:
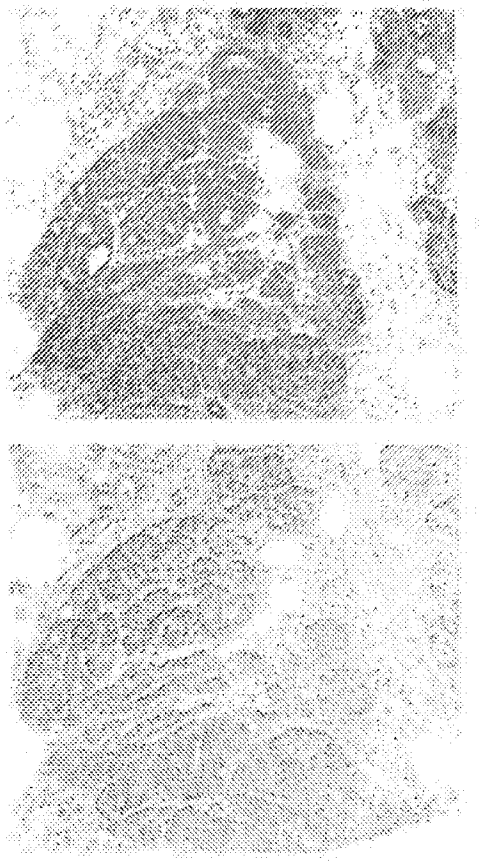
FIG. 11 is a series of photomicrographs of pancreatic tissue/tumor sections from two different patient samples (and different from those in FIGS. 7-10), which are heterogeneous ("+/−") with respect to expression of integrin αvβ6, probed for expression of integrin αvβ6 (top two panels) or of smad4 (bottom two panels).
Figure 12:
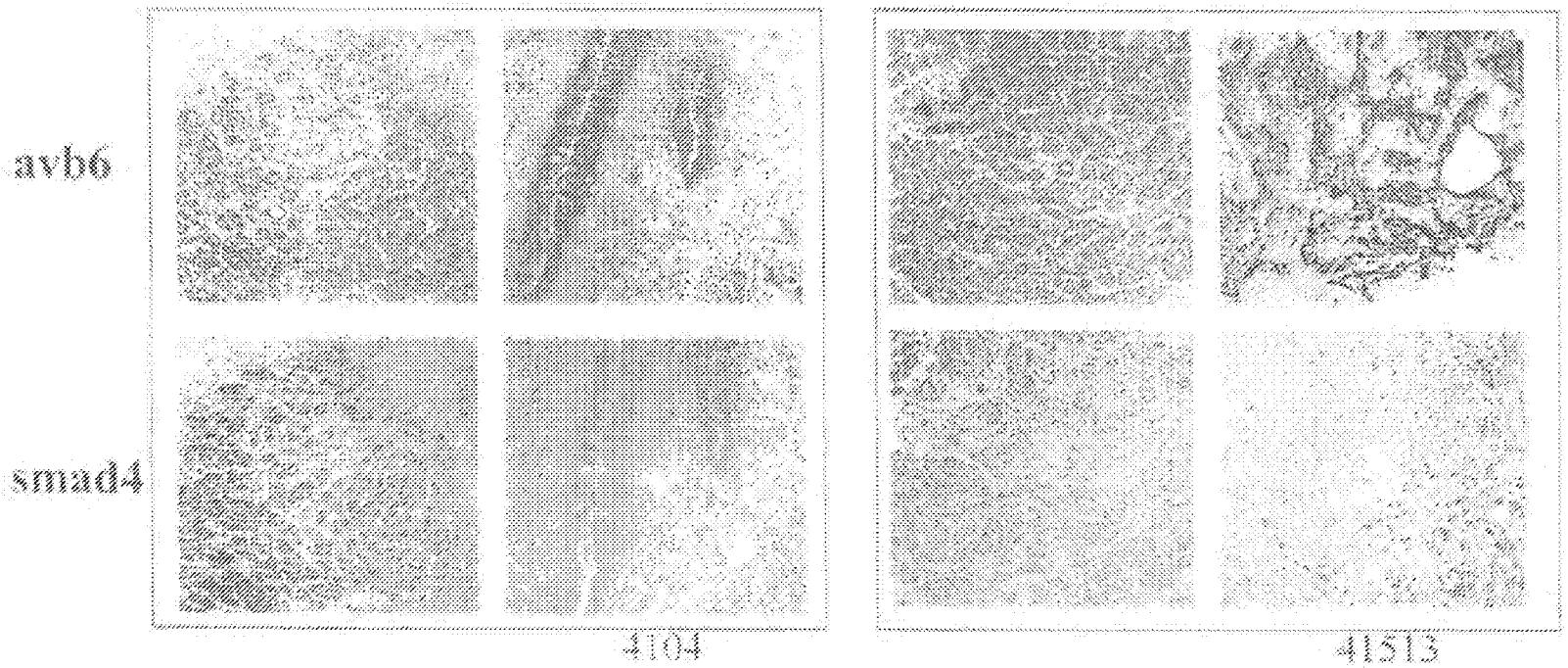
FIG. 12 is a series of photomicrographs of pancreatic tissue/tumor sections from a single patient sample (different from those in FIG. 11), which are heterogeneous ("+/−") with respect to expression of integrin αvβ6, probed for expression of integrin αvβ6 or of smad4.
Figure 13:
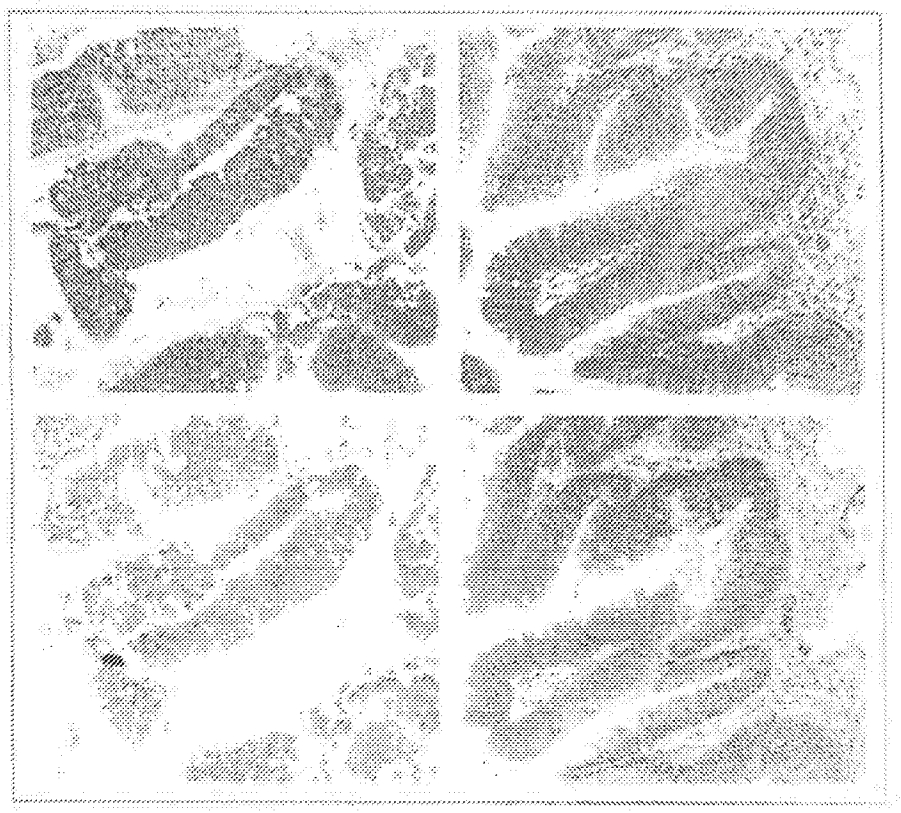
FIG. 13 is a Table summarizing the results depicted in FIGS. 7-12.

Of the 14 tumor samples, 7 (50%) were found to have clearly αvβ6+ tumor areas, while 3 of these showed heterogeneity in expression (i.e., some sections of the tumor that were αvβ6+, other sections in the same tumor that were αvβ6−; FIGS. 8-9). Seven of the 14 tumors were found to be αvβ6−negative.

In the 11 tumors (excluding the 3 that were heterogeneous in αvβ6 expression), the following results were observed FIGS. 7-10, 13:

(A) four were αvβ6+, and of these, three were smad4− and one was smad4+; and (B) seven were αvβ6−, and all seven of these were smad4+.

Of the three tumors in which αvβ6 expression was heterogeneous, the following results were observed (FIGS. 11-13):

(A) those areas of the tumors that were αvβ6+ were smad4−; and (B) those areas of the tumors that were αvβ6− were smad4+.

These results support the conclusion that there is an inverse relationship between the expression of smad4 and of integrin αvβ6 by primary pancreatic tumor cells.

Example 3

Expression of αvβ6 and smad4 on Pancreatic Cancer Cell Lines

Expression of $\alpha_v\beta_6$ and smad4 were determined for a panel of pancreatic cell lines. The results are summarized in FIG. 14.

In a preliminary analyses of $\alpha_v\beta_6$ and smad4 expression on primary pancreatic ductal adenocarcinomas (PDACs), three sample sets were examined. In the first set, 10 PDAC samples were tested by BioCat array, and all 10 (100%) were found to express $\alpha_v\beta_6$. In the second set, 14 pancreatic adenocarcinoma samples were tested by Cytomix assay, and 7 (50%) of these were $\alpha_v\beta_6$ positive. In the third set, 11 PDAC samples were tested by a Folio array (FIG. 15), and of these 10 (91%) were αvβ6 positive.

Figure 16:
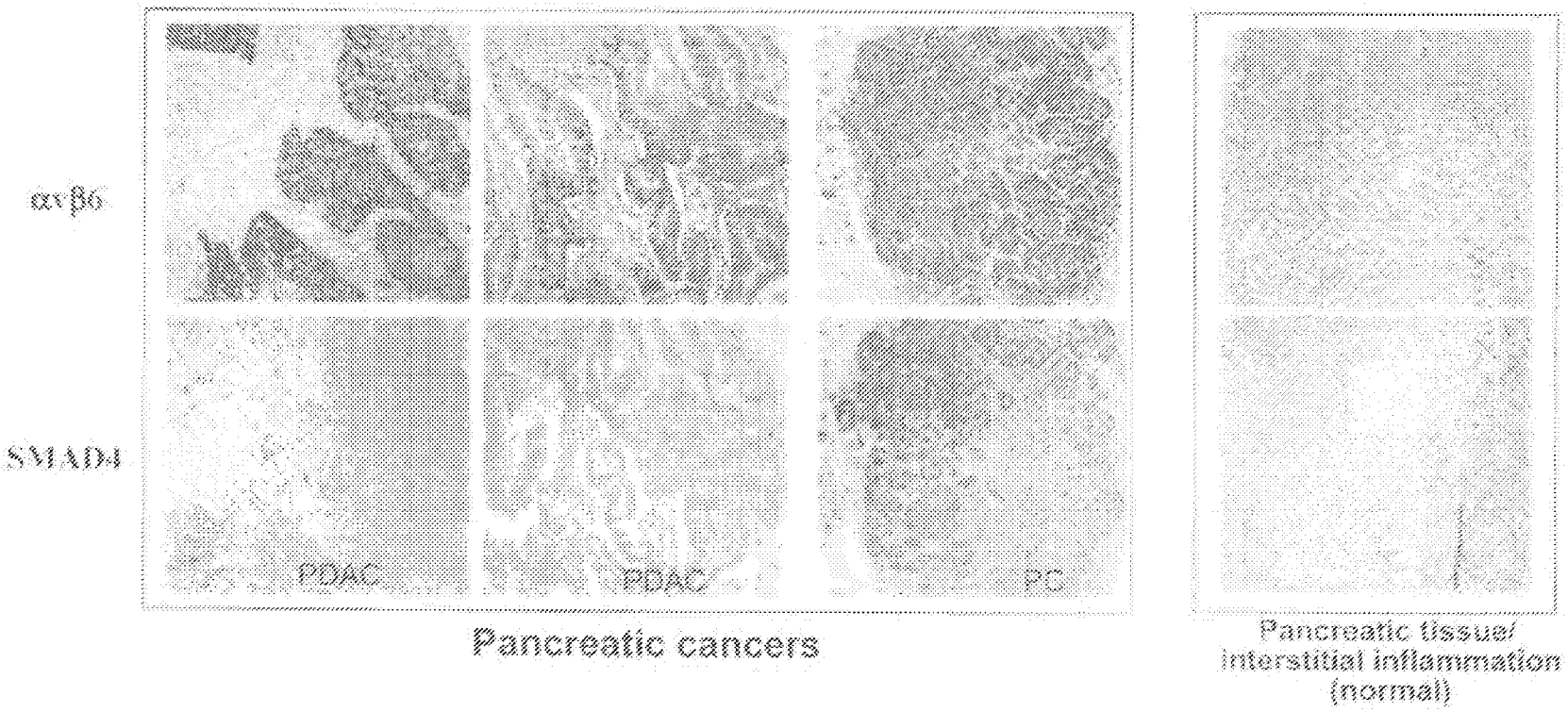
FIG. 16 is a schematic diagram summarizing αvβ6 and smad4 expression levels in 23 different pancreatic tumor tissue samples.

For the second and third sample sets, smad4 expression was also assayed. Fifteen lines were found to be αvβ6 positive, and 11 of the lines were smad4 positive. Twelve lines were αvβ6+/smad4−; 8 lines were αvβ6−/smad4+; and 3 lines were αvβ6+/smad4+. Two of the lines were heterogeneous and had areas that stained as αvβ6+/smad4− and αvβ6−/smad4+ (FIG. 16).

Figure 17:
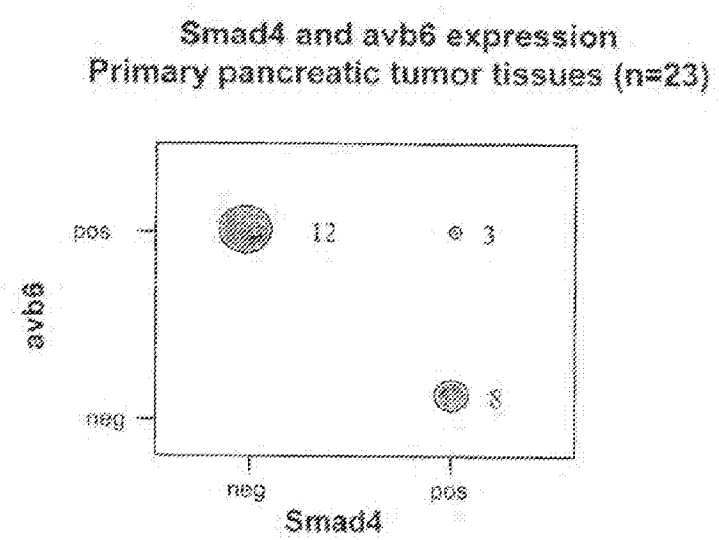
FIG. 17 is a schematic diagram summarizing αvβ6 and smad4 expression levels in 70 different pancreatic ductal adenocarcinoma (PDAC) samples assayed on Biomax tissue microarrays.

Seventy PDACs were examined by immunohistochemistry on Biomax Tissue MicroArray (FIG. 17). 89% of these samples were determined to be αvβ6 positive, 97% of which were smad4 downregulated. In total, 86% had a αvβ6+/smad4− phenotype.

Figure 18:
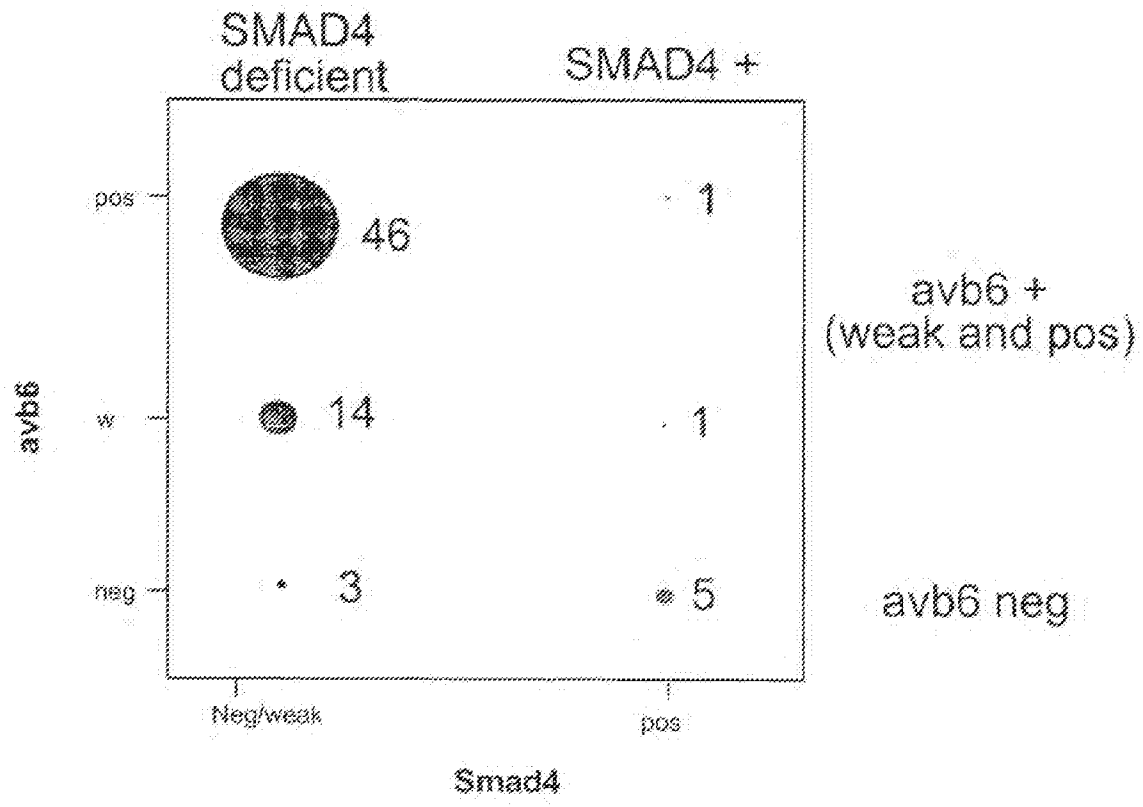
FIG. 18 is a schematic diagram summarizing αvβ6 and smad4 expression levels in 50 different PDAC samples assayed on Leiden arrays.

In a separate study of 50 PDACs examined by immunohistochemistry on tissue arrays prepared at the Leiden University Medical Center (LUMC) (hereafter, "Leiden arrays"), 88% were determined to be αvβ6 positive, 59% of which were smad4 downregulated (FIG. 18). In total, 52% had a αvβ6+/smad4− phenotype.

Figure 19:
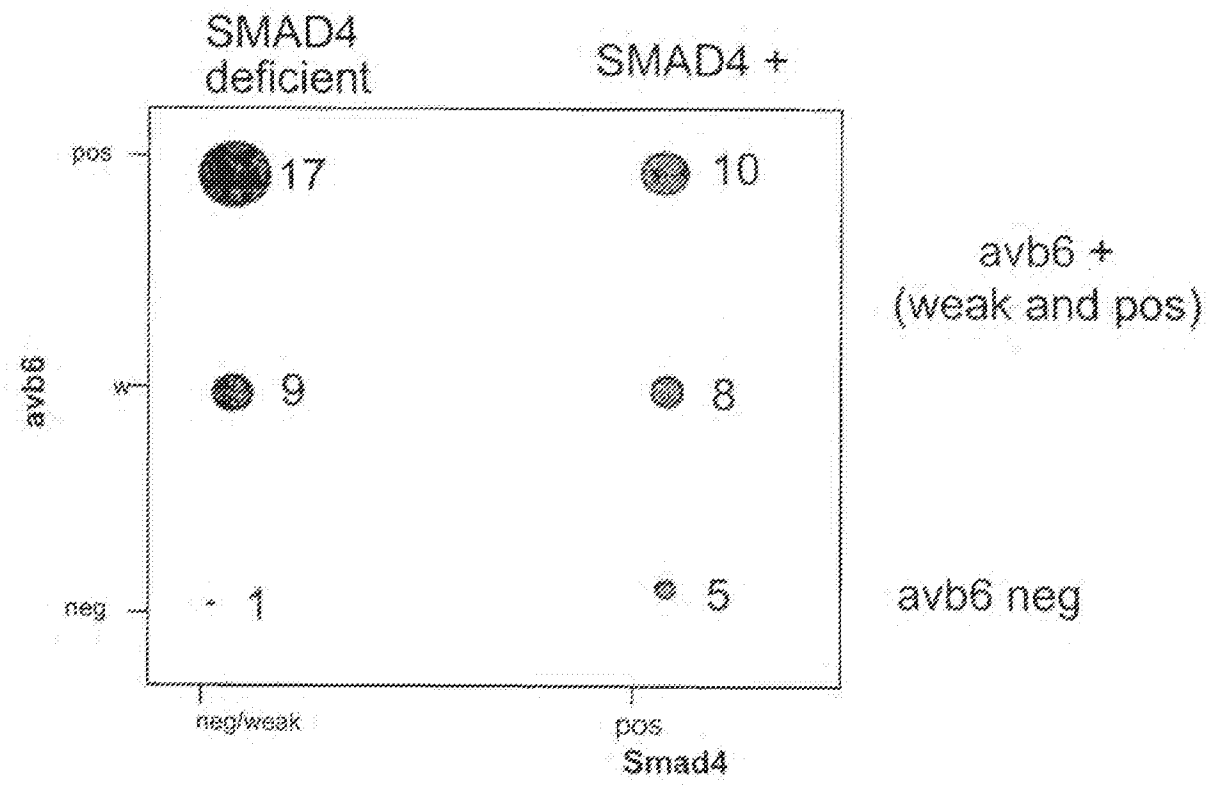
FIG. 19 is a schematic diagram summarizing αvβ6 and smad4 expression levels in 9 different PDAC metastases samples assayed on Leiden arrays.

In a study of 9 PDAC metastases examined using the Leiden arrays, all were found to be αvβ6 positive (most were strongly positive), and 78% had a αvβ6+/smad4− phenotype (FIG. 19).

The above results indicate that an αvβ6+/smad4− phenotype is the predominant phenotype in primary human pancreatic cancers.

Figure 20:
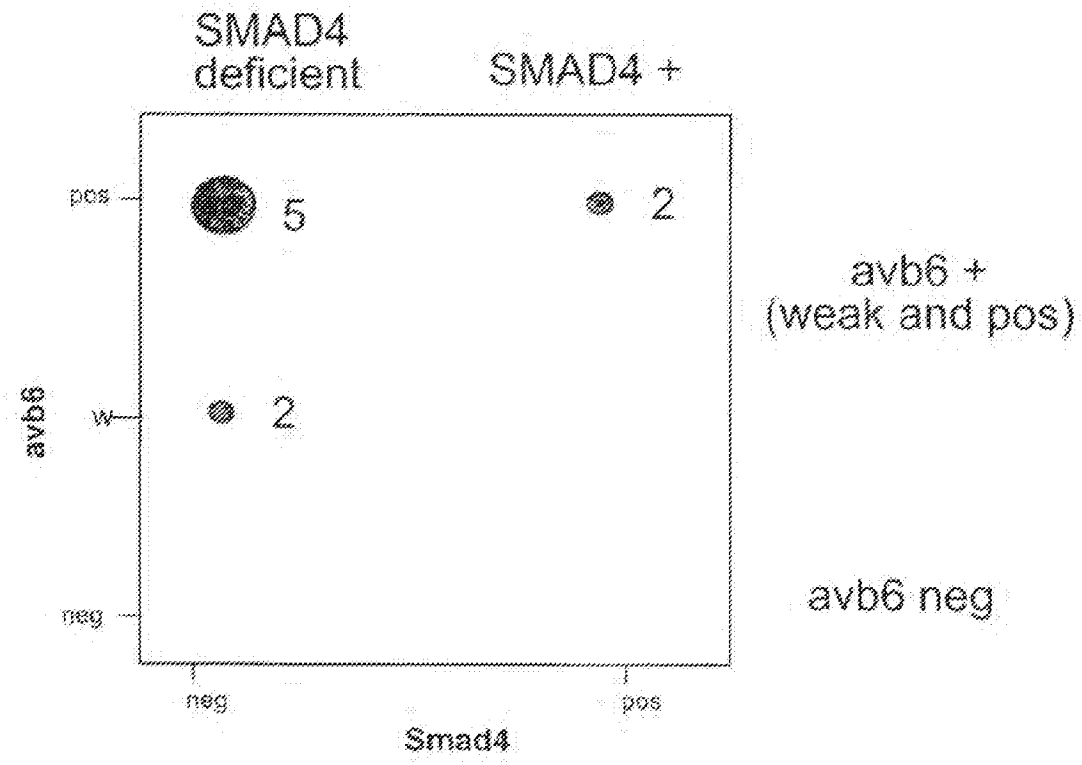
FIGS. 20A and B are bar graphs summarizing the results of αvβ6 and smad4 expression levels in PDACs as measured by Biomax array and Leiden array, respectively.
Figure 21:
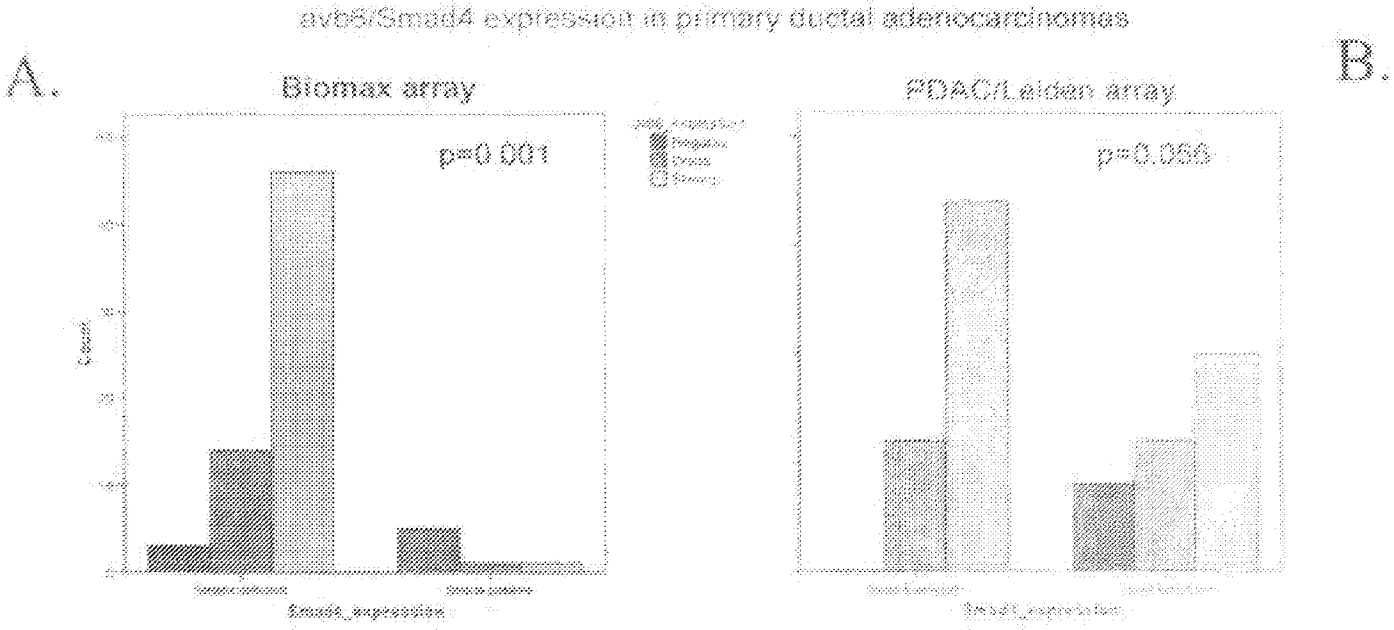
FIG. 21 is a line graph demonstrating the response of BxPC 3 human pancreatic adenocarcinoma cells, subcutaneously implanted into athymic nude mice, to mAb 3G9 and gemcitabine, either as single agents or in combination.
Figure 22:
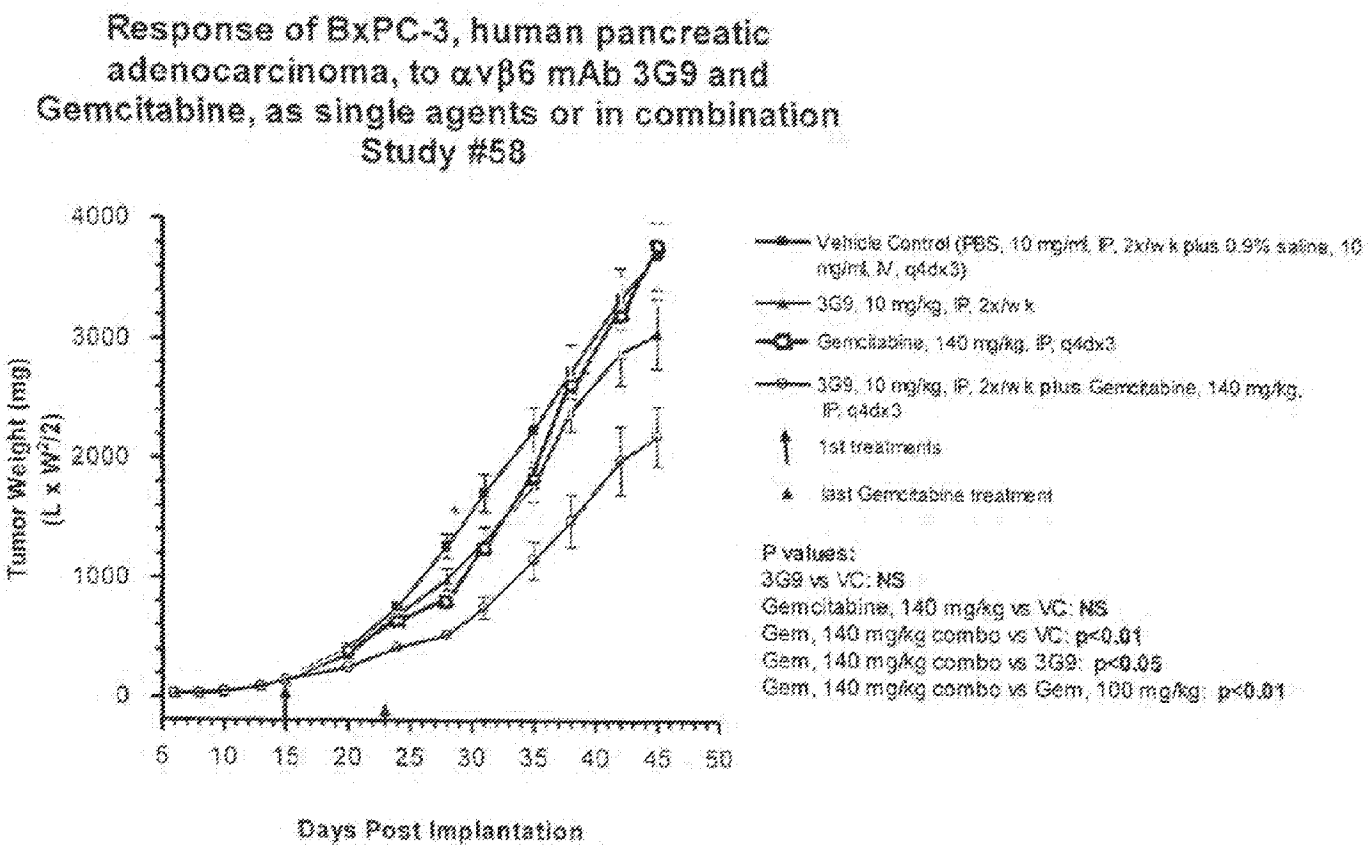
FIG. 22 is a line graph demonstrating the response of BxPC 3 human pancreatic adenocarcinoma cells, subcutaneously implanted into athymic nude mice, to mAb 3G9 and gemcitabine, either as single agents or in combination, expressing the results of test animals as a percentage of control (vehicle) results.
Figure 23:
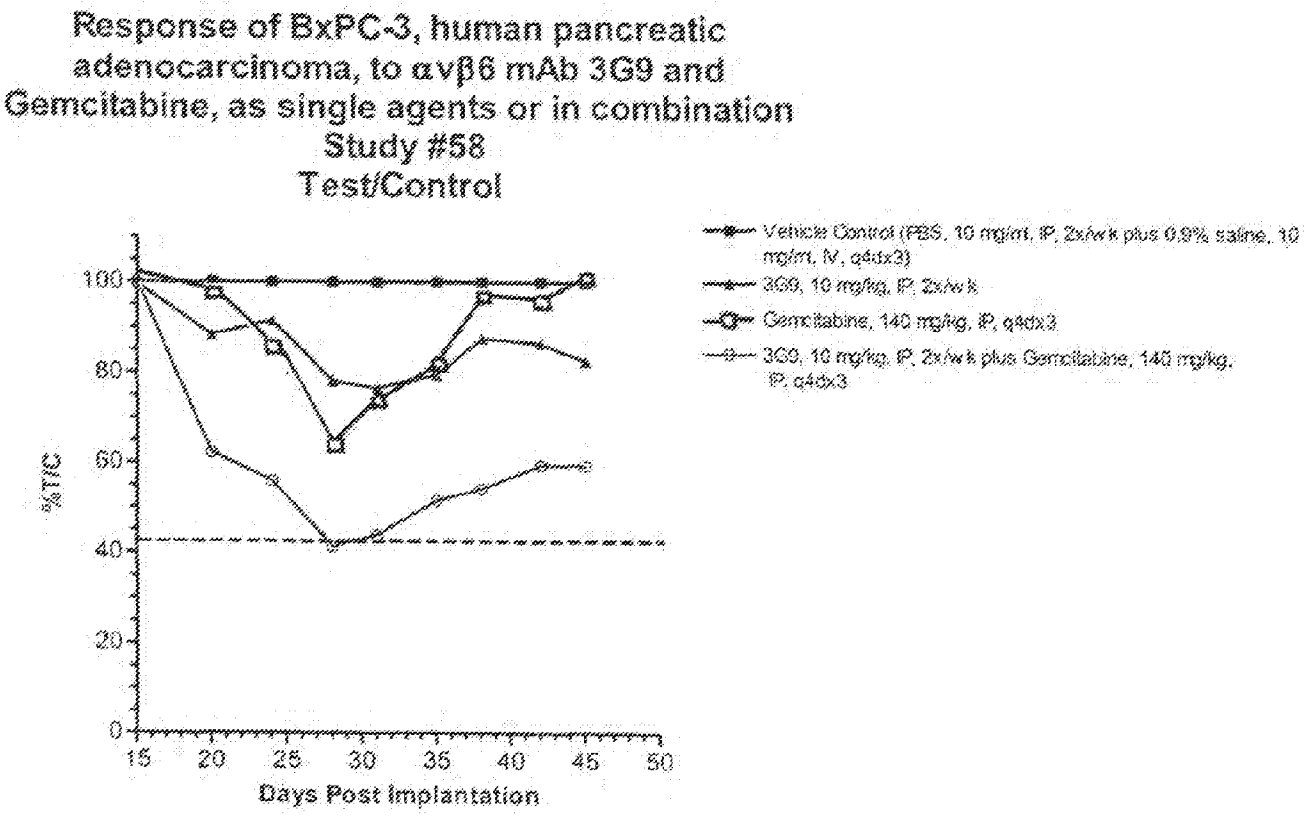
FIG. 23 is a scatter plot demonstrating the response of BxPC 3 human pancreatic adenocarcinoma cells, subcutaneously implanted into athymic nude mice, to mAb 3G9 and gemcitabine, either as single agents or in combination, at day 45 of the treatment regimen.
Figure 24:
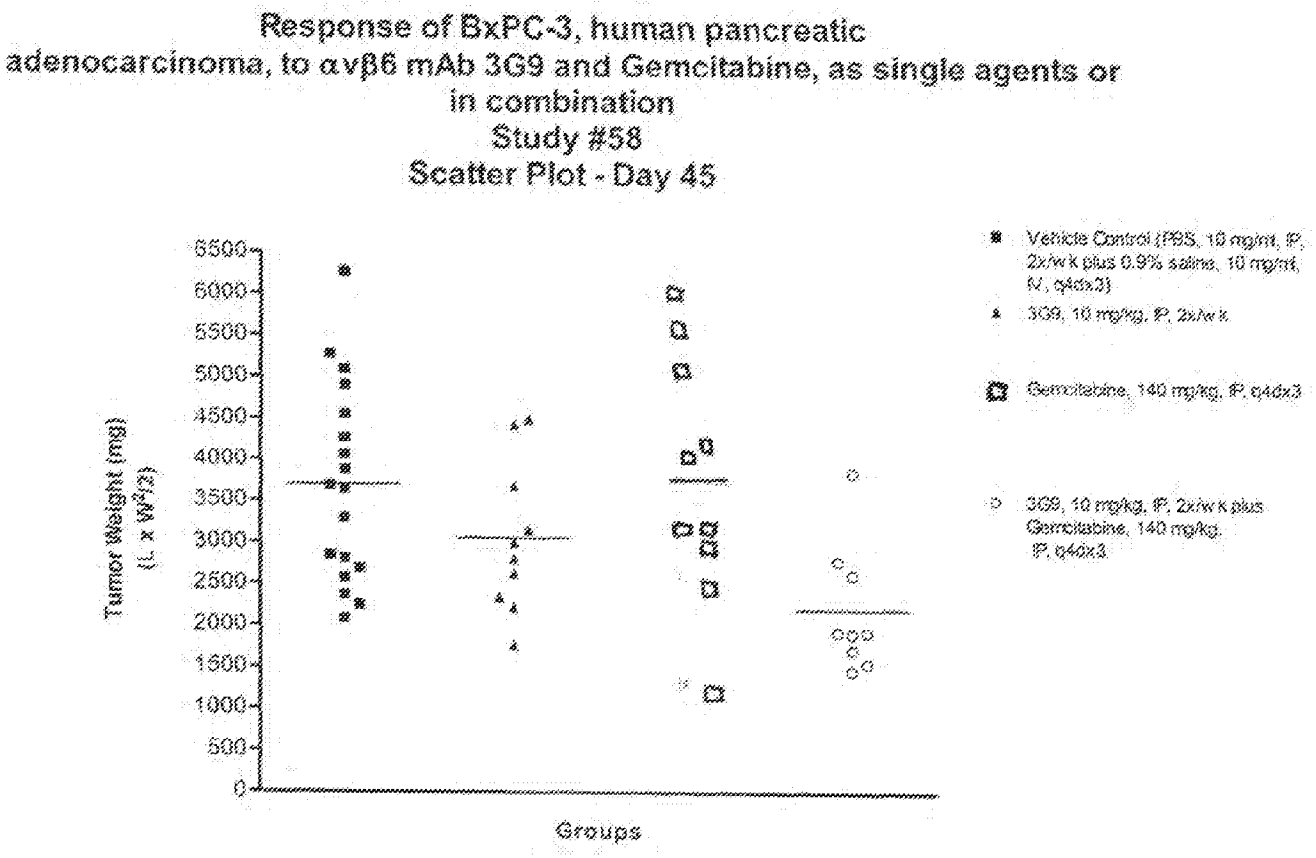
FIG. 24 is a line graph demonstrating change in host animal body weight in response to treatment with mAb 3G9 or gemcitabine.
Figure 25:
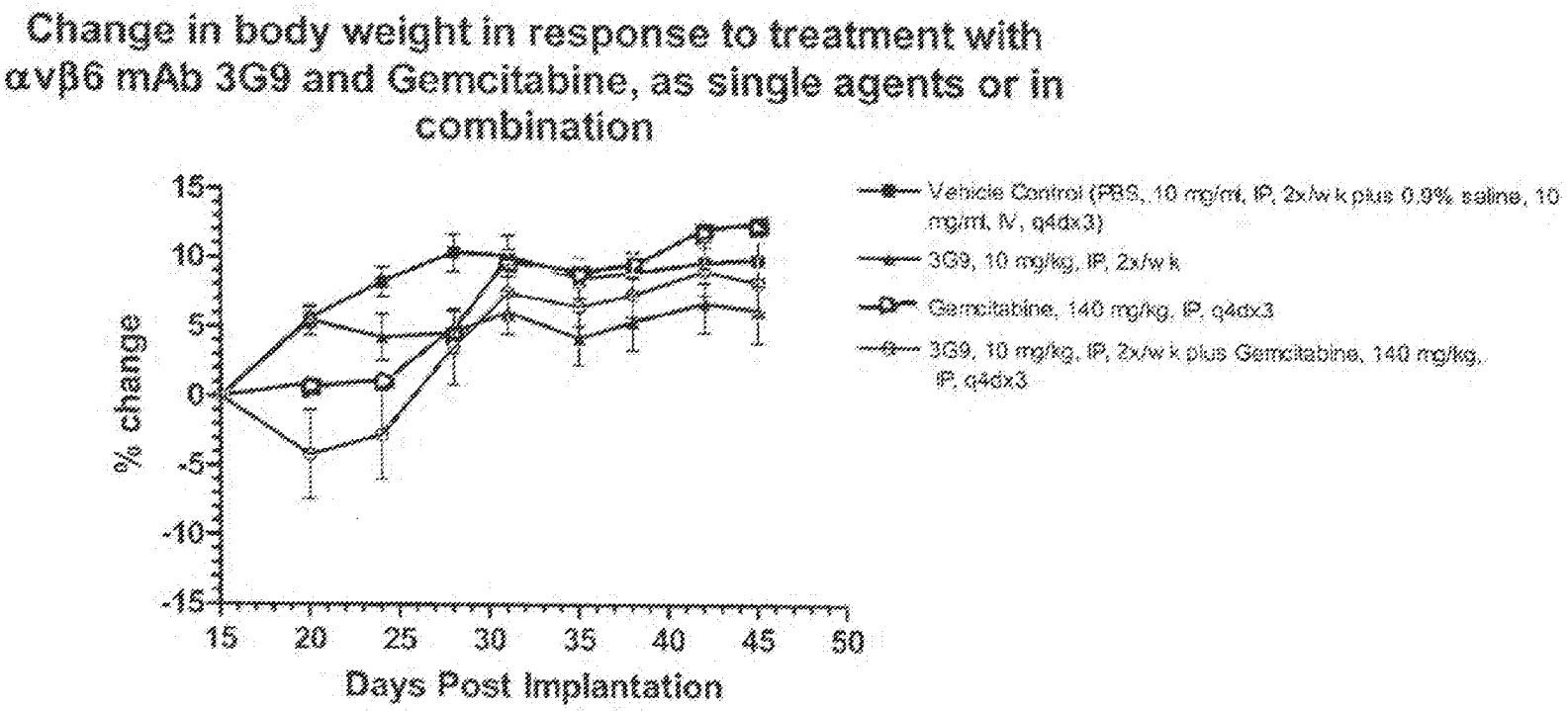
FIG. 25 is a line graph demonstrating the response of BxPC 3 human pancreatic adenocarcinoma cells, subcutaneously implanted into athymic nude mice, to mAb 3G9 and doxorubicin, either as single agents or in combination.
Figure 26:
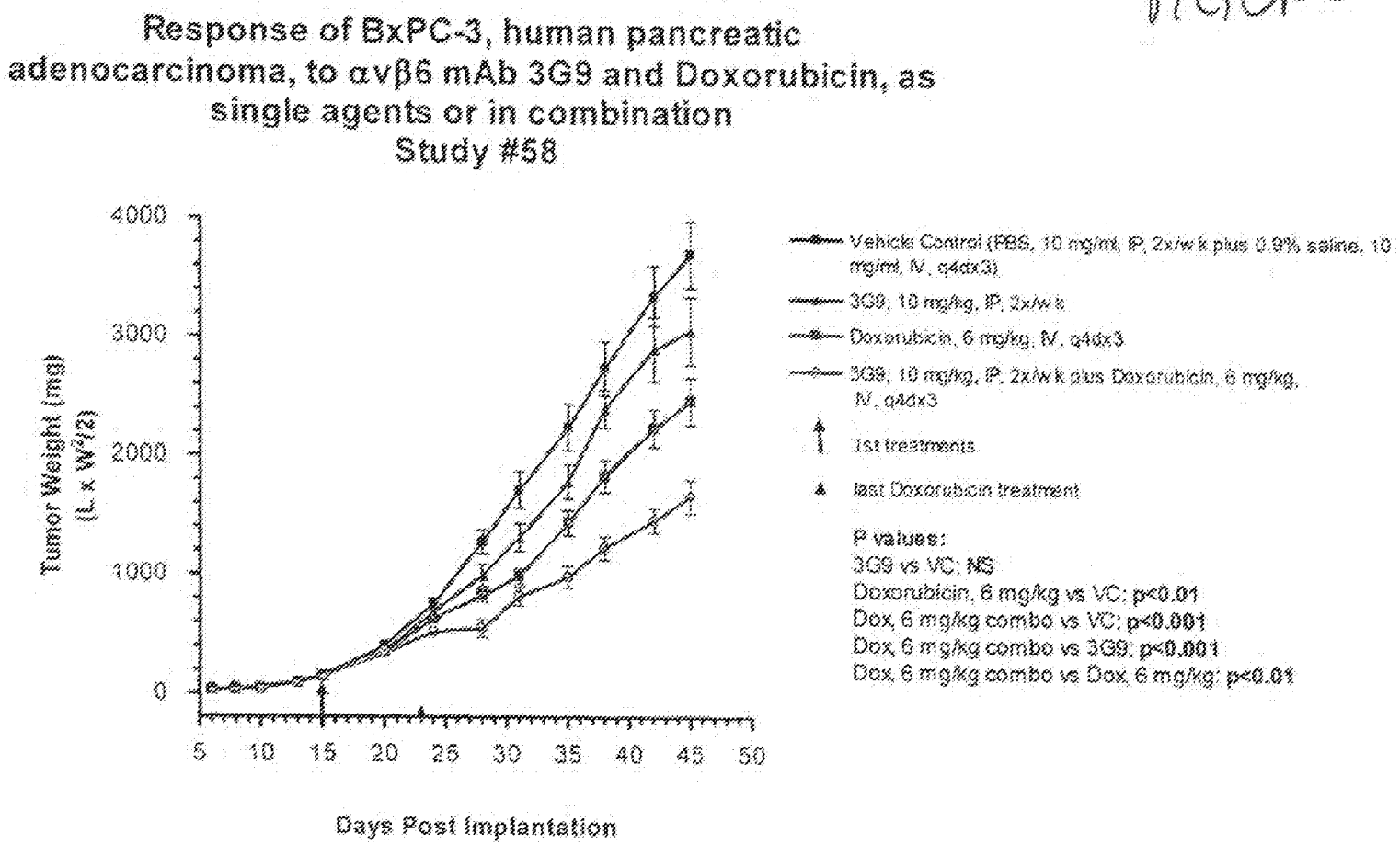
FIG. 26 is a line graph demonstrating the response of BxPC 3 human pancreatic adenocarcinoma cells, subcutaneously implanted into athymic nude mice, to mAb 3G9 and doxorubicin, either as single agents or in combination, expressing the results of test animals as a percentage of control (vehicle) results.
Figure 27:
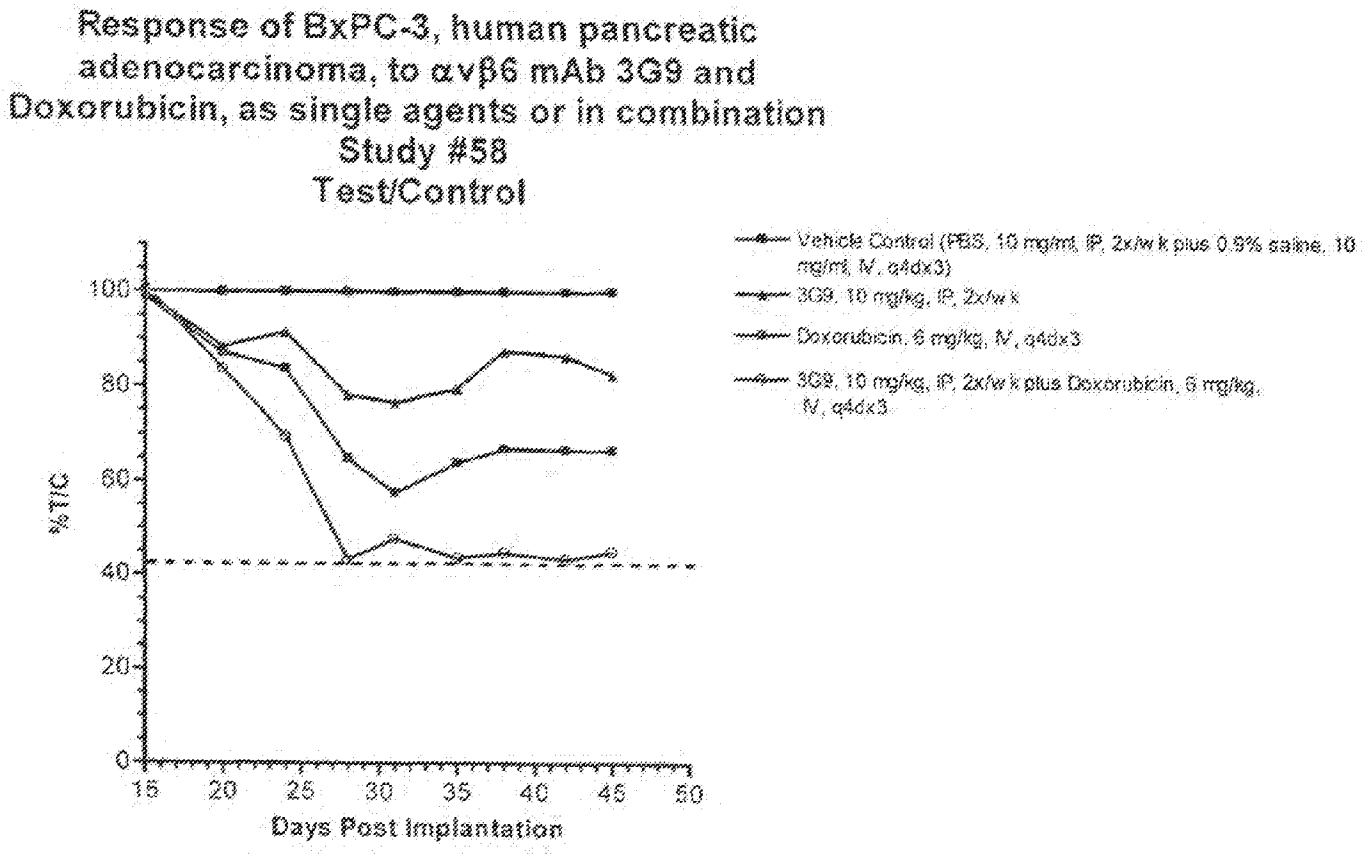
FIG. 27 is a scatter plot demonstrating the response of BxPC 3 human pancreatic adenocarcinoma cells, subcutaneously implanted into athymic nude mice, to mAb 3G9 and doxorubicin, either as single agents or in combination, at day 45 of the treatment regimen.
Figure 28:
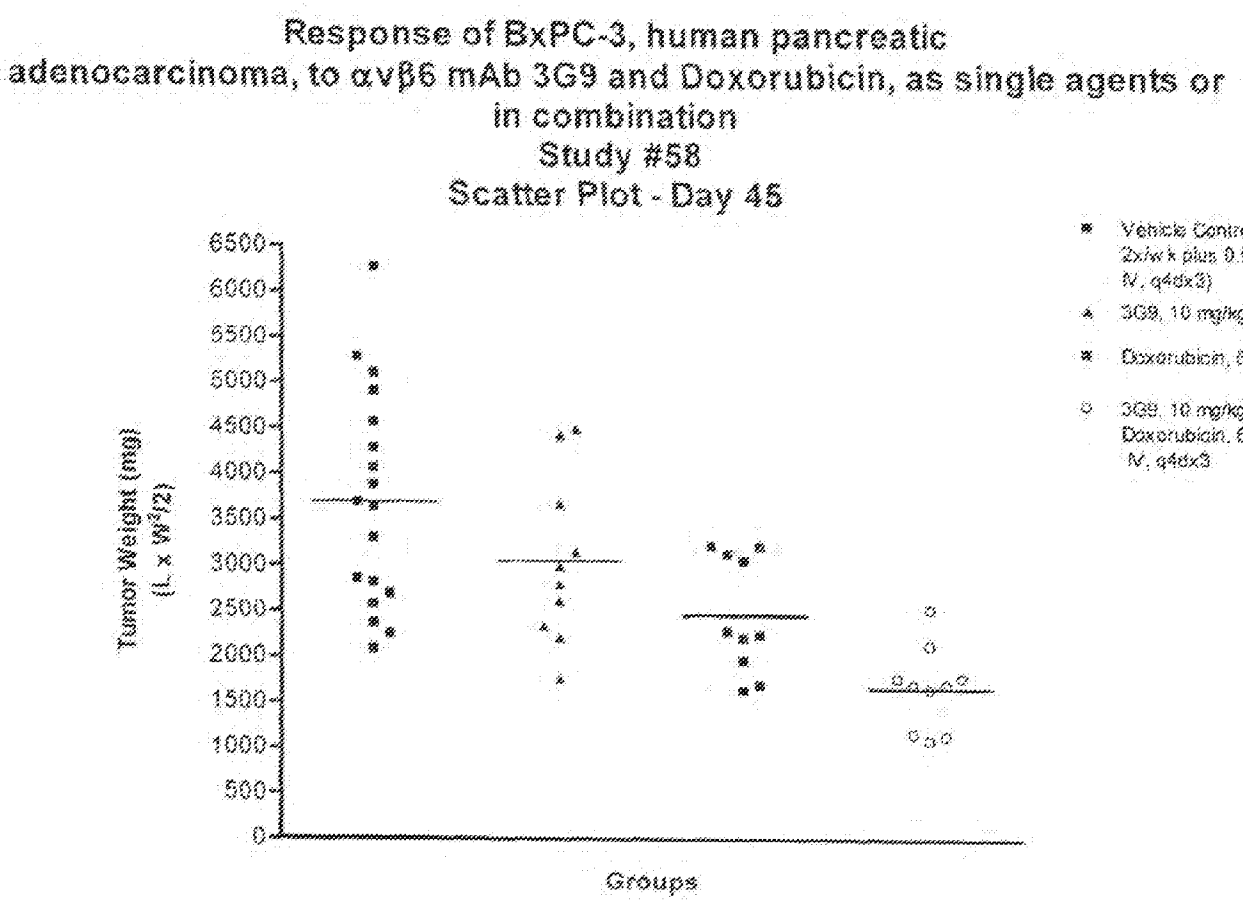
FIG. 28 is a line graph demonstrating change in host animal body weight in response to treatment with mAb 3G9 or doxorubicin.

A graphical representation of the results of αvβ6 and smad4 expression analysis on PDAC as scored in the Leiden and Biomax arrays is shown in FIG. 20. The differences in results observed between the two different methods may be due to the lower intensities of smad4 expression observed using the Biomax arrays.

Example 4

Response of the Subcutaneously Implanted BxPC-3, Human Pancreatic Adenocarcinoma, to $\alpha_v\beta$ mAb 3G9 and the Chemotherapeutics, Adriamycin (Doxorubicin) and Gemcitabine, both as Single Agents and in Combination As a model for human tumor treatment, single or combination chemotherapy was carried out in the BxPC-3 xenogeneic mouse model of human pancreatic tumors. BxPC-3 is known to be smad4-deficient due to an apparent homozygous deletion of the smad4 gene in these cells (Subramanian, G. et al., Cancer Res. 64:5200-5211 (2004); Yasutome, M. et al., Clin. Exp. Metastasis 22:461-473 (2005).

Materials and Methods:

1. Animals. 220 athymic nude female mice from Harlan Sprague Dawley (Madison, Wis.), Rec. Mar. 13, 2006, DOB Jan. 30, 2006. Mice started on study at 6-7 weeks of age. Animals are acclimated to the lab for at least 5 days prior to implantation of tumor. Animals are individually marked with BioMedic implantable ID chips. Data collection performed using Onco Pharmacology Informatics (OPI).

2. Tumor. BXPC-3, cell line originally obtained from the University of Arizona (Tucson, Ariz.). The cell line is a human pancreatic adenocarcinoma. Donor line was passed for 5 generations in athymic nude female mice prior to implantation into this study. Animals implanted with a 3 $mm^3$ fragment of tissue via trochar subcutaneously into the right flank area. Treatments were initiated on an established tumor with a minimum size of 100 milligrams and three progressive growths.

| Group # | Treatment ** | # of Mice |
|---|---|---|
| 1. | Vehicle Control, Pyrogen-free PBS, 10 ml/kg/ini, i.p., 2x/wk plus 0.9% Sterile Saline, 10 ml/kg/ini, i.v., Q4Dx3 | 18 |
| 2. | 3G9, 10 mg/kg/inj., i.p., 2x/wk | 10 |
| 3. | Gemcitabine, 100 mg/kg/inj, i.p., Q4Dx3 | 10 |
| 4. | Gemcitabine, 140 mg/kg/inj, i.p., Q4Dx3 | 10 |
| 5. | Adriamycin (doxorubicin), 3 mg/kg/inj, i.v., Q4Dx3 | 10 |
| 6. | Adriamycin (doxorubicin), 6 mg/kg/inj, i.v., Q4Dx3 | 10 |
| 7. | 3G9, 10 mg/kg/inj., i.p., 2x/wk plus Gemcitabine, 100 mg/kg/inj, i.p., Q4Dx3 | 10 |
| 8. | 3G9, 10 mg/kg/inj., i.p., 2x/wk plus Gemcitabine, 140 mg/kg/inj, i.p., Q4Dx3 | 10 |
| 9. | 3G9, 10 mg/kg/inj., i.p., 2x/wk plus Adriamycin (Dox), 3 mg/kg/inj, i.v., Q4Dx3 | 10 |
| 10. | 3G9, 10 mg/kg/inj., i.p., 2x/wk plus Adriamycin (Dox), 6 mg/kg/inj, i.v., Q4Dx3 | 10 |

3. Testing Schedule.

Day—1: Implant ID transponders subcutaneously in the left flank.

Day 0: Implant tumor as described above. Run bacterial cultures on the tumor implanted into mice. Record initial body weight of animals.

Day2: Begin recording tumor size and body weight measurements and continue every other day until staging day.

Staging Day (Treatment Day 1) (approximately Day 11-13 post implantation): Select mice with tumors measuring a minimum size of 100 milligrams determined using vernier calipers. Randomize mice into control and treatment groups and record body weights. Administer i.p. doses on the schedule listed above. Doses are blinded within each dosing regimen. Continue to record tumor size and body weights on mice 2×/week. Monitor the study daily and make notations of any unusual observation on animals. Study will be blinded until the termination of the study.

Midpoint Bleed: (Day 34/35 post implantation): Before first dose of 3G9 for the week collect serum from 5 animals/group from all groups. 24 hours post dosing, collect serum from the remaining 5 animals/group from all groups. Use the 5 remaining animals/group not used for the trough serum collection 24 hours earlier.

Final week of dosing (Day 44/45 post implantation): Before final dose of 3G9 collect serum from 5 animals/group from all groups. 24 hours post dosing, collect serum from the remaining 5 animals/group from all groups. Use the 5 remaining animals/group not used for the trough serum collection 24 hours earlier.

Endpoints:

(a) Initial body weight (b) Tumor size and body weight measurements twice weekly (c) Serum 3G9 levels at midpoint and final week of dosing At sacrifice:

7 tumors from each of the following groups are harvested; ½ of each tumor preserved in 10% NBF, the other ½ frozen in OCT:

Group 1: Vehicle; Group 2: 3G9; Group 4: Gemcitabine (Gem) @140 mg/kg; Group 6: Doxorubicin (Dox) @ 6 mg/kg; Group 8: 3G9 plus Dox @ 6 mg/kg; and Group 10: 3G9 plus Gem at 140 mg/kg.

Results

The results of these experiments are depicted in FIGS. 21-28. These results demonstrate that 3G9 in combination with gemcitabine leads to significantly increased growth inhibition, which seems to be synergistic. The combined effect is even greater when 3G9 is combined with doxorubicin (adriamycin), about 60% growth inhibition. This combination chemotherapy was chosen because data obtained earlier with this xenograft model by oncopharmacology (not shown) showed that BxPC-3 was resistant to gemcitabine. Together, these results demonstrate that the smad4-deficient cell line BxPC-3 is (a) responsive to treatment (measured as growth inhibition) with anti-αvβ6 mAbs as single agents; and (b) is chemosensitized by treatment with anti-αvβ6 mAbs to subsequent (or simultaneous) treatment with small molecule agents such as gemcitabine and doxorubicin.

Figure 29:
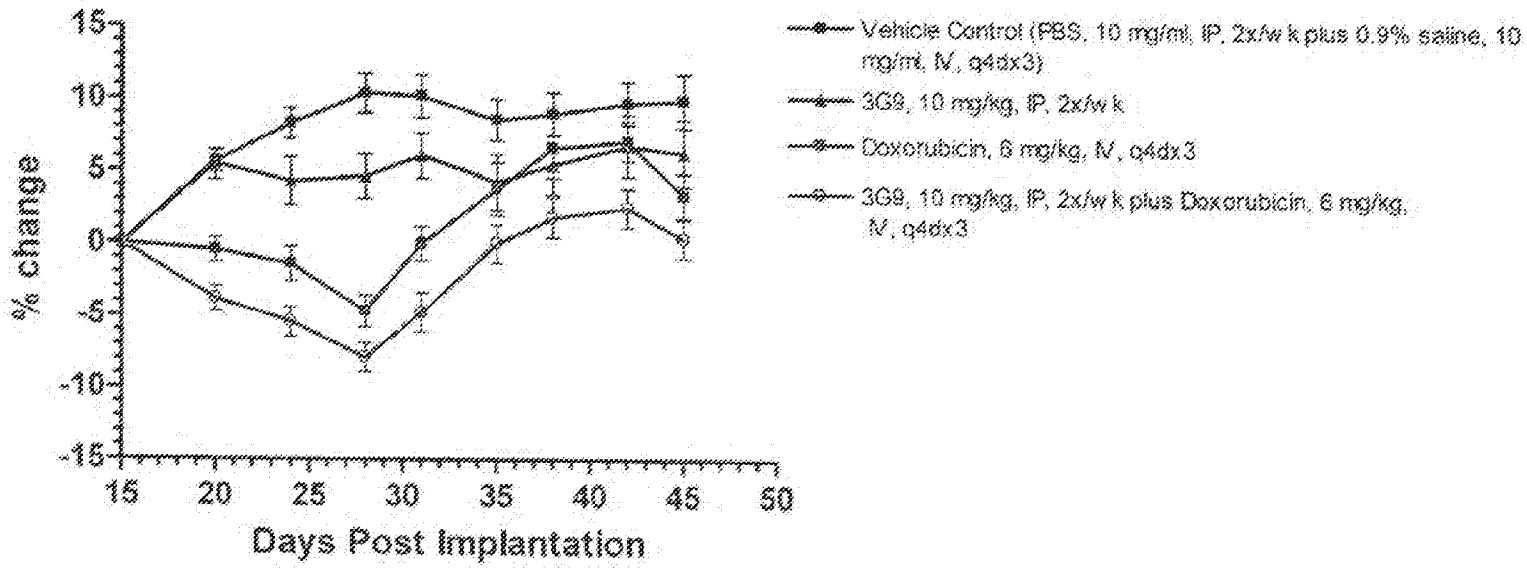
FIG. 29A is a line graph demonstrating the response of Su86.86 human pancreatic adenocarcinoma cells, subcutaneously implanted into athymic nude mice, to mAb 3G9 and gemcitabine, either as single agents or in combination, and to soluble TGF-β receptor II/Fc fusion protein (TGF-β RII-Fc).
FIG. 29B is a line graph demonstrating the response of Su86.86 human pancreatic adenocarcinoma cells, subcutaneously implanted into athymic nude mice, to mAb 3G9 and gemcitabine, either as single agents or in combination, and to TGF-β RII-Fc expressing the results of test animals as a percentage of control (vehicle) results.
Figure 30:
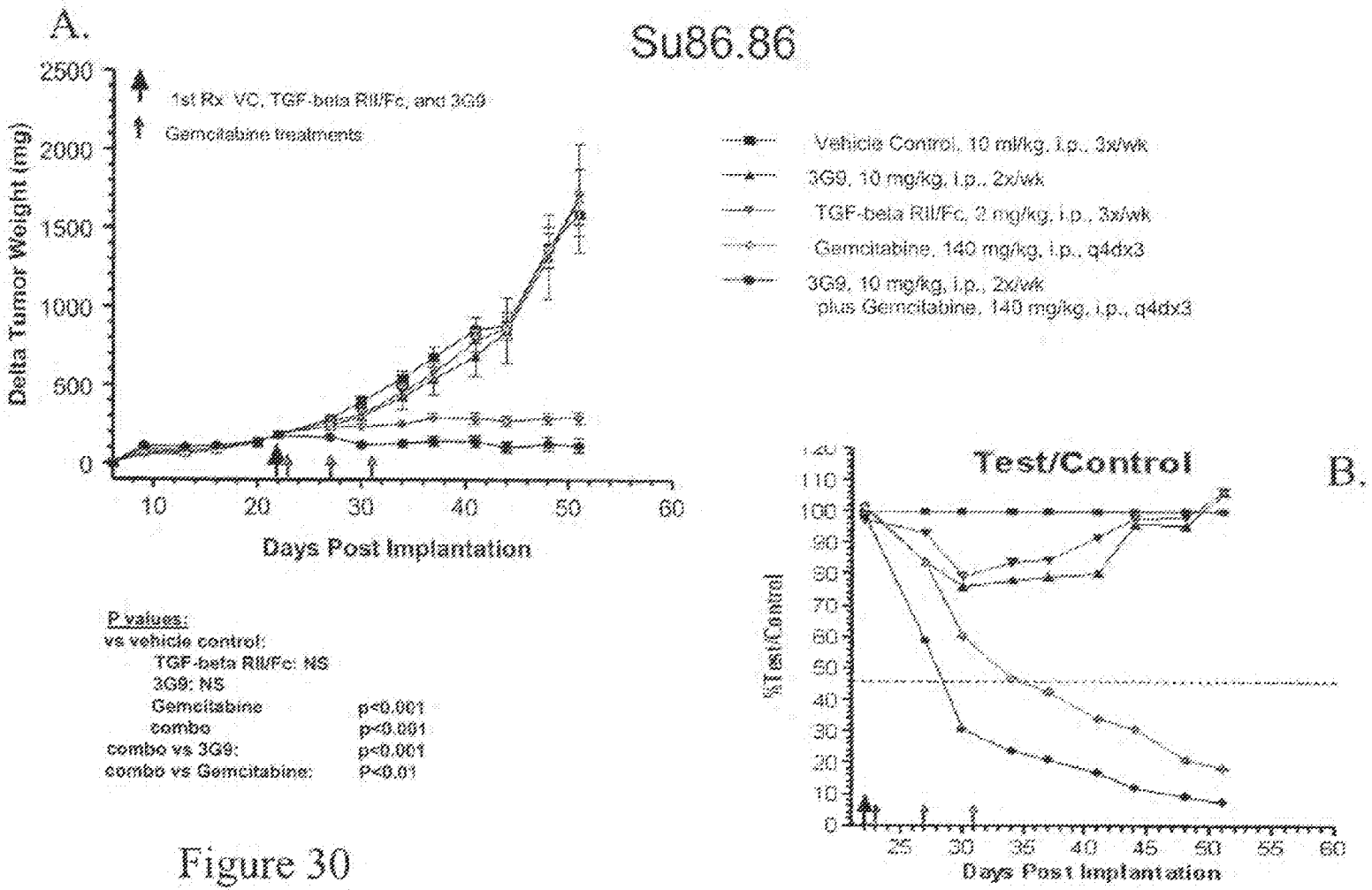
FIG. 30A is a line graph demonstrating the response of Panc04 human pancreatic adenocarcinoma cells, subcutaneously implanted into athymic nude mice, to mAb 3G9 and TGF-β RII-Fc, and to either agent in combination with gemcitabine.
FIG. 30B is a line graph demonstrating the response of Panc04 human pancreatic adenocarcinoma cells, subcutaneously implanted into athymic nude mice, to mAb 3G9 and TGF-β RII-Fc, and to either agent in combination with gemcitabine.
Figure 31A:
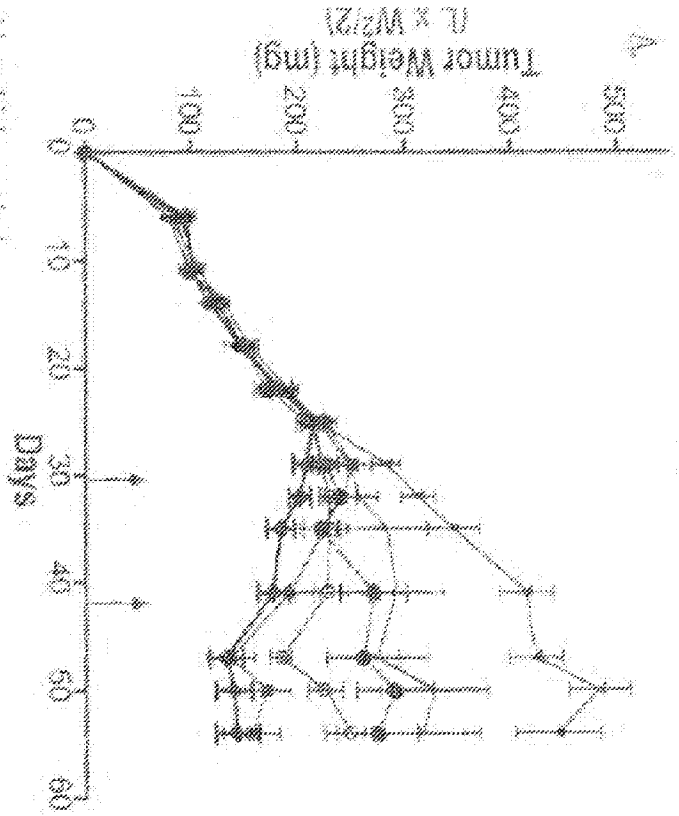
FIG. 31A is a line graph demonstrating the response of Capan-2 human pancreatic adenocarcinoma cells, subcutaneously implanted into athymic nude mice, to mAb 3G9, TGF-β RII-Fc, and gemcitabine, and to each of mAb 3G9 and TGF-β RII-Fc in combination with gemcitabine.
Figure 31B:
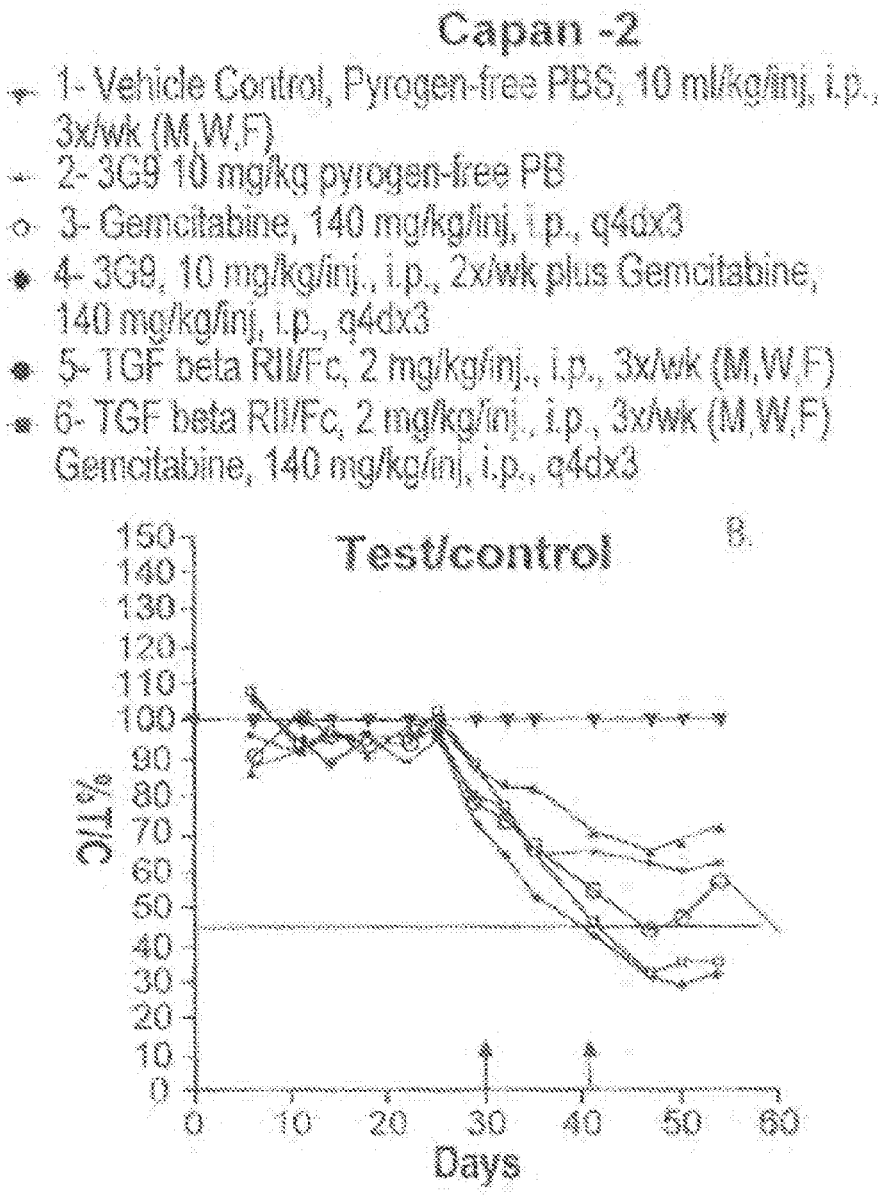
FIG. 31B is a line graph demonstrating the response of Capan-2 human pancreatic adenocarcinoma cells, subcutaneously implanted into athymic nude mice, to mAb 3G9, TGF-β RII-Fc, and gemcitabine, and to each of mAb 3G9 and TGF-β RII-Fc in combination with gemcitabine, expressing the results of test animals as a percentage of control (vehicle) results.
Figure 32A:
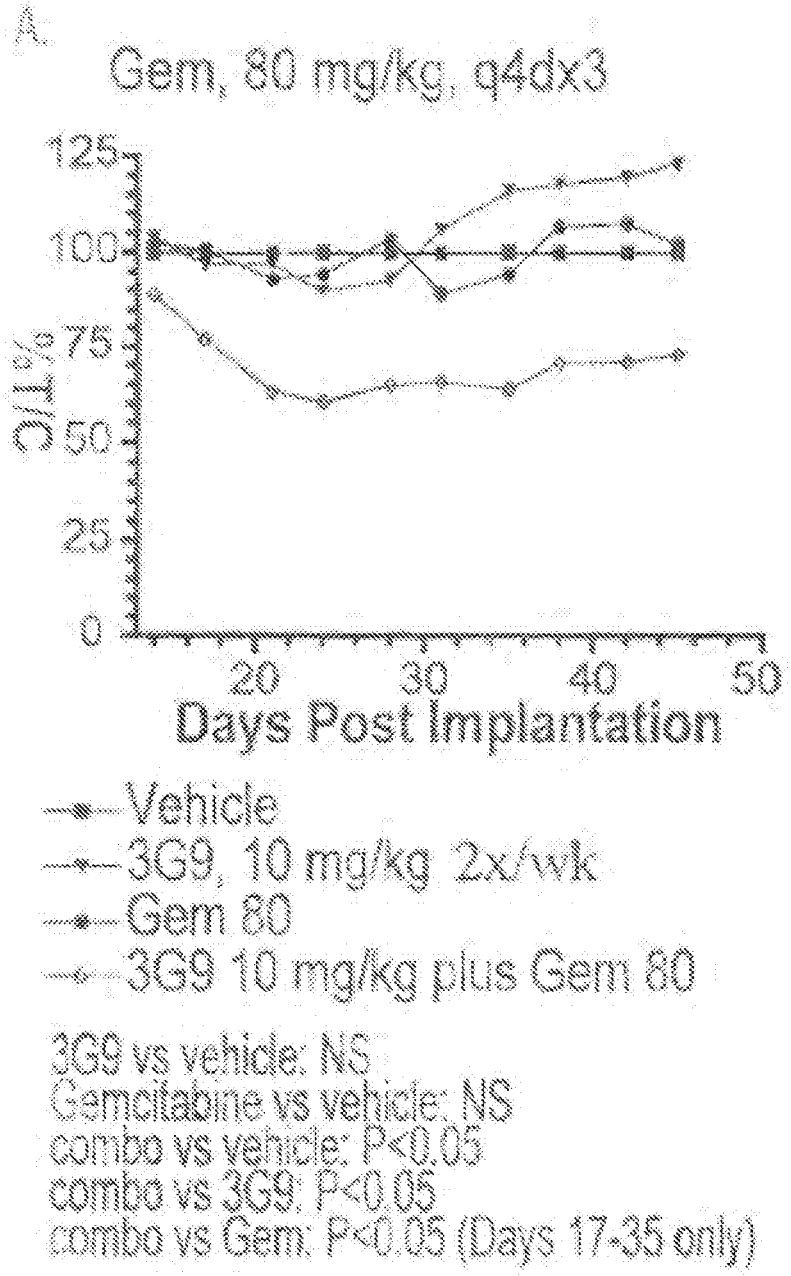
FIGS. 32A-32C are line graphs demonstrating the response of SW1990 human pancreatic adenocarcinoma cells, subcutaneously implanted into athymic nude mice, to mAb 3G9 and gemcitabine, each alone and in combination, expressing the results of test animals as a percentage of control (vehicle) results.
Figure 32B:
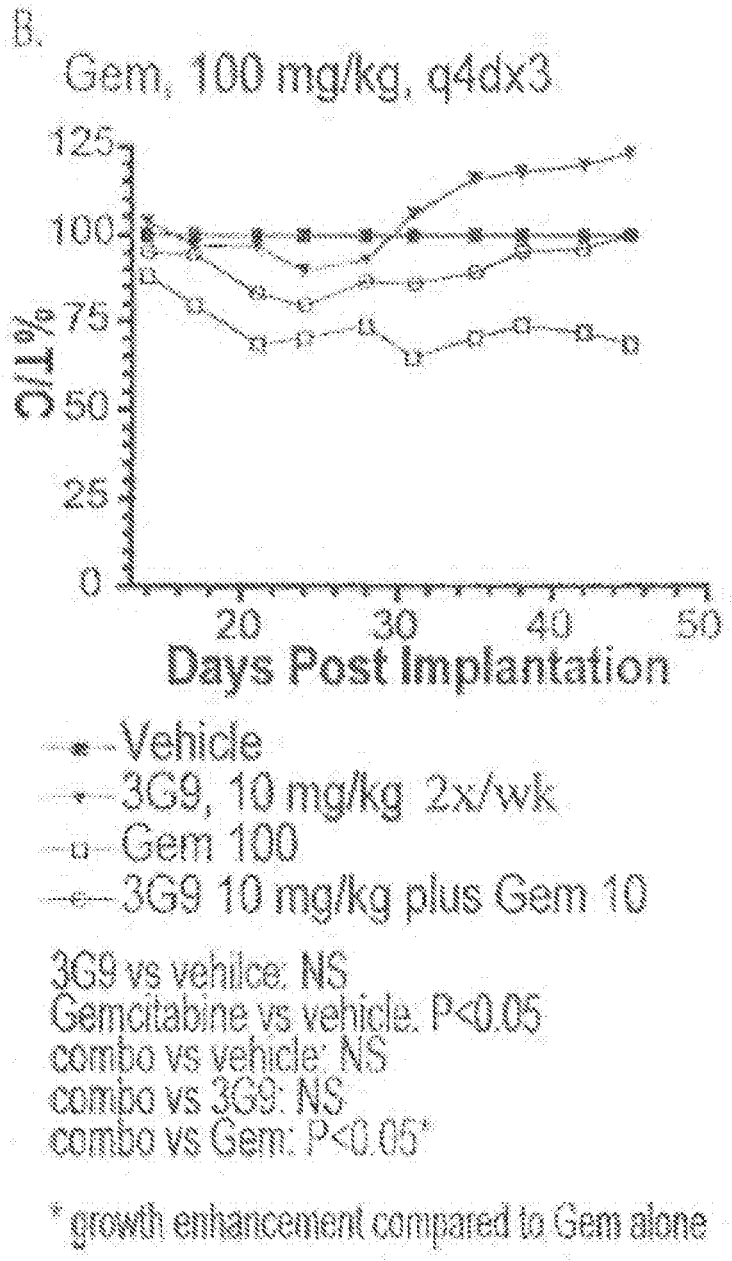
Figure 32C:
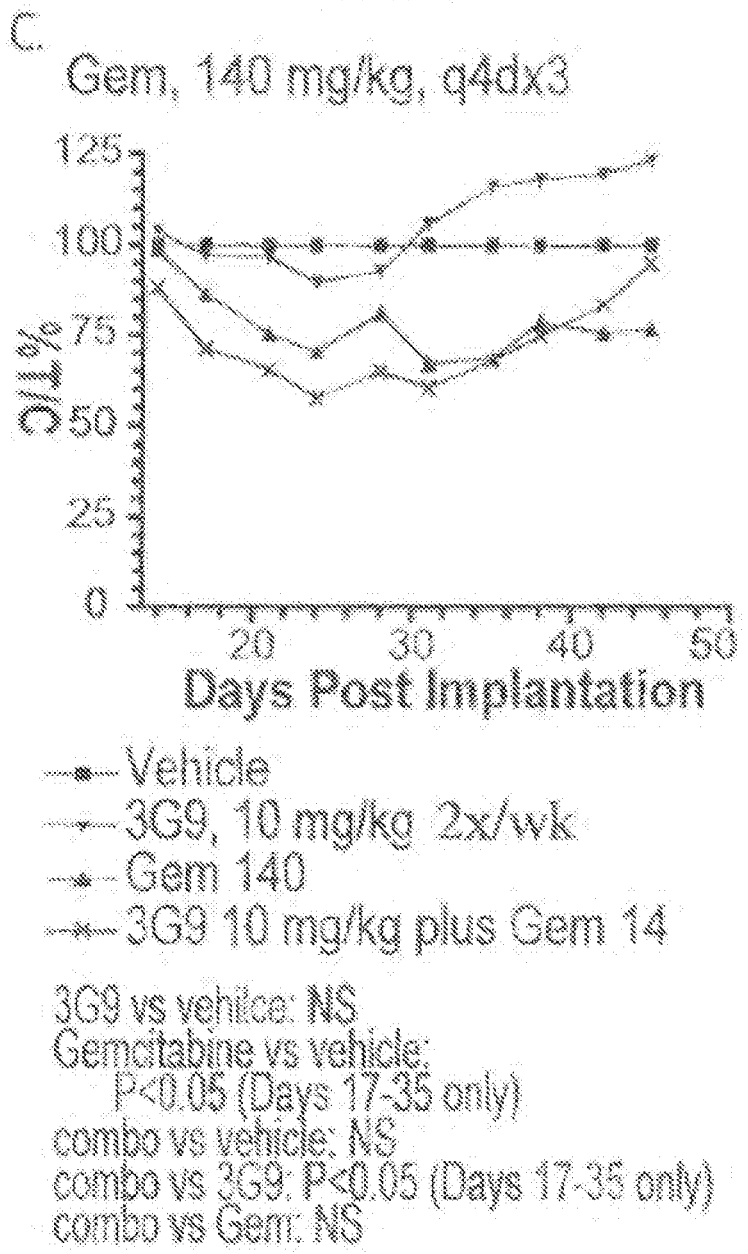
Figure 33:
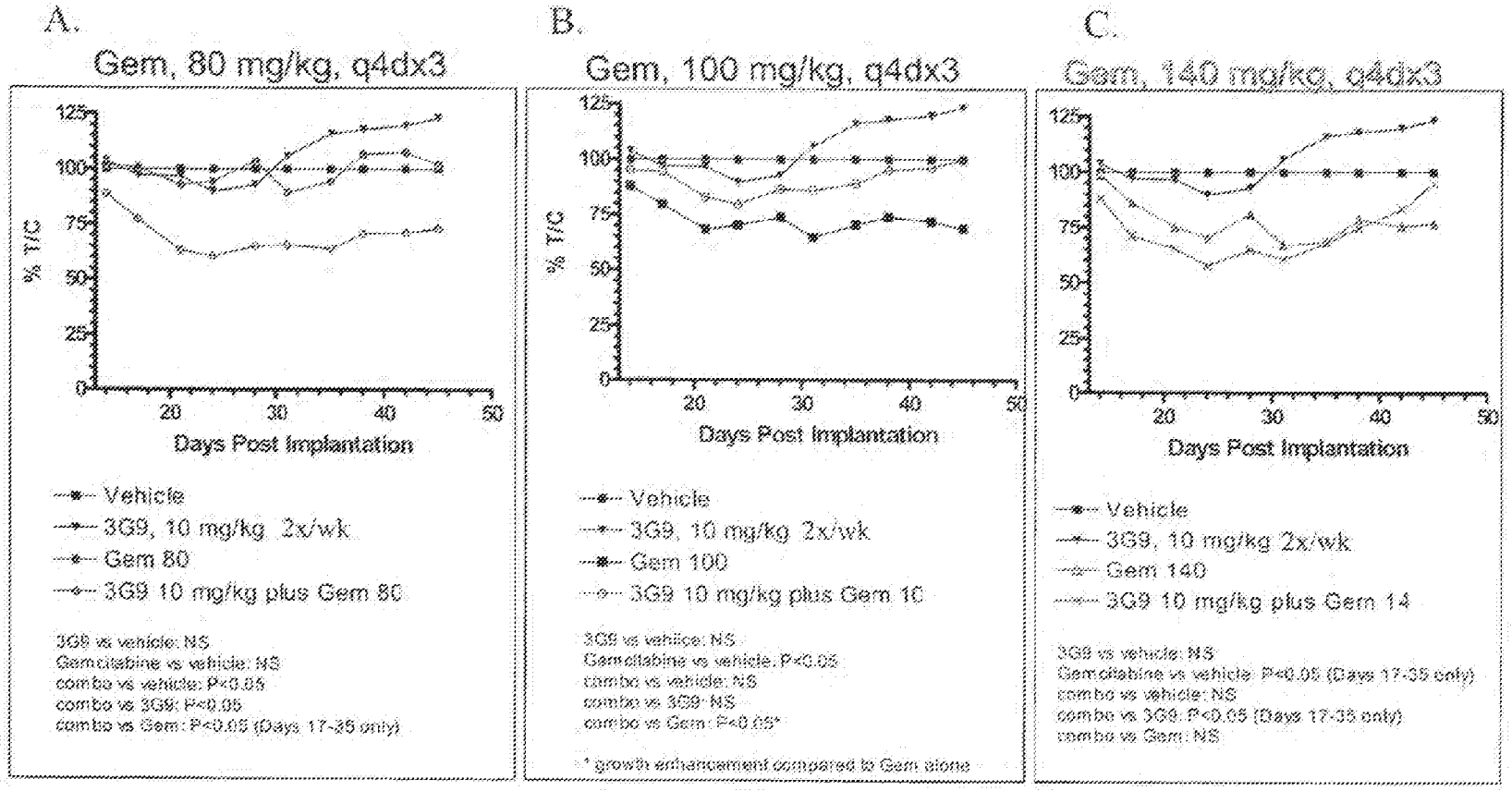
FIG. 33A is a line graph demonstrating the response of Capan-1 human pancreatic adenocarcinoma cells, subcutaneously implanted into athymic nude mice, to mAb 3G9, TGF-β RII-Fc, and gemcitabine, and to each of mAb 3G9 and TGF-β RII-Fc in combination with gemcitabine.
FIG. 33B is a line graph demonstrating the response of Capan-1 human pancreatic adenocarcinoma cells, subcutaneously implanted into athymic nude mice, to mAb 3G9, TGF-β RIT-Fc, and gemcitabine, and to each of mAb 3G9 and TGF-β RII-Fc in combination with gemcitabine, expressing the results of test animals as a percentage of control (vehicle) results.

Similar synergistic effects were observed in mice transplanted with the pancreatic cancer cell lines Su86.6 (FIG. 29), Panc04 (FIG. 30), and Capan-2 (FIG. 31), when treated with a combination of 3G9 and gemcitabine (140 mg/kg). However, when mice transplanted with the pancreatic cell line SW1990 were treated with the same combination therapy, there was no significant difference in therapeutic effect as compared with treatment with gemcitabine alone (see FIG. 32C). When the gemcitabine concentration was lowered to 100 mg/kg, treatment with gemcitabine alone was significantly better than when with the combination therapy (FIG. 32C). When the gemcitabine concentration was decreased even further to 80 mg/kg, treatment with the combination therapy was significantly better than treatment with either gemcitabine or 3G9 alone (FIG. 32A), as observed with the other cell lines at the higher gemcitabine concentration of 140 mg/kg. In a Capan-1 xenograft mode, a combination therapy of antibody 3G9 and gemcitabine was only as effective as gemcitabine alone, and a combination therapy of TGF-β RII-Fc and gemcitabine (FIG. 33).

Figure 34:
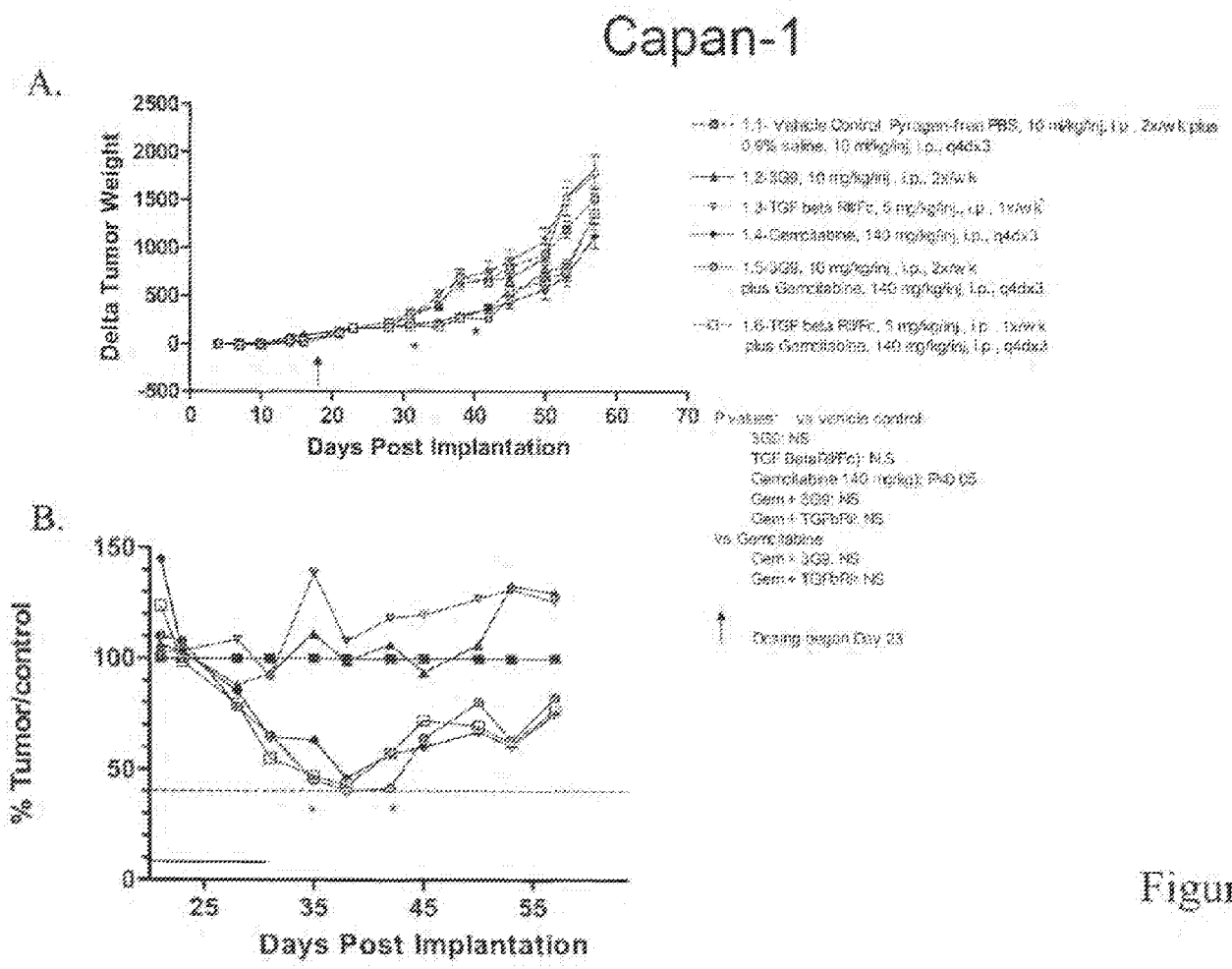
FIG. 34 is a bar graph demonstrating the response of ASPC-1 human pancreatic adenocarcinoma cells orthotopically implanted into athymic nude mice to mAb 3G9, TGF-β RII-Fc, and gemcitabine, and to each of mAb 3G9 and TGF-β RII -Fc in combination with gemcitabine.

Gemcitabine and 3G9 significantly decreased tumor volume in an orthotopic model of pancreatic cancer using cells from the cell line ASPC-1. Treatment with gemcitabine alone or 3G9 alone did not have a significant effect on tumor volume (FIG. 34).

Signaling studies were performed on treated xenograft tumors of BxPC-3, Panc04 and Capan-2. Tumors were harvested at different timepoints following treatment with 3G9 and gemcitabine for the following analyses:

TABLE 3

Summary of signaling studies

| | Read-out | Western | IHC |
|---|---|---|---|
| Tumor Interstitial Fluid Pressure | Fibronectin | X | |
| | Collagen I | | X |
| | SmaI | | X |
| | CD31 | | X |
| Apoptosis | Caspase | | X |
| | TUNEL | | X |
| Survival | p-AKT | X | |
| Proliferation | p-ERK | X | |
| | Ki67 | | X |
| Pathway | p-smad-2 | X | |
| | FAK | X | |

The results of the above studies are summarized in FIG. 35.

Example 5

Figure 37:
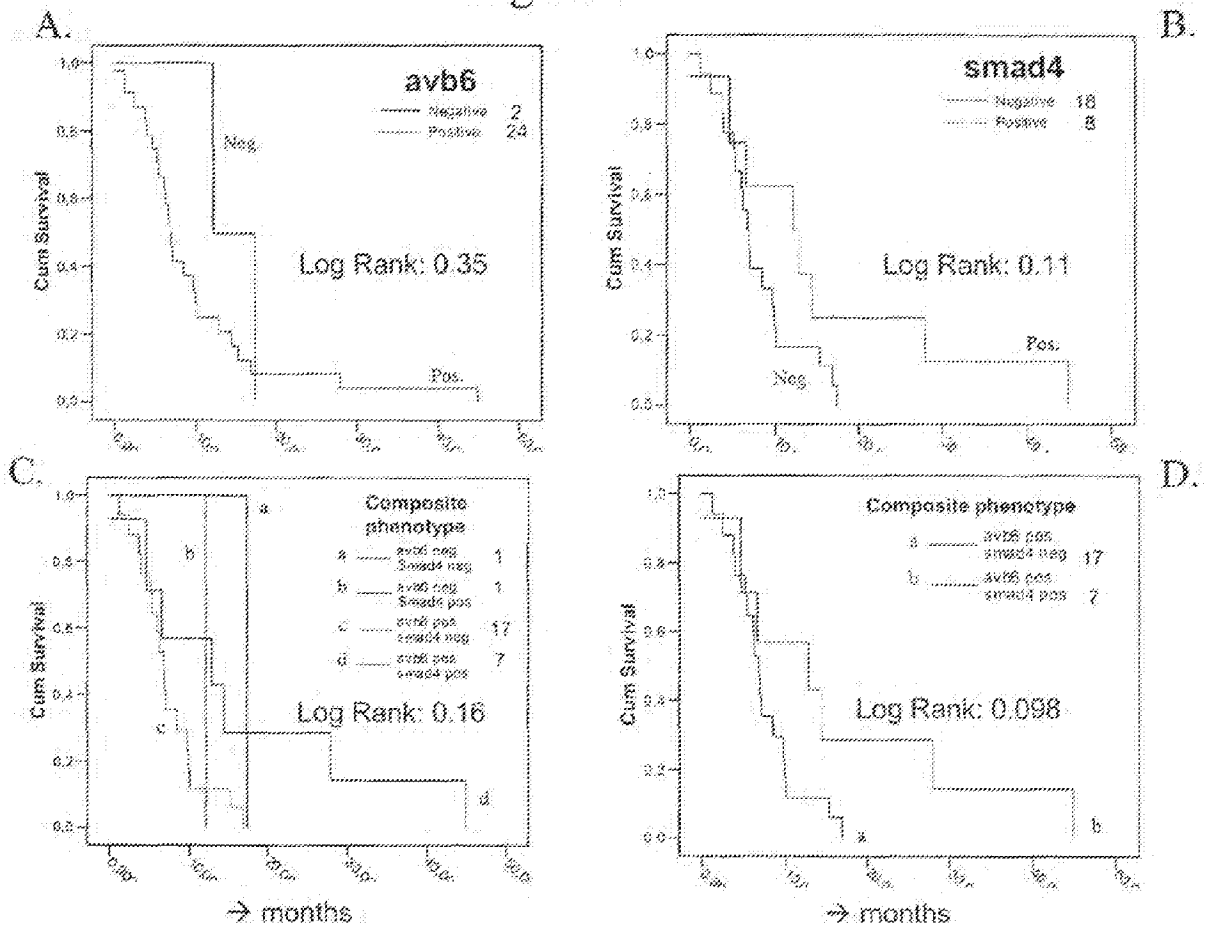
FIG. 37 is a Kaplan-Meier curve representing the cumulative survival of patients with pancreatic ductal adenocarcinoma in function of retention of smad4 or deficiencies of smad4 expression. Only data from primary tumors was analyzed. Log Rank (Mantel-Cox).
Figure 38:
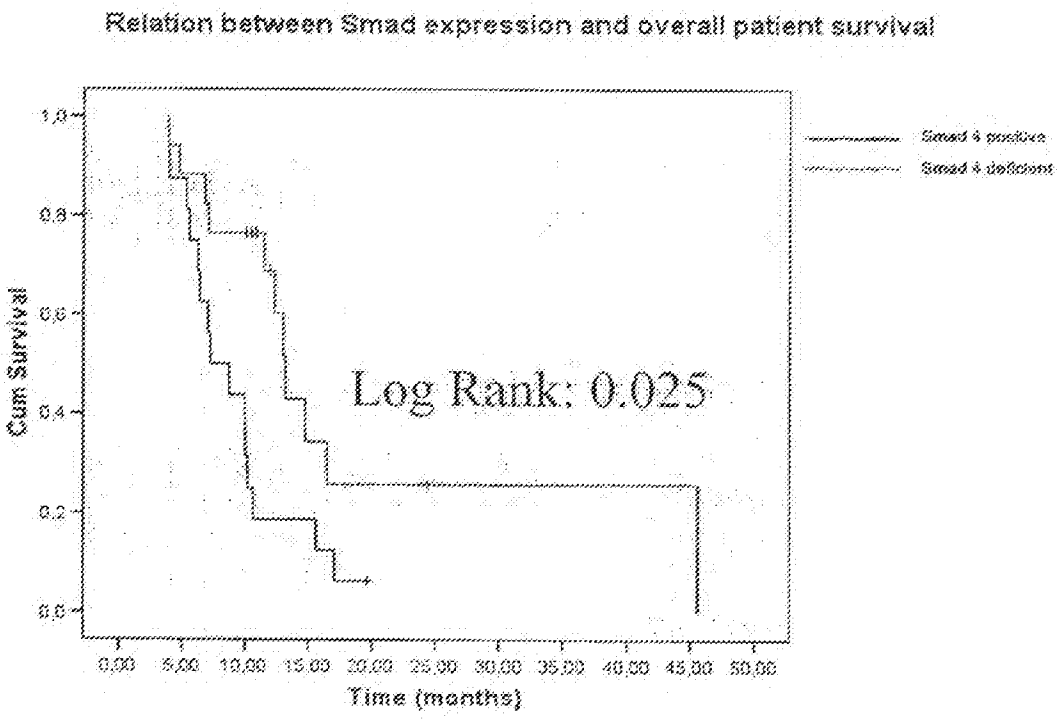
FIG. 38 is a line graph demonstrating the response of SW1990 human pancreatic adenocarcinoma cells, subcutaneously implanted into athymic nude mice (metastatic site: spleen), to mAb 3G9 and soluble TGF-β receptor II/Fc fusion protein (TGF-βRII-Fc).

Survival Phenotypes of a Cohort of 26 Patients of Leiden University Medical Center Survival data for patients diagnosed with pancreatic cancer is shown in FIGS. 36 and 37. The four panels in FIGS. 36 and 37 express the data in terms of avb6 and smad4 expression.

Generally, patients with tumors that express smad4 survive longer than patients with tumors that do not express smad4. Further, patients with an αvβ6+/smad4− phenotype have a significantly reduced survival.

Example 6

Reverse of Growth Inhibition of smad4+/$\alpha_v\beta_6$+ Tumor Cells by anti-$\alpha_v\beta_6$ Ligands The human pancreatic cell line SW1990 was tested in the same xenogeneic mouse system as described in Example 4. Results are depicted in FIGS. 38-41.

Figure 41:
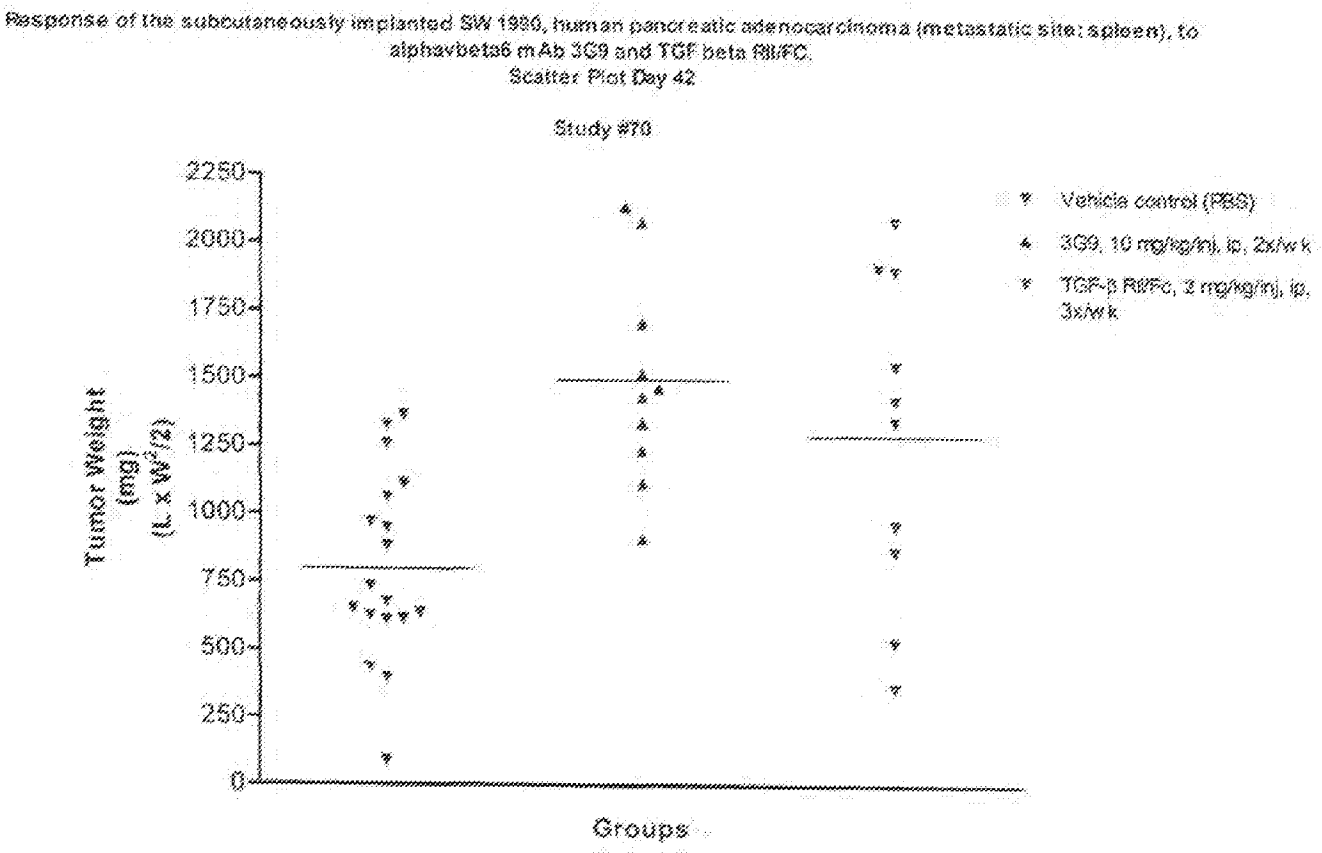
FIG. 41 is a composite figure, showing: A: an autoradiograph of a Western blot showing smad4 expression in SW1990 cell subpopulations sorted based on αvβ6 expression; B: immunohistochemistry of αvβ6 expression in implanted SW1990 tumors; and C-E: FACS-mediated cell sorting of SW1990 cell populations by smad4 and αvβ6 expression.
Figure 42:
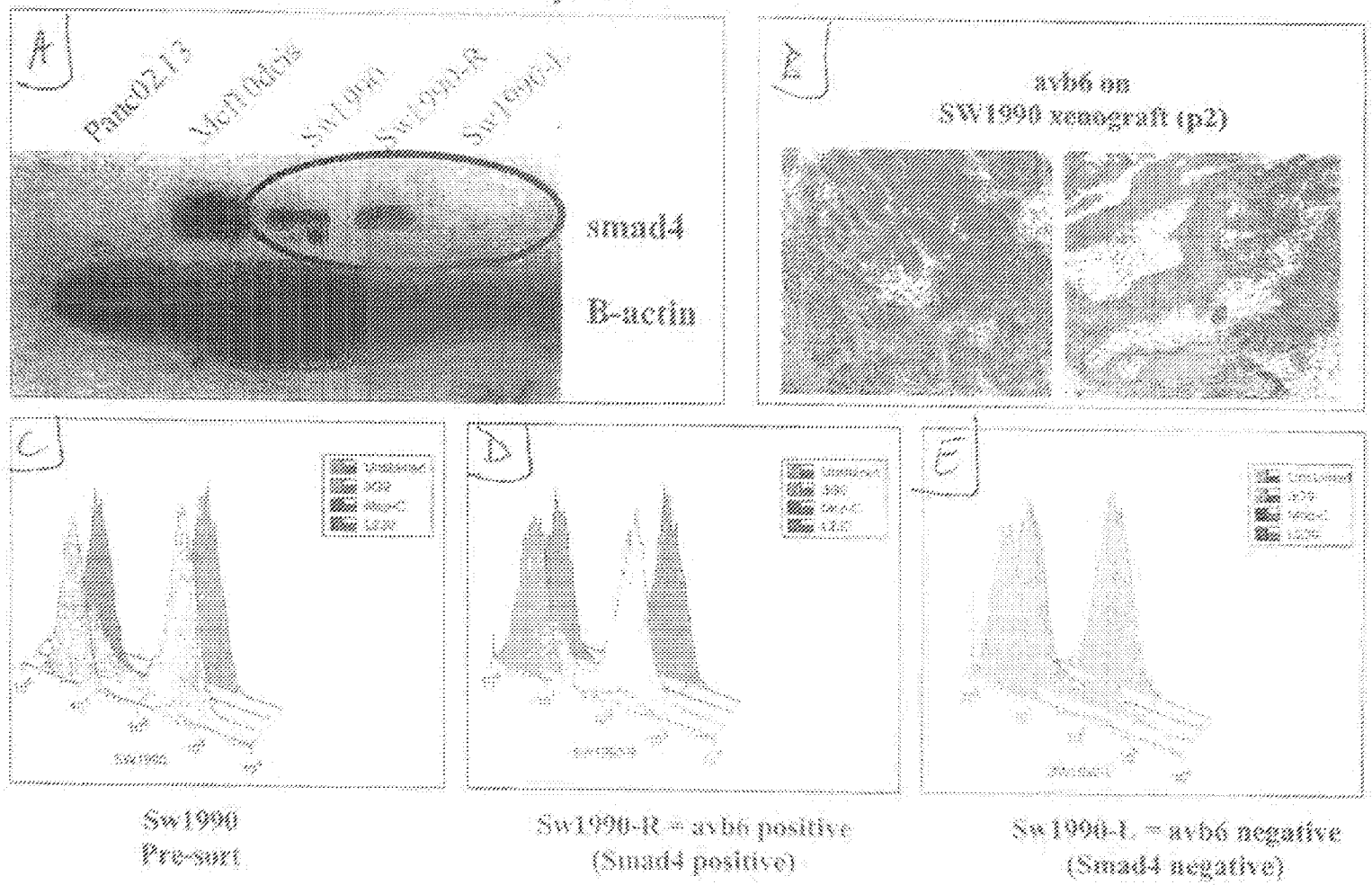
FIG. 42 is a line graph demonstrating the response of Detroit 562 human pharyngeal carcinoma cells, subcutaneously implanted into athymic nude mice, to murine mAb 3G9 and soluble TGF-β receptor II/Fc fusion protein (TGF-βRII-Fc).
Figure 43:
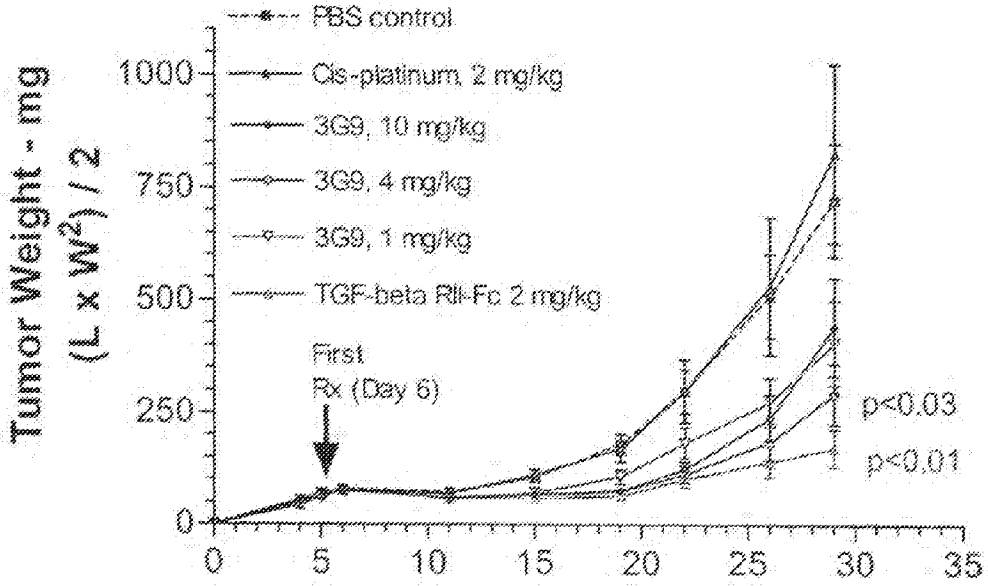
FIG. 43 is a scatter plot demonstrating the response of Detroit 562 human pharyngeal carcinoma cells, subcutaneously implanted into athymic nude mice, to murine mAb 3G9, mAb 4B4, and soluble TGF-β receptor II/Fc fusion protein (TGF-βRII-Fc), at day 39 of the treatment regimen.
Figure 44:
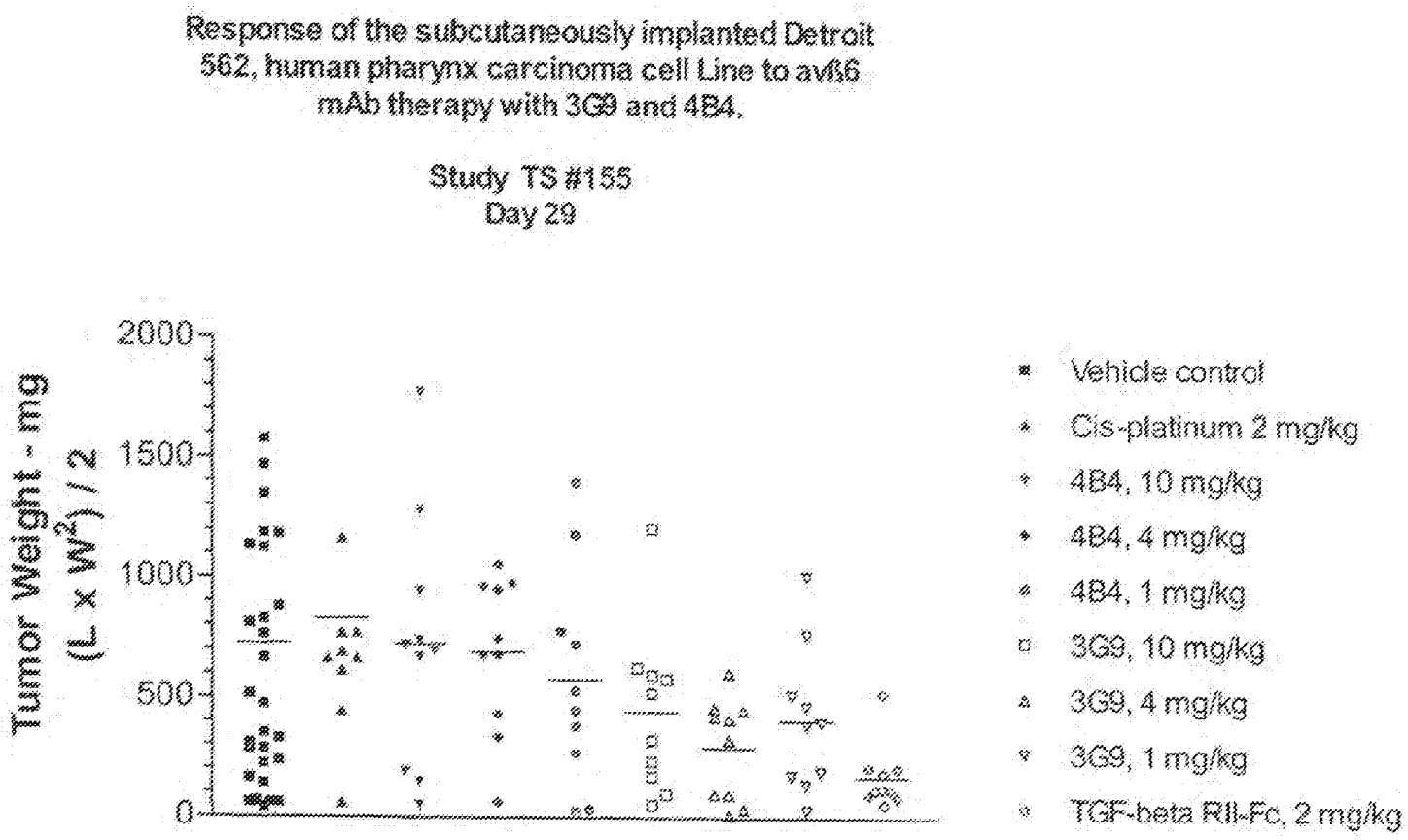
FIG. 44 is a line graph demonstrating the response of Detroit 562 human pharyngeal carcinoma cells, subcutaneously implanted into athymic nude mice, to murine mAb 3G9, mAb 4B4, and soluble TGF-β receptor II/Fc fusion protein (TGF-βRII-Fc).
Figure 45:
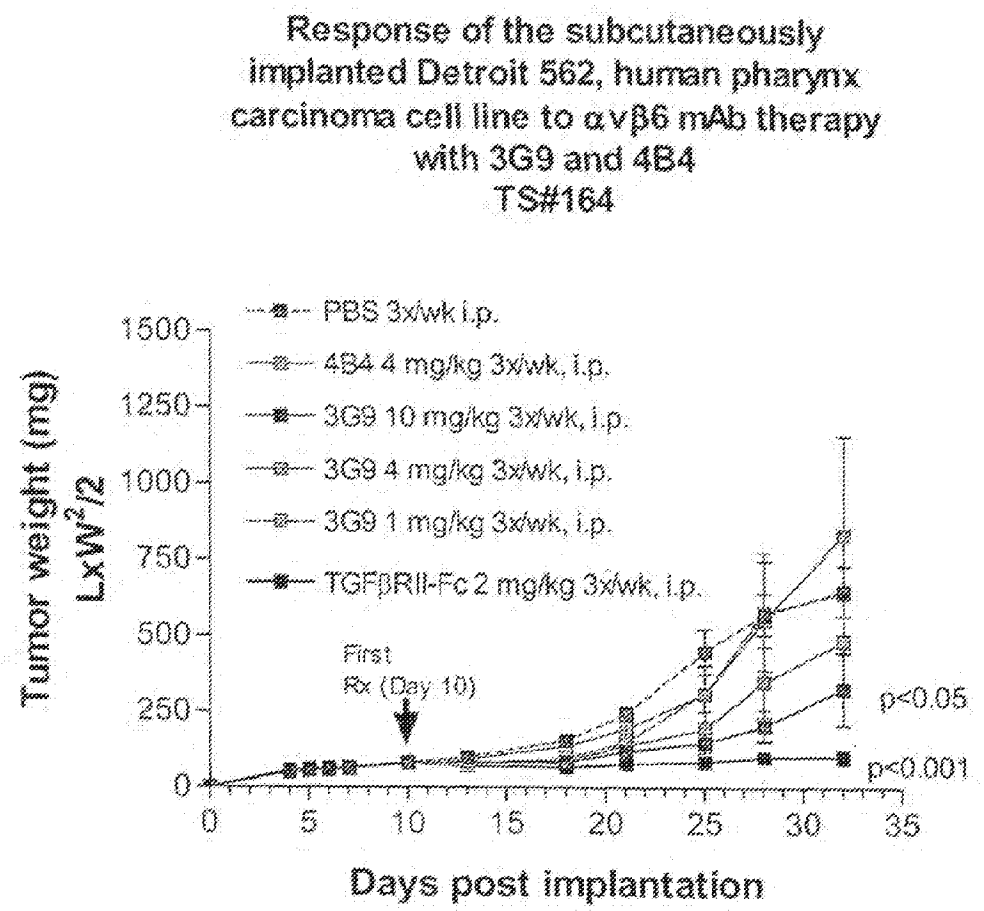
FIG. 45 is a line graph demonstrating the response of Detroit 562 human pharyngeal carcinoma cells, subcutaneously implanted into athymic nude mice, to murine mAb 3G9, mAb 4B4, mAb 8G6, and soluble TGF-β receptor II/Fc fusion protein (TGF-βRII-Fc).
Figure 46:
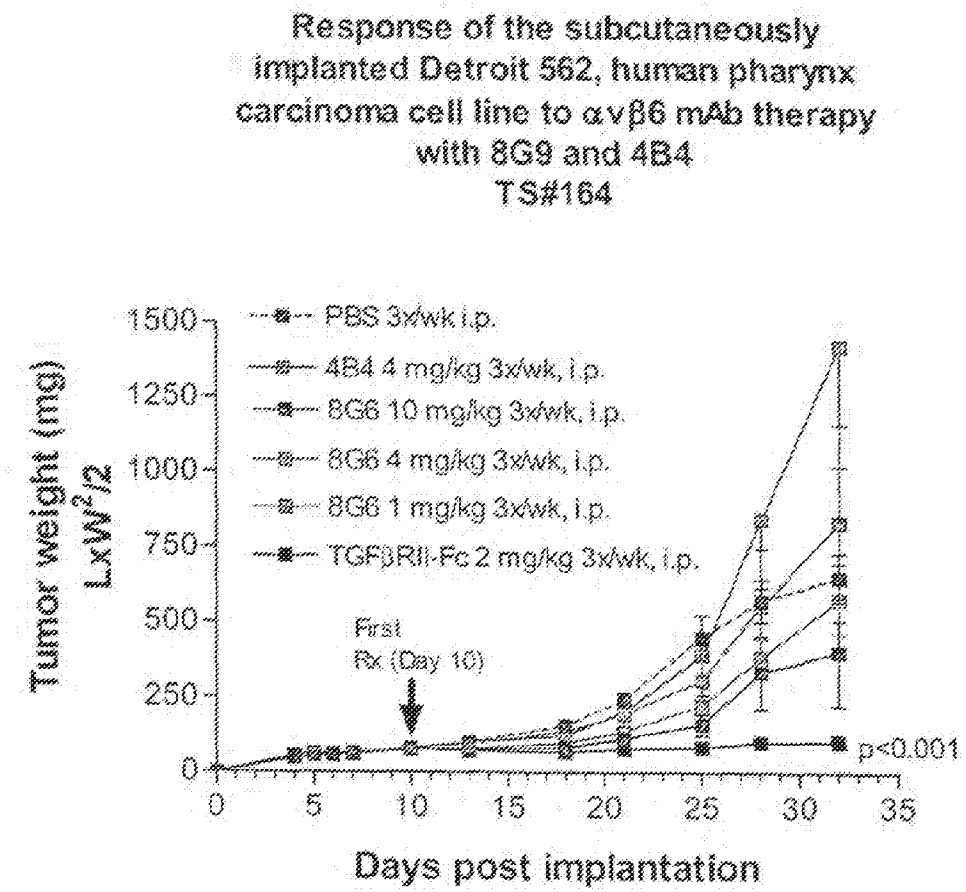
FIG. 46 is a scatter plot demonstrating the response of Detroit 562 human pharyngeal carcinoma cells, subcutaneously implanted into athymic nude mice, to murine mAb 3G9, mAb 4B4, mAb 8G6, and soluble TGF-β receptor II/Fc fusion protein (TGF-βRII-Fc), at day 34 of the treatment regimen.
Figure 47:
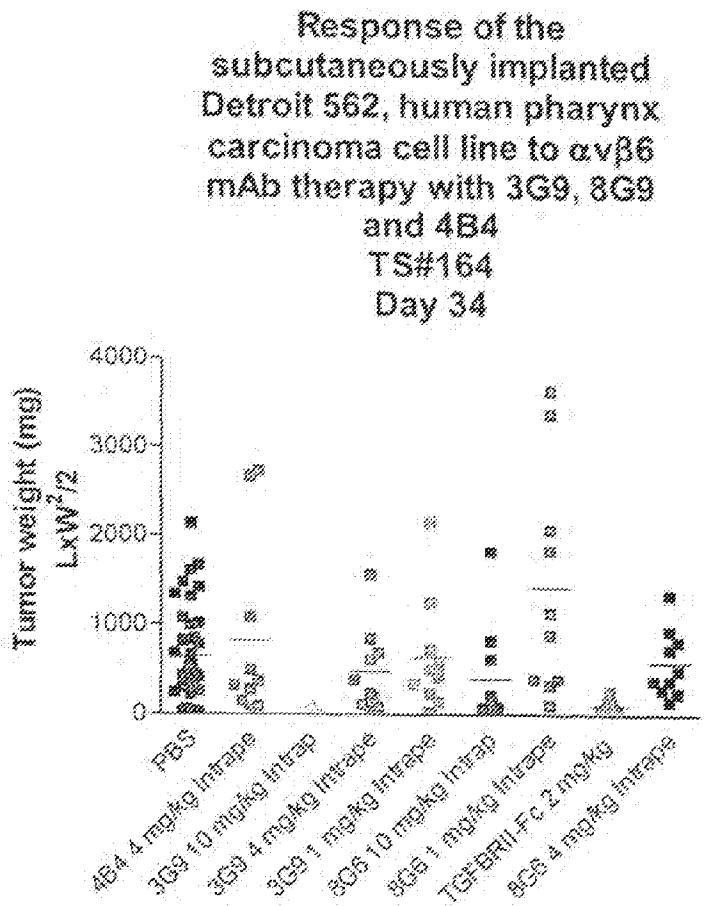
FIG. 47 is a pair of line graphs demonstrating the response of Detroit 562 human pharyngeal carcinoma cells, subcutaneously implanted into athymic nude mice, to murine mAb 3G9 (top) and to humanized mAb 3G9 (BG00011) (bottom).
Figure 48:
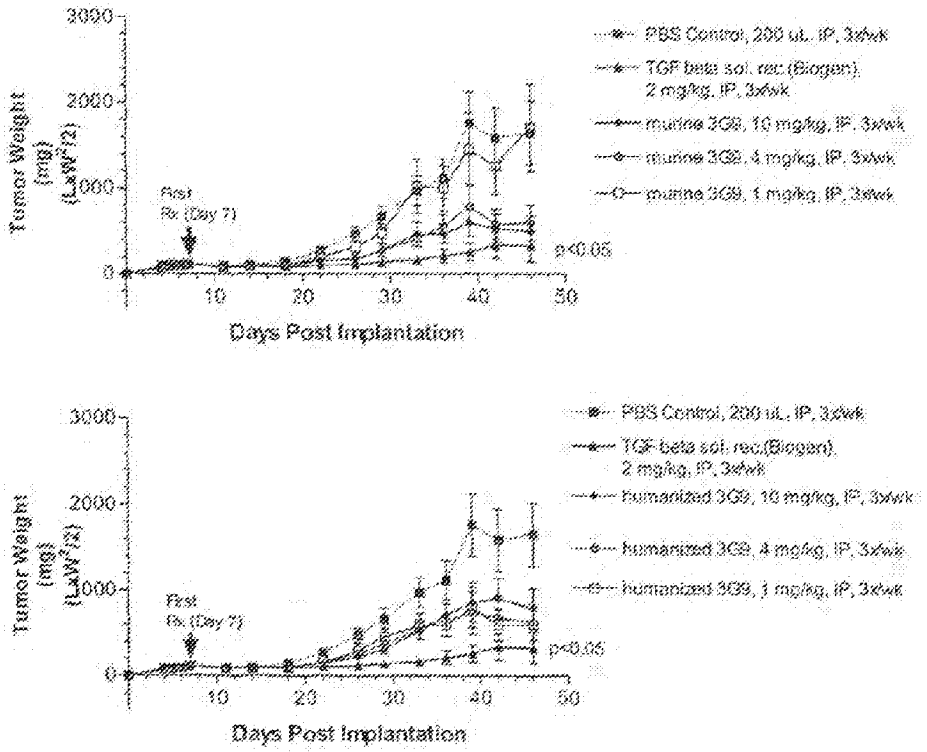
FIG. 48 is a scatter plot demonstrating the response of Detroit 562 human pharyngeal carcinoma cells, subcutaneously implanted into athymic nude mice, to murine mAb 3G9 (top) and to humanized mAb 3G9 (BG00011) (bottom).
Figure 49:
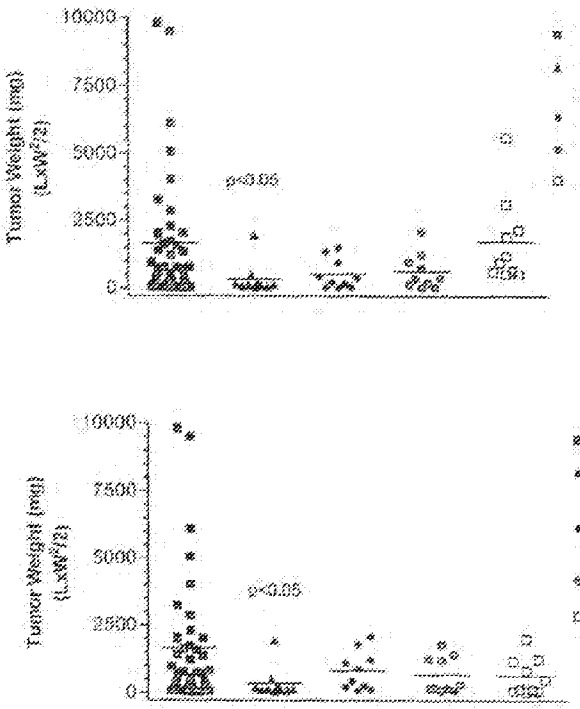
FIG. 49 is a line graph demonstrating the response of Detroit 562 human pharyngeal carcinoma cells, subcutaneously implanted into athymic nude mice, to murine mAb 3G9 and to humanized mAb 3G9 (BG00011), expressing the results of test animals as a percentage of control (vehicle as negative; TGF-β RII-Fc as positive) results.
Figure 50:
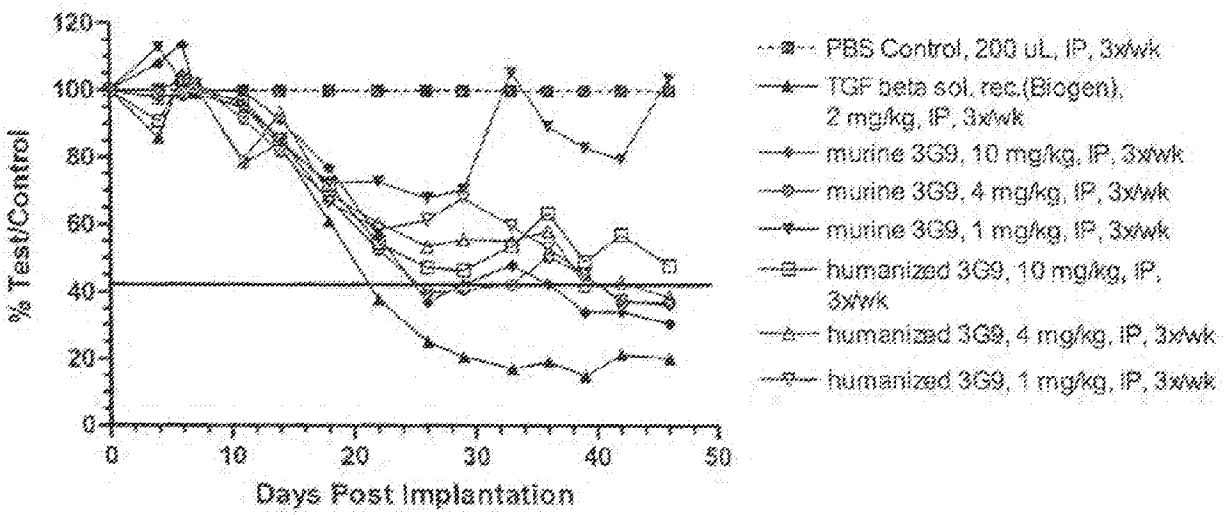
FIG. 50 is a line graph demonstrating the response of Detroit 562 human pharyngeal carcinoma cells, subcutaneously implanted into athymic nude mice, to wildtype murine mAb 3G9.
Figure 51:
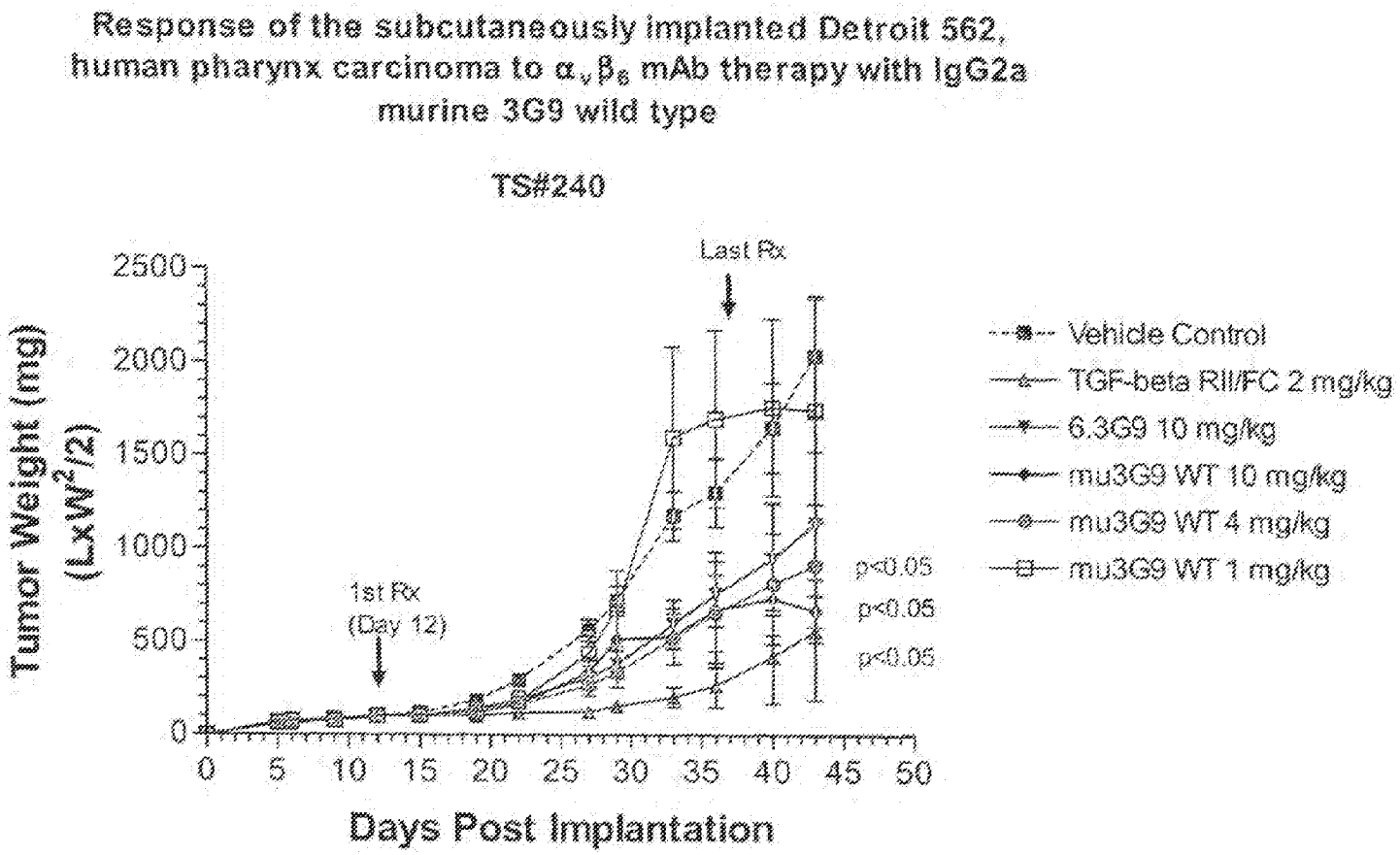
FIG. 51 is a line graph demonstrating the response of Detroit 562 human pharyngeal carcinoma cells, subcutaneously implanted into athymic nude mice, to aglycosyl murine mAb 3G9.
Figure 52:
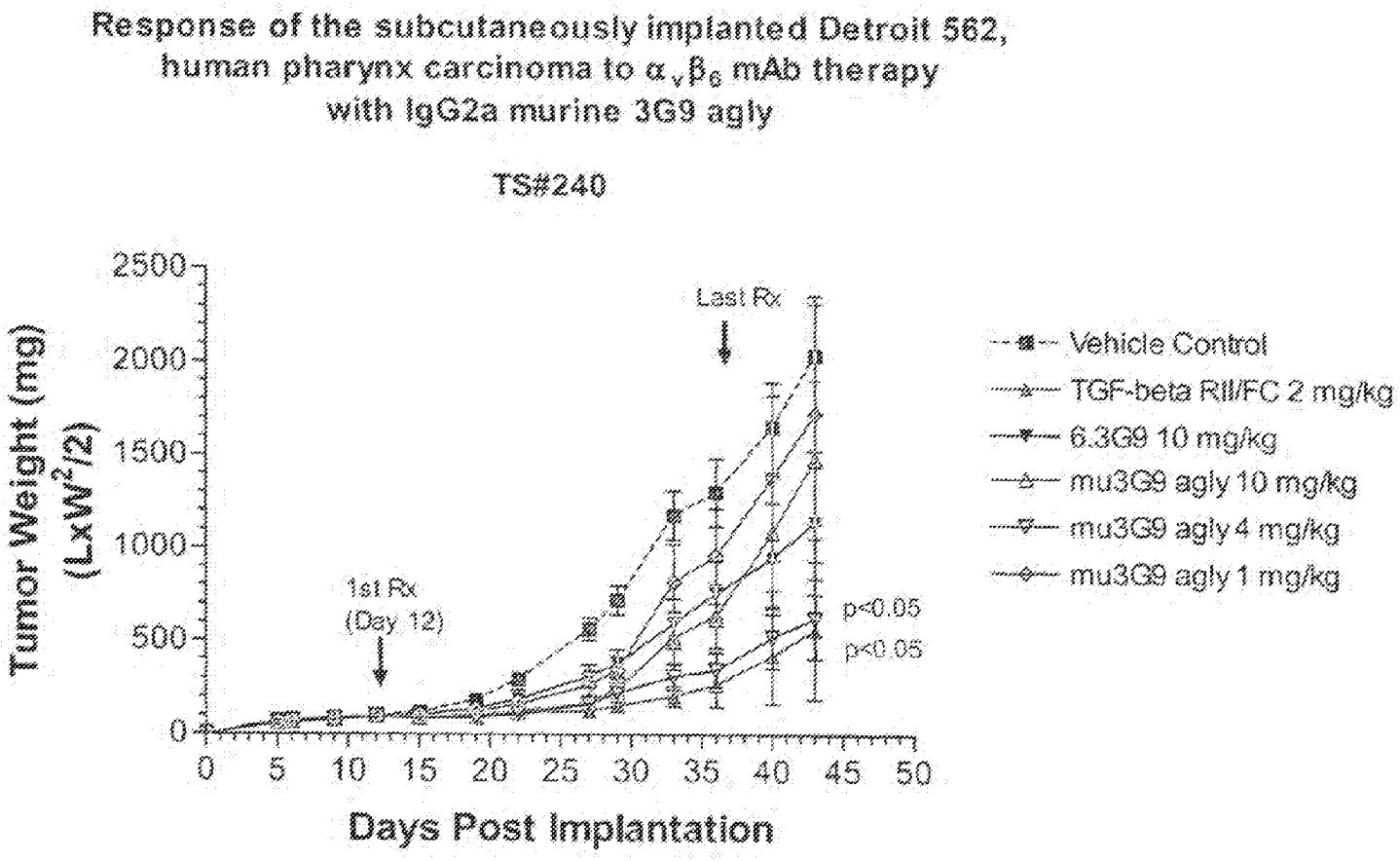
FIG. 52 is a scatter plot demonstrating the response of Detroit 562 human pharyngeal carcinoma cells, subcutaneously implanted into athymic nude mice, to wildtype murine mAb 3G9 and to algycosyl murine mAb 3G9.
Figure 53:
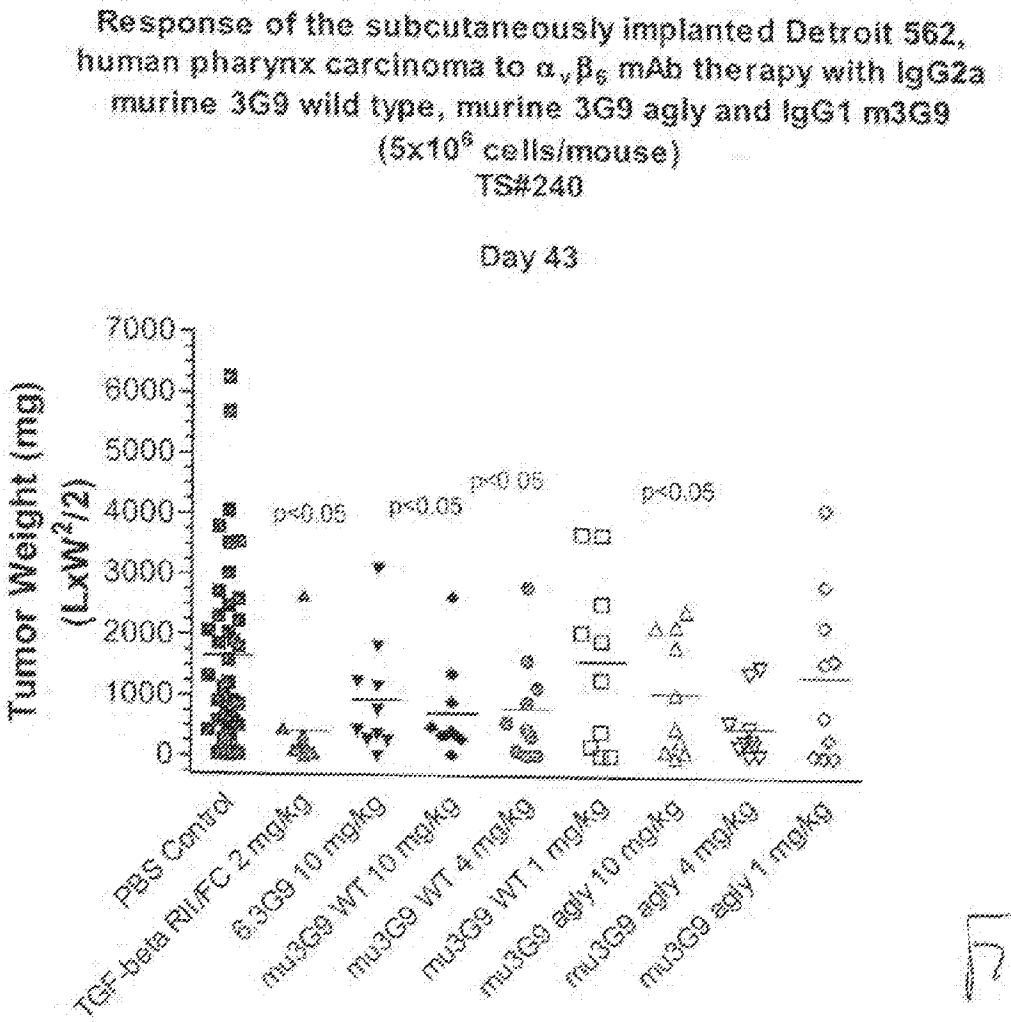
FIG. 53 is a line graph demonstrating the response of Detroit 562 human pharyngeal carcinoma cells, subcutaneously implanted into athymic nude mice, to wildtype murine mAb 3G9 and to algycosyl murine mAb 3G9, expressing the results of test animals as a percentage of control (vehicle) results.
Figure 54:
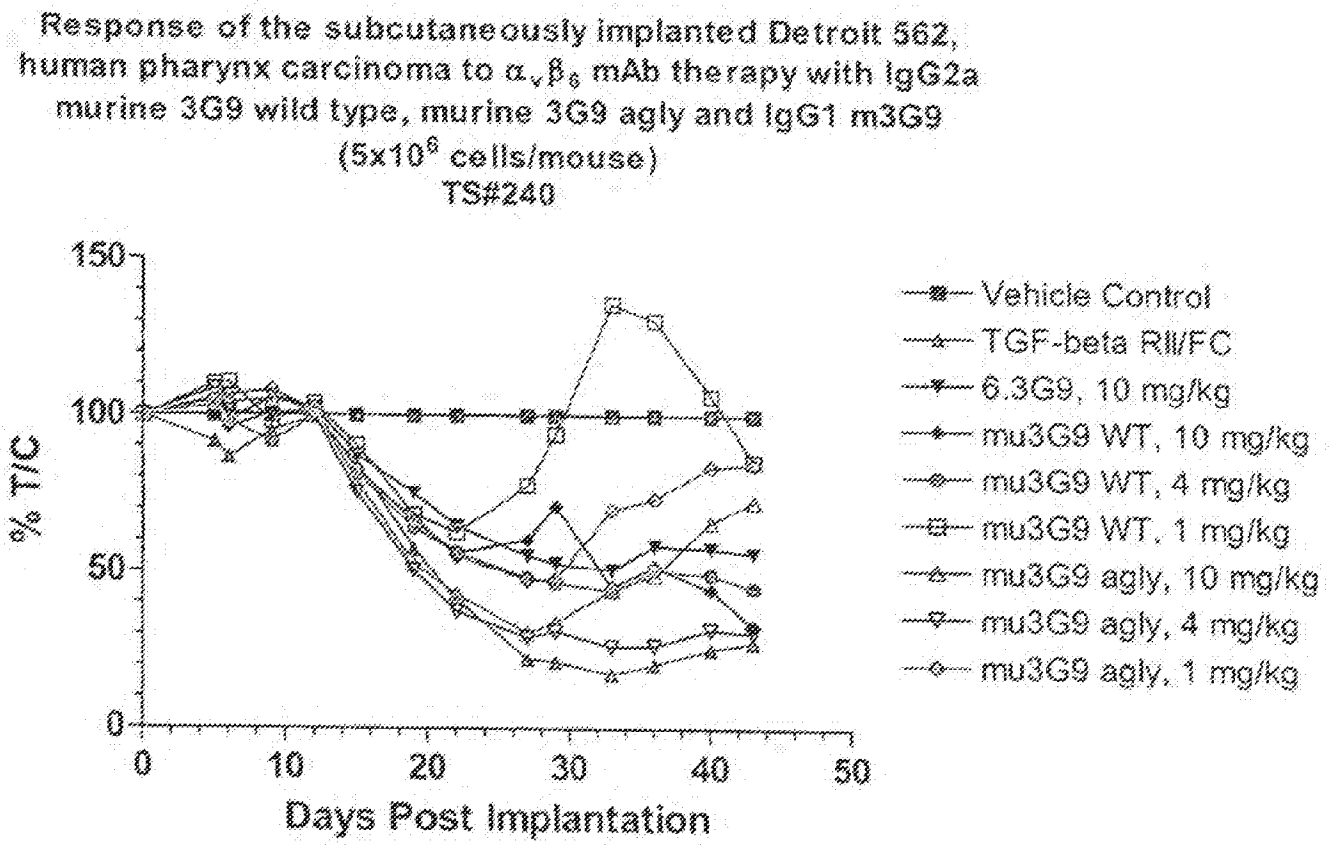
FIG. 54 is a Table summarizing the results of FIGS. 43-52.

The SW1990 cell line showed heterogeneity of αvβ6 expression. The cell line was sorted and enriched for αvβ6 positive and αvβ6 negative cells (FIG. 41 C-E). Western blot analysis of the resulting variants showed that the αvβ6 positive population was smad4+, while the αvβ6 negative population was smad4− (FIG. 41A). Thus, the αvβ6 positive SW1990 cell line does not fit the profile of the BxPC-3 line in which we saw inhibition of tumor growth by αvβ6 blocking mAb 3G9, especially in combination with chemotreatment (Example 4). Since tissue sections of the SW1990 xenograft showed αvβ6 expression (FIG. 41B), it is therefore expected that these cells in vivo are in fact smad4+.

Figure 39:
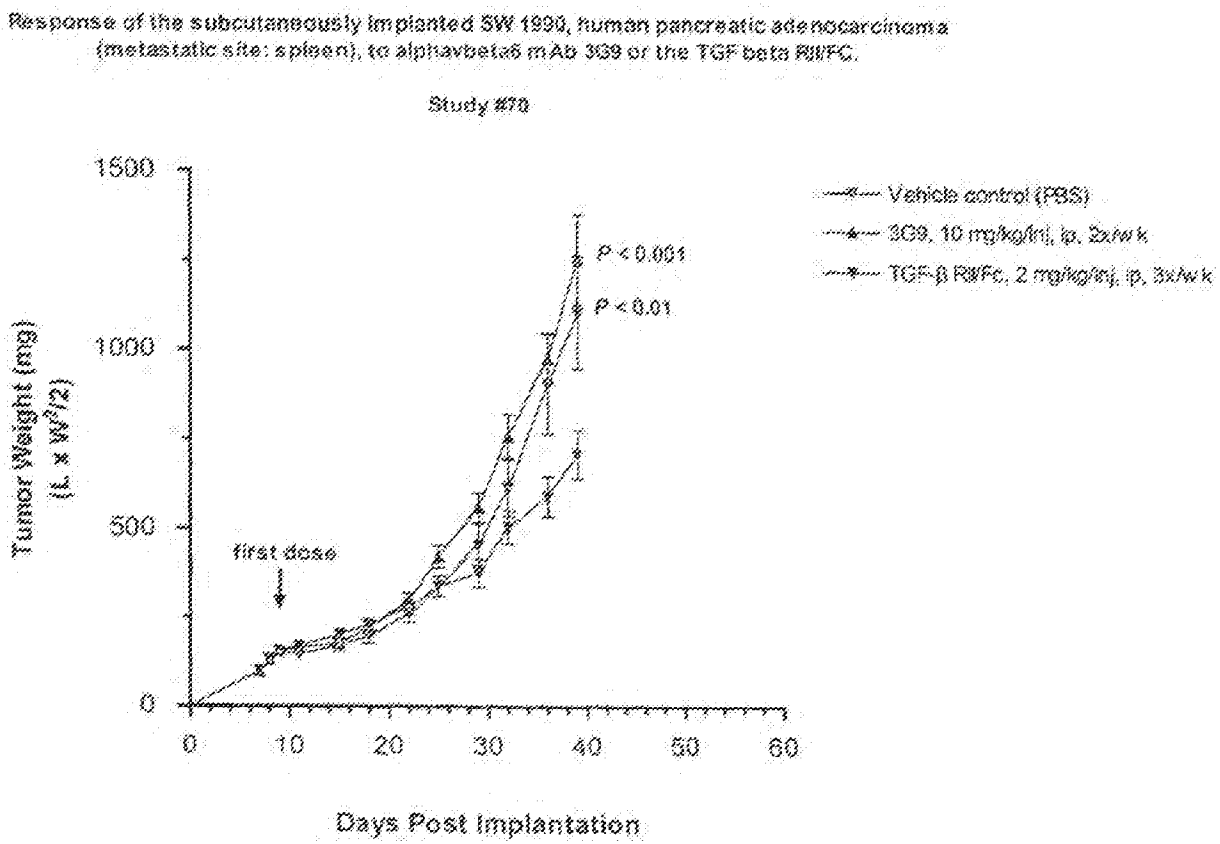
FIG. 39 is a line graph demonstrating the response of SW1990 human pancreatic adenocarcinoma cells, subcutaneously implanted into athymic nude mice (metastatic site: spleen), to mAb 3G9 and soluble TGF-βRII-Fc, expressing the results of test animals as a percentage of control (vehicle) results.
Figure 40:
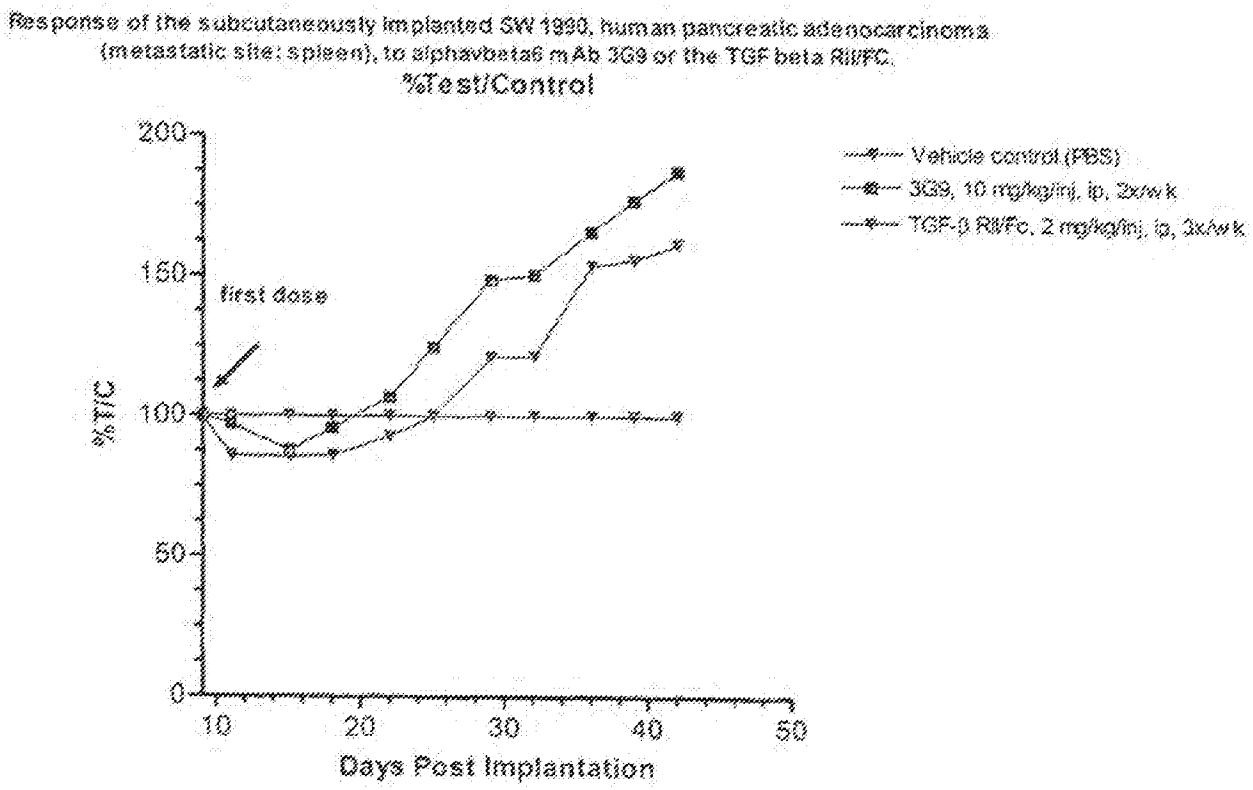
FIG. 40 is a scatter plot demonstrating the response of SW1990 human pancreatic adenocarcinoma cells, subcutaneously implanted into athymic nude mice (metastatic site: spleen), to mAb 3G9 and soluble TGF-βRII-Fc, at day 42 of the treatment regimen.

Mice implanted with SW1990 cells were then treated in vivo with murine mAb 3G9 or with soluble TGF-β RII-Fc as described in Example 4, and were assessed for tumor growth over time. The results are shown in FIGS. 39-41, which demonstrate that in contrast to the pancreatic tumor line BxPC-3, SW1990 tumors are not inhibited from growth by treatment with the anti-αvβ6 3G9 mAb, but instead demonstrate a slight increase in cell growth. The inverse effect of treatment with 3G9 or sol TGF-β RII on growth in SW 1990 can be explained by reasoning that in the presence of smad4, TGF-β can induce a growth inhibitory signal, which is abrogated when TGF-β (activation) is blocked by soluble TGF-β RII and/or 3G9.

These results suggest that in order to be responsive to αvβ6 ligands, tumor cells must be deficient in smad4 expression, since the smad4+ cell line SW 1990 was not growth-inhibited by anti-αvβ6 mAbs, while the smad4−cell line BxPC-3 was. These results thus are consistent with the hypothesis and support the responsiveness in a selected set of pancreatic cancer patients (smad4−/αvβ6+), indicating that a useful clinical marker to predict the sensitivity or responsiveness of tumor cells, particularly pancreatic tumor cells, to αvβ6-active ligands or chemosenstitization therewith, would be to determine the level of expression of smad4 in those tumor cells.

Example 7

Growth Inhibition of Detroit 562 Human Pharyngeal Carcinoma Cells by $\alpha_v\beta_6$ mAbs In a xenogeneic study, Detroit 562 human pharyngeal carcinoma cells were implanted subcutaneously into mice according to the protocol described in Example 4. Tumor growth was then assessed over time as described in the earlier Examples. Results are shown in FIGS. 42-54. These results indicate that in the Detroit 562 model, murine and humanized 3G9 anti-αvβ6 mAbs were able to significantly inhibit the growth of tumors, while other anti-αvβ6 mAbs (notably murine 4B4) were less effective.

Example 8

Relevance of αvβ6 Blockade in Pancreatic Cancer

Smad4 is inactivated in about 55% of pancreatic adenocarcinomas (Tascilar et al., Clin. Cancer Res. 4:4115-4121, 2001). Löhr et al. (Cancer Res. 61:550-555, 2001) reported that TGFβ confers desmoplastic potential in pancreatic cancer, which causes fibrosis. This desmoplastic potential, however, correlated with smad4 expression. We observed that human pancreatic cell lines that were smad4 null (AsPC-2, BxPC-3, Capan-1, and Capan-2), induced desmoplasia when transplanted into mice, while cell lines that carried wildtype smad4 (PaCa-2, PaCa-3, PaCa-44, and PANC-1) did not induce desmoplasia (see Table 1 of Lohr et al.).

Summary of results: We have discovered that αvβ6 is highly upregulated in pancreatic cancer. We also obtained efficacy data with αvβ6 mAb (3G9) in vivo, determining single agent efficacy in a pharyngeal cancer model and in two pancreatic cancer models. We also observed that treatment with a combination of 3G9 and gemcitabine demonstrated increased efficacy over gemcitabine alone in 5 of 7 pancreatic xenograft models (FIG. 35).

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

---

SEQUENCE LISTING

```
<160> NUMBER OF SEQ ID NOS: 33

<210> SEQ ID NO 1
<211> LENGTH: 10
<212> TYPE: PRT
<213> ORGANISM: Artificial
<220> FEATURE:
<223> OTHER INFORMATION: Synthetic

<400> SEQUENCE: 1

Ser Tyr Thr Phe Thr Asp Tyr Ala Met His
1               5                   10


<210> SEQ ID NO 2
<211> LENGTH: 10
<212> TYPE: PRT
<213> ORGANISM: Artificial
<220> FEATURE:
<223> OTHER INFORMATION: Synthetic

<400> SEQUENCE: 2

Ser Tyr Thr Phe Thr Asp Tyr Thr Met His
1               5                   10
```

<210> SEQ ID NO 3
<211> LENGTH: 10
<212> TYPE: PRT
<213> ORGANISM: Artificial
<220> FEATURE:
<223> OTHER INFORMATION: Synthetic

<400> SEQUENCE: 3

Gly Phe Thr Phe Ser Arg Tyr Val Met Ser
1 5 10

<210> SEQ ID NO 4
<211> LENGTH: 10
<212> TYPE: PRT
<213> ORGANISM: Artificial
<220> FEATURE:
<223> OTHER INFORMATION: Synthetic

<400> SEQUENCE: 4

Gly Tyr Asp Phe Asn Asn Asp Leu Ile Glu
1 5 10

<210> SEQ ID NO 5
<211> LENGTH: 10
<212> TYPE: PRT
<213> ORGANISM: Artificial
<220> FEATURE:
<223> OTHER INFORMATION: Synthetic

<400> SEQUENCE: 5

Gly Tyr Ala Phe Thr Asn Tyr Leu Ile Glu
1 5 10

<210> SEQ ID NO 6
<211> LENGTH: 17
<212> TYPE: PRT
<213> ORGANISM: Artificial
<220> FEATURE:
<223> OTHER INFORMATION: Synthetic

<400> SEQUENCE: 6

Val Ile Ser Thr Tyr Tyr Gly Asn Thr Asn Tyr Asn Gln Lys Phe Lys
1 5 10 15

Gly

<210> SEQ ID NO 7
<211> LENGTH: 17
<212> TYPE: PRT
<213> ORGANISM: Artificial
<220> FEATURE:
<223> OTHER INFORMATION: Synthetic

<400> SEQUENCE: 7

Val Ile Asp Thr Tyr Tyr Gly Lys Thr Asn Tyr Asn Gln Lys Phe Glu
1 5 10 15

Gly

<210> SEQ ID NO 8
<211> LENGTH: 16
<212> TYPE: PRT
<213> ORGANISM: Artificial
<220> FEATURE:
<223> OTHER INFORMATION: Synthetic

<400> SEQUENCE: 8

Ser Ile Ser Ser Gly Gly Ser Thr Tyr Tyr Pro Asp Ser Val Lys Gly 1 5 10 15

<210> SEQ ID NO 9
<211> LENGTH: 16
<212> TYPE: PRT
<213> ORGANISM: Artificial
<220> FEATURE:
<223> OTHER INFORMATION: Synthetic

<400> SEQUENCE: 9

Ser Ile Ser Ser Gly Gly Arg Met Tyr Tyr Pro Asp Thr Val Lys Gly
1 5 10 15

<210> SEQ ID NO 10
<211> LENGTH: 17
<212> TYPE: PRT
<213> ORGANISM: Artificial
<220> FEATURE:
<223> OTHER INFORMATION: Synthetic

<400> SEQUENCE: 10

Val Ile Asn Pro Gly Ser Gly Arg Thr Asn Tyr Asn Glu Lys Phe Lys
1 5 10 15

Gly

<210> SEQ ID NO 11
<211> LENGTH: 17
<212> TYPE: PRT
<213> ORGANISM: Artificial
<220> FEATURE:
<223> OTHER INFORMATION: Synthetic

<400> SEQUENCE: 11

Val Ile Ser Pro Gly Ser Gly Ile Ile Asn Tyr Asn Glu Lys Phe Lys
1 5 10 15

Gly

<210> SEQ ID NO 12
<211> LENGTH: 17
<212> TYPE: PRT
<213> ORGANISM: Artificial
<220> FEATURE:
<223> OTHER INFORMATION: Synthetic

<400> SEQUENCE: 12

Gly Gly Leu Arg Arg Gly Asp Arg Pro Ser Leu Arg Tyr Ala Met Asp
1 5 10 15

Tyr

<210> SEQ ID NO 13
<211> LENGTH: 17
<212> TYPE: PRT
<213> ORGANISM: Artificial
<220> FEATURE:
<223> OTHER INFORMATION: Synthetic

<400> SEQUENCE: 13

Gly Gly Phe Arg Arg Gly Asp Arg Pro Ser Leu Arg Tyr Ala Met Asp
1 5 10 15

Ser

<210> SEQ ID NO 14
<211> LENGTH: 12
<212> TYPE: PRT
<213> ORGANISM: Artificial

<220> FEATURE:
<223> OTHER INFORMATION: Synthetic

<400> SEQUENCE: 14

Gly Ala Ile Tyr Asp Gly Tyr Tyr Val Phe Ala Tyr
1 5 10

<210> SEQ ID NO 15
<211> LENGTH: 12
<212> TYPE: PRT
<213> ORGANISM: Artificial
<220> FEATURE:
<223> OTHER INFORMATION: Synthetic

<400> SEQUENCE: 15

Gly Ser Ile Tyr Asp Gly Tyr Tyr Val Phe Pro Tyr
1 5 10

<210> SEQ ID NO 16
<211> LENGTH: 12
<212> TYPE: PRT
<213> ORGANISM: Artificial
<220> FEATURE:
<223> OTHER INFORMATION: Synthetic

<400> SEQUENCE: 16

Ile Tyr Tyr Gly Pro His Ser Tyr Ala Met Asp Tyr
1 5 10

<210> SEQ ID NO 17
<211> LENGTH: 11
<212> TYPE: PRT
<213> ORGANISM: Artificial
<220> FEATURE:
<223> OTHER INFORMATION: Synthetic

<400> SEQUENCE: 17

Ile Asp Tyr Ser Gly Pro Tyr Ala Val Asp Asp
1 5 10

<210> SEQ ID NO 18
<211> LENGTH: 15
<212> TYPE: PRT
<213> ORGANISM: Artificial
<220> FEATURE:
<223> OTHER INFORMATION: Synthetic

<400> SEQUENCE: 18

Arg Ala Ser Gln Ser Val Ser Thr Ser Ser Tyr Ser Tyr Met Tyr
1 5 10 15

<210> SEQ ID NO 19
<211> LENGTH: 15
<212> TYPE: PRT
<213> ORGANISM: Artificial
<220> FEATURE:
<223> OTHER INFORMATION: Synthetic

<400> SEQUENCE: 19

Arg Ala Ser Gln Ser Val Ser Ile Ser Thr Tyr Ser Tyr Ile His
1 5 10 15

<210> SEQ ID NO 20
<211> LENGTH: 12
<212> TYPE: PRT
<213> ORGANISM: Artificial
<220> FEATURE:
<223> OTHER INFORMATION: Synthetic

<400> SEQUENCE: 20

Ser Ala Ser Ser Ser Val Ser Ser Ser Tyr Leu Tyr
1 5 10

<210> SEQ ID NO 21
<211> LENGTH: 12
<212> TYPE: PRT
<213> ORGANISM: Artificial
<220> FEATURE:
<223> OTHER INFORMATION: Synthetic

<400> SEQUENCE: 21

Ser Ala Asn Ser Ser Val Ser Ser Ser Tyr Leu Tyr
1 5 10

<210> SEQ ID NO 22
<211> LENGTH: 11
<212> TYPE: PRT
<213> ORGANISM: Artificial
<220> FEATURE:
<223> OTHER INFORMATION: Synthetic

<400> SEQUENCE: 22

Lys Ala Ser Leu Asp Val Arg Thr Ala Val Ala
1 5 10

<210> SEQ ID NO 23
<211> LENGTH: 11
<212> TYPE: PRT
<213> ORGANISM: Artificial
<220> FEATURE:
<223> OTHER INFORMATION: Synthetic

<400> SEQUENCE: 23

Lys Ala Ser Gln Ala Val Asn Thr Ala Val Ala
1 5 10

<210> SEQ ID NO 24
<211> LENGTH: 7
<212> TYPE: PRT
<213> ORGANISM: Artificial
<220> FEATURE:
<223> OTHER INFORMATION: Synthetic

<400> SEQUENCE: 24

Tyr Ala Ser Asn Leu Glu Ser
1 5

<210> SEQ ID NO 25
<211> LENGTH: 7
<212> TYPE: PRT
<213> ORGANISM: Artificial
<220> FEATURE:
<223> OTHER INFORMATION: Synthetic

<400> SEQUENCE: 25

Ser Thr Ser Asn Leu Ala Ser
1 5

<210> SEQ ID NO 26
<211> LENGTH: 7
<212> TYPE: PRT
<213> ORGANISM: Artificial
<220> FEATURE:
<223> OTHER INFORMATION: Synthetic

<400> SEQUENCE: 26

Ser Ala Ser Tyr Arg Tyr Thr
1 5

<210> SEQ ID NO 27
<211> LENGTH: 7
<212> TYPE: PRT
<213> ORGANISM: Artificial
<220> FEATURE:
<223> OTHER INFORMATION: Synthetic

<400> SEQUENCE: 27

Ser Ala Ser Tyr Gln Tyr Thr
1 5

<210> SEQ ID NO 28
<211> LENGTH: 9
<212> TYPE: PRT
<213> ORGANISM: Artificial
<220> FEATURE:
<223> OTHER INFORMATION: Synthetic

<400> SEQUENCE: 28

Gln His Asn Trp Glu Ile Pro Phe Thr
1 5

<210> SEQ ID NO 29
<211> LENGTH: 9
<212> TYPE: PRT
<213> ORGANISM: Artificial
<220> FEATURE:
<223> OTHER INFORMATION: Synthetic

<400> SEQUENCE: 29

Gln His Ser Trp Glu Ile Pro Tyr Thr
1 5

<210> SEQ ID NO 30
<211> LENGTH: 9
<212> TYPE: PRT
<213> ORGANISM: Artificial
<220> FEATURE:
<223> OTHER INFORMATION: Synthetic

<400> SEQUENCE: 30

His Gln Trp Ser Ser Tyr Pro Pro Thr
1 5

<210> SEQ ID NO 31
<211> LENGTH: 9
<212> TYPE: PRT
<213> ORGANISM: Artificial
<220> FEATURE:
<223> OTHER INFORMATION: Synthetic

<400> SEQUENCE: 31

His Gln Trp Ser Thr Tyr Pro Pro Thr
1 5

<210> SEQ ID NO 32
<211> LENGTH: 9
<212> TYPE: PRT
<213> ORGANISM: Artificial
<220> FEATURE:
<223> OTHER INFORMATION: Synthetic

<400> SEQUENCE: 32

Gln Gln His Tyr Gly Ile Pro Trp Thr

-continued

```
1               5


<210> SEQ ID NO 33
<211> LENGTH: 9
<212> TYPE: PRT
<213> ORGANISM: Artificial
<220> FEATURE:
<223> OTHER INFORMATION: Synthetic

<400> SEQUENCE: 33

Gln His His Tyr Gly Val Pro Trp Thr
1               5
```

What is claimed is:

1. A method of inhibiting growth of [a cell from] a *smad4-deficient* tumor [that is smad4 deficient], comprising:

(a) determining the level of expression of smad4 in a cell from said [cancer] *smad4-deficient tumor*; and (b) treating [a cancer cell that is deficient in smad4 expression] *the smad4-deficient tumor* with [one or more] *an* αvβ6 antagonist antibody that selectively binds to the integrin αvβ6 [in said cancer cell], wherein said [one or more] antibody is an antibody [from] *produced by, or a humanized version of an antibody produced by,* a hybridoma selected from the group consisting of [2A1 (deposited under ATCC Accession No. ATCC PTA-3896), 2E5 (deposited under ATCC Accession No. ATCC PTA-3897),] 1A8 (deposited under ATCC Accession No. ATCC PTA-3647), 2B10 (deposited under ATCC Accession No. ATCC PTA-3648), 2B1 (deposited under ATCC Accession No. ATCC PTA-3646), 1G10 (deposited under ATCC Accession No. ATCC PTA-3898), 7G5 (deposited under ATCC Accession No. ATCC PTA-3899), 8G6 (deposited under ATCC Accession No. ATCC PTA-3645), *and* 3G9 (deposited under ATCC Accession No. ATCC PTA-3649), [or a humanized version thereof]

wherein said treatment results in the growth inhibition of said [cancer cell] *smad4-deficient tumor*.

2. The method of claim 1, wherein said tumor is a carcinoma.

3. The method of claim 2, wherein said carcinoma is an adenocarcinoma.

4. The method of claim 2, wherein said carcinoma is selected from the group consisting of a pancreatic carcinoma, a colorectal carcinoma, a cervical carcinoma, *a* squamous cell carcinoma, a head and neck carcinoma, a liver carcinoma, an ovarian carcinoma and a lung carcinoma.

5. The method of claim 2, wherein said carcinoma is a pancreatic carcinoma.

6. The method of claim [4] *2*, wherein said [squamous cell] carcinoma is an esophageal carcinoma.

7. The method of claim 2, wherein said carcinoma is a colorectal carcinoma.

8. The method of claim 2, wherein said carcinoma is a cervical carcinoma.

9. The method of claim 2, wherein said carcinoma is a head and neck carcinoma.

10. The method of claim 1, wherein said [monoclonal] antibody is *an antibody produced by the hybridoma* 3G9 (*deposited under ATCC Accession No. ATCC PTA-3649*) *or a humanized version thereof.*

11. The method of claim 1, wherein said [monoclonal] antibody is *an antibody produced by the hybridoma* 8G6 (*deposited under ATCC Accession No. ATCC PTA-3645*) *or a humanized version thereof.*

12. The method of claim 1, wherein said [monoclonal] antibody is a humanized monoclonal antibody.

13. The method of claim 12, wherein said humanized monoclonal antibody is hu3G9 (BG00011).

14. The method of claim 12, wherein said humanized monoclonal antibody is hu8G6.

15. The method of claim 1, wherein said antibody is conjugated with at least one detectable label.

16. The method of claim 15, wherein said detectable label is selected from the group consisting of a chromogenic label, an enzyme label, a radioisotopic label, a non-radioactive isotopic label, a fluorescent label, a toxic label, a chemiluminescent label, an X-radiographic label, a spin label and a nuclear magnetic resonance contrast agent label.

17. The method of claim 16, wherein said *detectable label is a* chromogenic label [is] selected from the group consisting of diaminobenzidine and 4 hydroxyazo-benzene-2-carboxylic acid.

18. The method of claim 16, wherein said *detectable label is an* enzyme label [is] selected from the group consisting of malate dehydrogenase, staphylococcal nuclease, delta 5 steroid isomerase, yeast alcohol dehydrogenase, alpha glycerol phosphate dehydrogenase, triose phosphate isomerase, peroxidase, alkaline phosphatase, asparaginase, glucose oxidase, β galactosidase, ribonuclease, urease, catalase, glucose 6 phosphate dehydrogenase, glucoamylase and acetylcholine esterase.

19. The method of claim 16, wherein said *detectable label is a* radioisotopic label [is] selected from the group consisting of [3H, 111 In, 125I, 131I, 32P, 35S, 14C, 51Cr, 57To, 58Co, 59Fe, 75Se, 152Eu, 90Y, 67Cu, 217Ci, 211At, 212Pb, 47Sc] $^{3}H$, $^{111}In$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$, and [109Pd] $^{109}Pd$.

20. The method of claim 16, wherein said *detectable label is a* non-radioactive isotopic label [is] selected from the group consisting of [157Gd, 55Mn, 162Dy, 52Tr, 56Fe, 99mTc] $^{157}Gd$, $^{55}Mn$, $^{162}Dy$, $^{52}Tr$, $^{56}Fe$, $^{99}mTc$, and [112In] $^{112}In$.

21. The method of claim 16, wherein said *detectable label is a* fluorescent label [is] selected from the group consisting of a [152Eu] $^{152}Eu$ label, a fluorescein label, an isothiocyanate label, a rhodamine label, a phycoerythrin label, a phycocyanin label, an allophycocyanin label, a Green Fluorescent Protein (GFP) label, an ophthaldehyde label and a fluorescamine label.

22. The method of claim 16, wherein said *detectable label is a* toxic label [is] selected from the group consisting of a diphtheria toxin label, a ricin label and a cholera toxin label.

23. The method of claim 16, wherein said *detectable label is a* chemiluminescent label [is] selected from the group consisting of a luminol label, an isoluminol label, an aromatic acridinium ester label, an imidazole label, an acridinium salt label, an oxalate ester label, a luciferin label, a luciferase label and an aequorin label.

24. The method of claim 16, wherein said *detectable label is an* X-radiographic label *that* is barium or cesium.

25. The method of claim 16, wherein said *detectable label is a* spin label *that* is deuterium.

26. The method of claim 16, wherein said *detectable label is a* nuclear magnetic resonance contrast agent label [is] selected from the group consisting of Gd, Mn and [iron] *Fe*.

27. A method of increasing the responsiveness of a smad4-deficient cancer [cell] to treatment with a growth-inhibiting chemotherapeutic [compounds] *compound*, comprising:

(a) determining the level of expression of smad4 in a cell from said *smad4-deficient* cancer; and (b) treating [a] *the smad4-deficient* cancer [cell that is deficient in smad4 expression] with [one or more] *an* αvβ6-antagonist [antibodies] *antibody* that selectively [bind] *binds* to the integrin αvβ6 [in said cancer cell], wherein said [one or more] antibody is an antibody [from] *produced by, or a humanized verison of an antibody produced by,* a hybridoma selected from the group consisting of [2A1 (deposited under ATCC Accession No. ATCC PTA-3896), 2E5 (deposited under ATCC Accession No. ATCC PTA-3897),] 1A8 (deposited under ATCC Accession No. ATCC PTA-3647), 2B10 (deposited under ATCC Accession No. ATCC PTA-3648), 2B1 (deposited under ATCC Accession No. ATCC PTA-3646), 1G10 (deposited under ATCC Accession No. ATCC PTA-3898), 7G5 (deposited under ATCC Accession No. ATCC PTA-3899), 8G6 (deposited under ATCC Accession No. ATCC PTA-3645), *and* 3G9 (deposited under ATCC Accession No. ATCC PTA-3649), [or a humanized version thereof]

wherein said treatment with said [blocking antibodies] *antibody* results in increased responsiveness of said *smad4-deficient* cancer [cell] to [one or more] *the* growth-inhibiting chemotherapeutic [compounds] *compound* as compared to the growth inhibition of said *smad4-deficient* cancer [cell produced by] *treated with* said chemotherapeutic [agent] *compound* alone.

28. The method of claim 27, wherein said growth-inhibiting chemotherapeutic compound is selected from the group consisting of cisplatin, carboplatin, oxaliplatin, paclitaxel, gemcitabine, adriamycin, melphalan, methotrexate, 5-fluorouracil, etoposide, mechlorethamine, cyclophosphamide, bleomycin, a calicheamicin, a maytansine, a trichothene, CC1065, diphtheria A chain, Pseudomonas aeruginosa exotoxin A chain, ricin A chain, abrin A chain, modeccin A chain, alpha-sarcin, an Aleuritesfordii protein, a dianthin protein, a Phytolaca americana protein, [momordica] *Momordica* charantia inhibitor, curcin, crotin, [sapaonaria] *Sapaonaria* officinalis inhibitor, gelonin, mitogellin, restrictocin, phenomycin, enomycin, a tricothecene, a ribonuclease, and a deoxyribonuclease.

29. The method of claim 28, wherein said growth-inhibiting chemotherapeutic compound is gemcitabine, adriamycin or paclitaxel.

*30. The method of claim 1, wherein said antibody is an antibody produced by the hybridoma 1A8 (deposited under ATCC Accession No. ATCC PTA-3647) or a humanized version thereof.*

*31. The method of claim 27, wherein said antibody is hu3G9 (BG00011).*

*32. The method of claim 27, wherein said antibody is hu8G6.*

*33. The method of claim 27, wherein said antibody is an antibody produced by the hybridoma 3G9 (deposited under ATCC Accession No. ATCC PTA-3649) or a humanized version thereof.*

*34. The method of claim 27, wherein said antibody is an antibody produced by the hybridoma 8G6 (deposited under ATCC Accession No. ATCC PTA-3645) or a humanized version thereof.*

*35. The method of claim 27, wherein said antibody is an antibody produced by the hybridoma 1A8 (deposited under ATCC Accession No. ATCC PTA-3647) or a humanized version thereof.*

*36. The method of claim 1, wherein the antibody comprises a heavy chain and a light chain, wherein the heavy and light chains comprise complementarity determining regions (CDRs) 1, 2, and 3 as follows:*

*heavy chain CDR 1 comprising an amino acid sequence set forth in SEQ ID NO.: 3;*

*heavy chain CDR 2 comprising an amino acid sequence set forth in SEQ ID NO.: 9;*

*heavy chain CDR 3 comprising an amino acid sequence set forth in SEQ ID NO.: 15;*

*light chain CDR 1 comprising an amino acid sequence set forth in SEQ ID NO.: 20;*

*light chain CDR 2 comprising an amino acid sequence set forth in SEQ ID NO.: 25; and*

*light chain CDR 3 comprising an amino acid sequence set forth in SEQ ID NO.: 31.*

*37. The method of claim 1, wherein the antibody comprises a heavy chain and a light chain, wherein the heavy and light chains comprise CDRs 1, 2, and 3 as follows:*

*heavy chain CDR 1 comprising an amino acid sequence set forth in SEQ ID NO.: 1;*

*heavy chain CDR 2 comprising an amino acid sequence set forth in SEQ ID NO.: 6;*

*heavy chain CDR 3 comprising an amino acid sequence set forth in SEQ ID NO.: 12;*

*light chain CDR 1 comprising an amino acid sequence set forth in SEQ ID NO.: 18;*

*light chain CDR 2 comprising an amino acid sequence set forth in SEQ ID NO.: 24; and*

*light chain CDR 3 comprising an amino acid sequence set forth in SEQ ID NO.: 28.*

*38. The method of claim 1, wherein the antibody comprises a heavy chain and a light chain, wherein the heavy and light chains comprise CDRs 1, 2, and 3 as follows:*

*heavy chain CDR 1 comprising an amino acid sequence set forth in SEQ ID NO.: 2;*

*heavy chain CDR 2 comprising an amino acid sequence set forth in SEQ ID NO.: 7;*

*heavy chain CDR 3 comprising an amino acid sequence set forth in SEQ ID NO.: 13;*

*light chain CDR 1 comprising an amino acid sequence set forth in SEQ ID NO.: 19;*

*light chain CDR 2 comprising an amino acid sequence set forth in SEQ ID NO.: 24; and*

*light chain CDR 3 comprising an amino acid sequence set forth in SEQ ID NO.: 29.*

*39. The method of claim 27, wherein the antibody comprises a heavy chain and a light chain, wherein the heavy and light chains comprise CDRs 1, 2, and 3 as follows:*

*heavy chain CDR 1 comprising an amino acid sequence set forth in SEQ ID NO.: 3;*

*heavy chain CDR 2 comprising an amino acid sequence set forth in SEQ ID NO.: 9;*

*heavy chain CDR 3 comprising an amino acid sequence set forth in SEQ ID NO.: 15;*

*light chain CDR 1 comprising an amino acid sequence set forth in SEQ ID NO.: 20;*

*light chain CDR 2 comprising an amino acid sequence set forth in SEQ ID NO.: 25; and*

*light chain CDR 3 comprising an amino acid sequence set forth in SEQ ID NO.: 31.*

*40. The method of claim 27, wherein the antibody comprises a heavy chain and a light chain, wherein the heavy and light chains comprise CDRs 1, 2, and 3 as follows:*

*heavy chain CDR 1 comprising an amino acid sequence set forth in SEQ ID NO.: 1;*

*heavy chain CDR 2 comprising an amino acid sequence set forth in SEQ ID NO.: 6;*

*heavy chain CDR 3 comprising an amino acid sequence set forth in SEQ ID NO.: 12;*

*light chain CDR 1 comprising an amino acid sequence set forth in SEQ ID NO.: 18;*

*light chain CDR 2 comprising an amino acid sequence set forth in SEQ ID NO.: 24; and*

*light chain CDR 3 comprising an amino acid sequence set forth in SEQ ID NO.: 28.*

*41. The method of claim 27, wherein the antibody comprises a heavy chain and a light chain, wherein the heavy and light chains comprise CDRs 1, 2, and 3 as follows:*

*heavy chain CDR 1 comprising an amino acid sequence set forth in SEQ ID NO.: 2;*

*heavy chain CDR 2 comprising an amino acid sequence set forth in SEQ ID NO.: 7;*

*heavy chain CDR 3 comprising an amino acid sequence set forth in SEQ ID NO.: 13;*

*light chain CDR 1 comprising an amino acid sequence set forth in SEQ ID NO.: 19;*

*light chain CDR 2 comprising an amino acid sequence set forth in SEQ ID NO.: 24; and*

*light chain CDR 3 comprising an amino acid sequence set forth in SEQ ID NO.: 29.*

* * * * *

UNITED STATES PATENT AND TRADEMARK OFFICE

CERTIFICATE OF CORRECTION

PATENT NO. : RE44,681 E
APPLICATION NO. : 13/863646
DATED : December 31, 2013
INVENTOR(S) : Shelia M. Violette and Louise A. Koopman It is certified that error appears in the above-identified patent and that said Letters Patent is hereby corrected as shown below:

Title page

Item [57] Column 2, Abstract,

Line 13, delete "$\equiv_{v}\beta_{6}$" and insert -- $\alpha_{v}\beta_{6}$ --.

References Cited

Page 2, Column 1, Other Publications
Line 9, delete "with a" and insert -- with --.

Page 2, Column 2, Other Publications
Line 1, delete "544-551" and insert -- S44-S51 --.

Page 4, Column 2, Other Publications
Line 54, delete "patitents" and insert -- patients --.

Page 5, Column 1, Other Publications
Line 36, delete "TGF-betal" and insert -- TGF-beta 1 --.

Page 5, Column 1, Other Publications
Line 57, delete "Assesment" and insert -- Assessment --.

Page 5, Column 2, Other Publications
Line 55, delete "ntegrin" and insert -- integrin --.

In the Claims

Column 56
Claim 21, line 60, delete "ophthaldehyde" and insert -- o-phthaldehyde --.

Signed and Sealed this
Sixth Day of May, 2014

Michelle K. Lee

Michelle K. Lee
*Deputy Director of the United States Patent and Trademark Office*

Column 57
Claim 27, line 22, delete “verison” and insert -- version --.

Column 57
Claim 28, line 48, delete “trichothene” and insert -- trichothecene --.

Column 57
Claim 28, line 52, delete “Phytolaca” and insert -- Phytolacca --.

Column 57
Claim 28, line 53, delete “*Sapaonaria*” and insert -- *Saponaria* --.

Column 57
Claim 28, line 55, delete “tricothecene” and insert -- trichothecene --.